United States Patent
Baumhof et al.

(10) Patent No.: US 9,907,862 B2
(45) Date of Patent: *Mar. 6, 2018

(54) DISULFIDE-LINKED POLYETHYLENEGLYCOL/PEPTIDE CONJUGATES FOR THE TRANSFECTION OF NUCLEIC ACIDS

(71) Applicant: CureVac AG, Tübingen (DE)

(72) Inventors: Patrick Baumhof, Dusslingen (DE); Thomas Schlake, Gundelfingen (DE)

(73) Assignee: CureVac AG, Tübingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/065,769

(22) Filed: Mar. 9, 2016

(65) Prior Publication Data

US 2016/0317679 A1  Nov. 3, 2016

Related U.S. Application Data

(63) Continuation of application No. 14/195,864, filed on Mar. 4, 2014, now Pat. No. 9,314,535, which is a continuation of application No. 13/378,241, filed as application No. PCT/EP2010/005438 on Sep. 3, 2010, now Pat. No. 8,703,906, which is a continuation-in-part of application No. 12/553,559, filed on Sep. 3, 2009, now abandoned.

(51) Int. Cl.

| | | |
|---|---|---|
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *A61K 48/00* | (2006.01) | |
| *A61K 47/60* | (2017.01) | |
| *A61K 47/64* | (2017.01) | |

(52) U.S. Cl.
CPC .......... *A61K 48/0041* (2013.01); *A61K 47/60* (2017.08); *A61K 47/6455* (2017.08)

(58) Field of Classification Search
CPC ......... A61K 38/00; C07K 14/00; C07K 16/00
See application file for complete search history.

(56) References Cited

U.S. PATENT DOCUMENTS

| | | | |
|---|---|---|---|
| 3,906,092 A | 9/1975 | Hilleman et al. | |
| 4,373,071 A | 2/1983 | Itakura | |
| 4,401,796 A | 8/1983 | Itakura | |
| 4,415,732 A | 11/1983 | Caruthers et al. | |
| 4,578,399 A | 3/1986 | Schorlemmer et al. | |
| 5,516,652 A | 5/1996 | Abramovitz et al. | |
| 5,663,153 A | 9/1997 | Hutcherson et al. | |
| 5,663,163 A | 9/1997 | Takaya et al. | |
| 5,844,075 A | 12/1998 | Kawakami et al. | |
| 5,965,720 A | 10/1999 | Gryaznov et al. | |
| 6,096,307 A | 8/2000 | Braswell et al. | |
| 6,218,371 B1 | 4/2001 | Krieg et al. | |
| 6,239,116 B1 | 5/2001 | Krieg et al. | |
| 6,322,967 B1 | 11/2001 | Parkin | |
| 6,406,705 B1 | 6/2002 | Davis et al. | |
| 6,498,148 B1 | 12/2002 | Raz | |
| 6,514,948 B1 | 2/2003 | Raz et al. | |
| 6,552,006 B2 | 4/2003 | Raz et al. | |
| 6,589,940 B1 | 7/2003 | Raz et al. | |
| 6,610,661 B1 | 8/2003 | Carson et al. | |
| 6,689,759 B1 | 2/2004 | Jacob et al. | |
| 6,716,434 B1 | 4/2004 | Ansley et al. | |
| 7,001,890 B1 | 2/2006 | Wagner et al. | |
| 7,208,478 B2 | 4/2007 | Carson et al. | |
| 7,407,944 B2 | 8/2008 | Agrawal et al. | |
| 7,470,674 B2 | 12/2008 | Agrawal et al. | |
| 7,517,862 B2 | 4/2009 | Agrawal et al. | |
| 2003/0133942 A1 | 7/2003 | Segal | |
| 2003/0225016 A1 | 12/2003 | Fearon et al. | |
| 2004/0006010 A1 | 1/2004 | Carson et al. | |

(Continued)

FOREIGN PATENT DOCUMENTS

| | | |
|---|---|---|
| AU | 776268 | 12/2000 |
| DE | 102004035227 | 2/2002 |

(Continued)

OTHER PUBLICATIONS

"Cell-penetrating peptide," *Wikipedia*, located at http://en.wikipedia.org/wiki/Cell-penetrating_peptide, downloaded Dec. 11, 2012.

"DOC/Alum Complex," Violin: Vaccine investigation and online information network, located at http://www.violinet.org/vaxjo/vaxjo_detail.php?c_vaxjo_id=49, downloaded on Aug. 28, 2012.

"QS21," Wikipedia, located at http://en.wikipedia.org/wiki/QS21, downloaded on Dec. 11, 2012.

"Ribi vaccine adjuvant," Violin: Vaccine investigation and online information network, located at http://www.violinet.org/vaxjo/vaxjo_detail.php?c_vaxjo_id=21, downloaded on Dec. 17, 2012.

"SPT (Antigen Formulation)," Violin: Vaccine investigation and online information network, located at http://www.violinet.org/vaxjo/vaxjo_detail.php?c_vaxjo_id=72, downloaded on Aug. 21, 2012.

(Continued)

*Primary Examiner* — Kaipeen Yang
(74) *Attorney, Agent, or Firm* — Parker Highlander PLLC

(57) ABSTRACT

The present invention is directed to an inventive polymeric carrier molecule according to generic formula (I) and variations thereof, which allows for efficient transfection of nucleic acids into cells in vivo and in vitro, a polymeric carrier cargo complex formed by a nucleic acid and the inventive polymeric carrier molecule, but also to methods of preparation of this inventive polymeric carrier molecule and of the inventive polymeric carrier cargo complex. The present invention also provides methods of application and use of this inventive polymeric carrier molecule and the inventive polymeric carrier cargo complex as a medicament, for the treatment of various diseases, and in the preparation of a pharmaceutical composition for the treatment of such diseases.

25 Claims, 16 Drawing Sheets

(56) References Cited

U.S. PATENT DOCUMENTS

Figure 1:
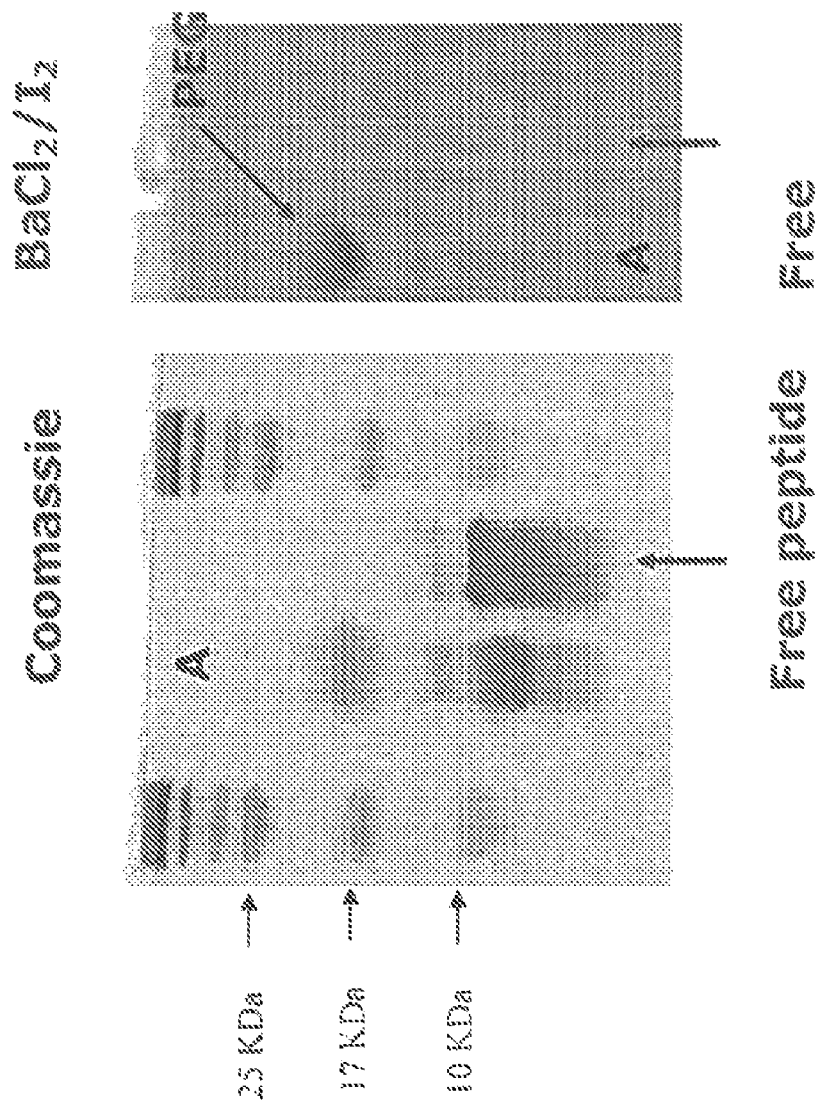

| | | |
|---|---|---|
| 2004/0006034 A1 | 1/2004 | Raz et al. |
| 2004/0019007 A1 | 1/2004 | Monahan et al. |
| 2004/0047869 A1 | 3/2004 | Garcon et al. |
| 2004/0052763 A1 | 3/2004 | Mond et al. |
| 2005/0032730 A1 | 2/2005 | Von Der Mulbe et al. |
| 2005/0037494 A1 | 2/2005 | Hecker et al. |
| 2005/0059624 A1 | 3/2005 | Hoerr et al. |
| 2005/0130918 A1 | 6/2005 | Agrawal et al. |
| 2005/0250723 A1 | 11/2005 | Hoerr et al. |
| 2006/0172966 A1 | 8/2006 | Lipford et al. |
| 2006/0188490 A1 | 8/2006 | Hoerr et al. |
| 2006/0251623 A1 | 11/2006 | Bachmann et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2008/0248067 A1 | 10/2008 | Frazer et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0250225 A1 | 10/2011 | Fotin-Mleczek et al. |
| 2011/0311472 A1 | 12/2011 | Hoerr et al. |
| 2012/0021043 A1 | 1/2012 | Kramps et al. |
| 2012/0258046 A1 | 10/2012 | Mutzke |
| 2013/0142818 A1 | 6/2013 | Baumhof et al. |

FOREIGN PATENT DOCUMENTS

| | | |
|---|---|---|
| DE | 10148886 | 4/2003 |
| DE | 69819150 | 7/2004 |
| DE | 102006007433 | 8/2007 |
| EP | 0347501 | 12/1989 |
| EP | 0772619 | 5/1997 |
| EP | 0839912 | 5/1998 |
| EP | 1063232 | 3/2001 |
| EP | 1083232 | 3/2001 |
| EP | 1167379 | 1/2002 |
| EP | 1374894 | 1/2004 |
| EP | 1393745 | 3/2004 |
| EP | 1564291 | 8/2005 |
| EP | 1905844 | 2/2008 |
| JP | 2005-521749 | 7/2005 |
| JP | 2008-542500 | 11/2008 |
| KR | 10-1003622 | 9/2003 |
| KR | 10-1051785 | 1/2005 |
| KR | 10-1032853 | 4/2005 |
| WO | WO 1991/005560 | 5/1991 |
| WO | WO 1994/017093 | 8/1994 |
| WO | WO 1994/017792 | 8/1994 |
| WO | WO 1998/019710 | 5/1998 |
| WO | WO 1998/047913 | 10/1998 |
| WO | WO 1999/053961 | 10/1999 |
| WO | WO 2000/075304 | 12/2000 |
| WO | WO 2001/004135 | 1/2001 |
| WO | WO 2001/054720 | 8/2001 |
| WO | WO 2001/075164 | 10/2001 |
| WO | WO 2001/093902 | 12/2001 |
| WO | WO 2001/097843 | 12/2001 |
| WO | WO 2002/000594 | 1/2002 |
| WO | WO 2002/000694 | 1/2002 |
| WO | WO 2002/078614 | 10/2002 |
| WO | WO 2002/098443 | 12/2002 |
| WO | WO 2003-000227 | 1/2003 |
| WO | WO 2003/028656 | 4/2003 |
| WO | WO 2003/057822 | 7/2003 |
| WO | WO 2003/059381 | 7/2003 |
| WO | WO 2003/066649 | 8/2003 |
| WO | WO 2003/068942 | 8/2003 |
| WO | WO 2003/086280 | 10/2003 |
| WO | WO 2004/004743 | 1/2004 |
| WO | WO 2004/058159 | 7/2004 |
| WO | WO 2004/064782 | 8/2004 |
| WO | WO 2004/092329 | 10/2004 |
| WO | WO 2005/001022 | 1/2005 |
| WO | WO 2005/030259 | 4/2005 |
| WO | WO 2005/062947 | 7/2005 |
| WO | WO 2005/097993 | 10/2005 |
| WO | WO 2006/029223 | 3/2006 |
| WO | WO 2006/046978 | 5/2006 |
| WO | WO 2006/080946 | 8/2006 |
| WO | WO 2006/116458 | 11/2006 |
| WO | WO 2007/008300 | 1/2007 |
| WO | WO 2007/031319 | 3/2007 |
| WO | WO 2007/031322 | 3/2007 |
| WO | WO 2007/042554 | 4/2007 |
| WO | WO 2007/051303 | 5/2007 |
| WO | WO 2007/062107 | 5/2007 |
| WO | WO 2007/069068 | 6/2007 |
| WO | WO 2007/124755 | 11/2007 |
| WO | WO 2008/014979 | 2/2008 |
| WO | WO 2008/022046 | 2/2008 |
| WO | WO 2008/052770 | 5/2008 |
| WO | WO 2009/030254 | 3/2009 |
| WO | WO 2009/030481 | 3/2009 |
| WO | WO 2009/053700 | 4/2009 |
| WO | WO 2009/086640 | 7/2009 |
| WO | WO 2010/037408 | 4/2010 |
| WO | WO 2010/037539 | 4/2010 |
| WO | WO 2011/026641 | 3/2011 |
| WO | WO 2012/013326 | 2/2012 |
| WO | WO 2012-113413 | 8/2012 |
| WO | WO 2013/113326 | 8/2013 |
| WO | WO 2013/113501 | 8/2013 |
| WO | WO 2013/113502 | 8/2013 |
| WO | WO 2013/174409 | 11/2013 |

OTHER PUBLICATIONS

"Virus-like particle," Wikipedia, located at http://en.wikipedia.org/wiki/virus-like_particle, downloaded on Sep. 3, 2012.

Adams et al., "Preparation and hybridization properties of oligonucleotides containing 1-alpha-D-arabinofuranosylthymine", *Nucleic Acids Res.*, 19(13):3647-51, 1991.

Agrawal, "Antisense oligonucleotides: towards clinical trials", *Trends Biotechnol.*, 14(10):376-387, 1996.

Ara et al., "Zymosan enhances the immune response to DNA vaccine for human immunodeficiency virus type-1 through the activation of complement system", *Immunology*, 103(1):98-105, 2001.

Bayard et al., "Antiviral activity in L1210 cells of liposome-encapsulated (2'-5')oligo(adenylate)analogues", *Eur J Biochem.*, 151(2):319-326, 1985.

Berzofsky et al., "Progress on new vaccine strategies against chronic viral infections", *J Clin Invest.*, 114(4):450-62, 2004.

Bettinger T. et al., "Peptide-mediated RNA delivery: a novel approach for enhanced transfection of primary and Post-mitotic cells," *Nucleic Acids Research*, vol. 29, No. 18, pp. 3882-3891, 2001.

Blaxter et al., "The *Brugia malayi* genome project: expressed sequence tags and gene discovery", *Transactions of the Royal Society of Tropical Medicine and Hygiene*, 96(1):1-17, 2002.

Bocchia et al., "Antitumor vaccination: where we stand", *Heamatologica*, 85(11):1172-1206, 2000.

Bolhassani A. et al., "Improvement of different vaccine delivery systems for cancer therapy," *Molecular Cancer*, vol. 10, No. 1, p. 3, Jan. 7, 2011.

Bot A. et al., "Enhanced protection against influenza virus of mice immunized as newborns with a mixture of plasmids expressing hemagglutinin and nucleoprotein," *Vaccine*, 16, No. 17, pp. 1675-1682, Oct. 1, 1998.

Bot A. et al., "Genetic immunization of neonates, Microbes and Infection, Institut Pasteur," vol. 4, No. 4, pp. 511-520, Apr. 2002.

Bot A. et al., "Induction of humoral and cellular immunity against influenza virus by immunization of newborn mice with a plasmid bearing a hemagglutinin gene," *International Immunology*, vol. 9, No. 11, pp. 1641-1650, Dec. 31, 1997.

(56) References Cited

OTHER PUBLICATIONS

Brito et al., "Non-viral eNOS gene delivery and transfection with stents for the treatment of restenosis," *BioMedical Engineering OnLine*, 9:56, 2010.

Burke R.S. et al., "Extracellular barriers to in Vivo PEI and PEGylated PEI polyplex-mediated gene delivery to the liver," *Bioconjug Chem.* Mar. 2008;19(3):693-704. Epub Feb. 23, 2008.

Buteau et al., "Challenges in the development of effective peptide vaccines for cancer", *Mayo Clin Proc.*, 77:339-349, 2002.

CAPLUS accession No. 190686-49-8; *Brugia malayi* strain TRS Labs conie RRAMCA1537 EST; *Chemical Abstracts Services*; Database CAPLUS; Jun. 2009.

Carralot J-P. et al., "Polarization of immunity induced by direct injection of naked sequence-stabilized mRNA vaccines," *CMLS Cellular and Molecular Life Sciences*, vo. 61, No. 18, pp. 2418-2424, Sep. 1, 2004.

Casciato et al., Manual of Clinical Oncology, 6th Edition, Lippincott Williams & Wilkins, 2009.

Cooper et al., "CPG 7909 adjuvant improves hepatitis B virus vaccine seroprotection in antiretroviral-treated HIV-infected adults," *AIDS*, 19:1473-1479, 2005.

Danhier et al., "PLGA-based nanoparticles: An overview of biomedical applications," *Journal of Controlled Release*, 161:505-522, 2012.

Deshayes S. et al., "Cell-penetrating peptides: tools for intracellular delivery of therapeutics," *Cell Mol Life Sci.*, 62(16):1839-49. Review. 2005.

Diebold et al., "Innate antiviral responses by means of TLR7-mediated recognition of single-stranded RNA", *Science*, 1529-1531, 2004.

Dmitriev, "Bactenecin 7 peptide fragment as a tool for intracellular delivery of a phosphorescent oxygen sensor," *FEBS Journal*, 277:4651-4661, 2010.

EBI Database accession No. BP836659; *Arabidopsis thaliana* clone RAFL22-17-C17 EST; Database EMBL; Jan. 2005.

EBI Database accession No. CZ193289; PST12107-MICB1 *Mus musculus* genomic clone PST12107-NR; Database EMBL; Feb. 2005.

EBI Database accession No. DN868844; NEIBank analysis of Dog lens; Wistow, G., Database EMBL; Apr. 2005.

Eliyahu et al., "Polymers for DNA delivery," *Molecules*, 10:34-64, 2005.

EMBL accession No. AA430815; Brugia malayi strain TRS Labs clone RRAMCA1537 EST; Database EMBL; May 1997.

Fajac I. et al., "Histidylated polylysine as a synthetic vector for gene transfer into immortalized cystic fibrosis airway surface and airway gland serous cells," *J Gene Med.* 2(5):368-78. Sep.-Oct. 2000.

Feroze-Merzoug et al., "Molecular profiling in prostate cancer", *Cancer and Metastasis Reviews*, 20:165-171, 2001.

Fire et al., "Potent and specific genetic interferences by double-stranded RNA in *Caenorhabditis elegans*", 391:806-811, 1998.

Foerg C. et al., "On the biomedical promise of cell penetrating peptides: limits versus prospects," *J Pharm Sci.* Jan. 2008;97(1):144-62.

Fotin-Mleczek, M. et al., "Messenger RNA-based vaccines with dual activity induce balanced TLR-7 dependent adaptive immune responses and provide antitumor activity," *Journal of lmmunotheraphy*, vo. 34, No. 1, pp. 1-15, Jan. 1, 2011.

Fox, "Squalene emulsions for parenteral vaccine and drug delivery," *Molecules*, 14:3286-3312, 2009.

Fujita T et al., "Calcium enhanced cellular delivery of tetraarginine-PEG-lipid-coated DNA/protamine complexes," *International Journal of Pharmaceutics*, vol. 368, No. 1-2, pp. 186-192, Feb. 23, 2009.

Galbraith et al., "Complement activation and hemodynamic changes following intravenous administration of phosphorothioate oligonucleotides in the monkey", *Antisense Research and Development*, 4:201-206, 1994.

Gao X et al., Nonviral gene delivery: what we know and what is next, *AAPS J.* 23;9(1):E92-104. Review. Mar. 2007.

Garinot et al., "PEGylated PLGA-based nanoparticles targeting M cells for oral vaccination," *Journal of controlled release*, vol. 120, No. 3, pp. 195-204, Jul. 17, 2007.

GenBank Accession No. JK489756.1, GI; 346421249, publicly available Sep. 2011.

Gerogieva et al., "Comparative study on the changes in photosynthetic activity of the homoiochlorophyllous desiccation-tolerant *Haberlea rhodopensis* and desiccation-sensitive spinach leaves during desiccation and rehydration", *Photosynthesis Research*, 65:191-203, 2005.

Giel-Peitraszuk M. et al., "Database Biosis," DB Acc. No. Prev199800116011, 1997.

Gravekamp et al., "Cancer vaccines in old age," *Experimental Gerontology*, vol. 42, No. 5, pp. 441-450, Apr. 14, 2007.

Gryaznov, "Oligonucleotide N3'-P5' phosphoramidates as potential therapeutic agents", *Biochimica et Biophysica Acta*, 1489:131-140, 1999.

Hamidi M. et al., "Pharmacokinetic consequences of pegylation," *Drug Deliv.*; 13(6) pp. 399-409, 2006.

Hardy et al., "Synergistic effects of gene delivery—co-formulation of small disulfide-linked dendritic polycations with Lipofectamine 2000", *Organic and Biomolecular Chemistry*, 7(4):789-793, 2009.

Hausch et al., "A novel carboxy-functionalized photocleavable dinucleotide analog for the selection to RNA catalysts", *Tetrahedron Letters*, 39(34):6157-6158, 1998.

Heffernan et al., "Disulfide-crosslinke plyion micelles for delivery of protein therapeutics", *Annals of Biomedical Engineering*, 37(10):1993-2002, 2009.

Heidenreich et al., "Chemically modified RNA: approaches and applications", *The FASEB Journal*, 7(1):90-6, 1993.

Heil et al., "Species-specific recognition of single-stranded RNA via Toll-like receptor 7 and 8", *Science*, vol. 303, pp. 1526-1529, 2004.

Herbert et al., "Lipid modification of GRN163, an N3'-P5' thio-phosphoramidate oligonucleotide enhances the potency telomerase inhibition", *Oncogene*, 24:5262-5268, 2005.

Herbert et al., *The Dictionary of Immunology*, Academic Press: San Diego, 4th ed. 1995. Print.

Heyman, "The immune complex: possible ways of regulating the antibody response", *Immunology Today*, 11(9):310-313, 1990.

Hoerr et al., "In vivo application of RNA leads to induction of specific cytotoxic T lymphocytes and antibodies", *Eur J Immunol.*, 30(1):1-7, 2000.

Huang et al., "Recent development of therapeutics for chronic HCV infection", *Antiviral Res.*, 71:351-362, 2006.

Huget et al., "Adjuvant and suppressor activity of the polycation protamine hydrochloride in the primary immune response of mice", *Z Immunitatsforsch Immunobiol.*, 152(3):190-9, 1976. (English Abstract).

Janssens et al., "Role of toll-like receptors in pathogen recognition", *Clinical Microbiology Reviews*, 16(4):637-646, 2003.

Kilk, "Cell-penetrating peptides and bioactive cargoes. Strategies and mechanisms," *Department of Neurochemistry and Neurotoxicology, Stockholm University*, Doctoral dissertation, 2004.

Kim et al.,"VeGF siRNA delivery system using arginine-grafted bioreducible poly(disulfide amine)", *Molecular Pharmaceutics*, 6(3):718-726, 2009.

Kovarik J. et al, "Optimization of vaccine responses in early life: the role of innate defense systems and immunomodulators," *Immunology and Cell Biology*, vol. 76, No. 3, pp. 222-236, Jun. 1998.

Koziel et al., "Hepatitis C virus (HCV)-specific cytotoxic T lymphocytes recognize epitopes in the core and envelope proteins of HCV", J Virol., 67(12):7522-32, 1993.

Kwiatkowski et al., "The 9-(4-Octadecyloxyphenylxanthen)-9-yl-Group. A new Acid-labile Hydroxyl Protective Group and Its Application in the Preparative Reverse-phase Chromatographic Separation of Oligoribonucleotides",*Acta Chemica Scandinavica*, 38b:657-671, 1984.

Kwok KY et al., "Formulation of highly soluble poly(ethylene glycol)-peptide DNA condensates," *J Pharm Sci.* ;88(10):996-1003, Oct. 1999.

Lo et al., "An endosomolytic Tat peptide produced by incorporation of histidine and cysteine residues as a nonviral vector for DNA transfection", *Biomaterials*, 29(15):2408-2414, 2008.

(56) References Cited

OTHER PUBLICATIONS

Lochmann et al., "Drug delivery of oligonucleotides by peptides," *European Journal of Pharmaceutics and Biopharmaceutics*; vol. 58, No. 2, pp. 237-251, 2004.
Martin M.E. et al., "Peptide-guided gene delivery," *AAPS J.* 9;9(1):E18-29. Review. Feb. 2007.
Mateo et al., "An HLA-A2 polyepitope vaccine for melanoma immunotheraphy", *J Immunol.*, 163:4058-4063, 1999.
Matray and Gryaznov., "Synthesis and properties of RNA analogs-oligoribonucleotide N3'-P5' phosphoramidates", *Nucleic Acids Research*, 27(20):3976-85, 1999.
Manner et al., "Vaccination with poly-L-arginine as immunostimulant for peptide vaccines: induction of potent and long-lasting T-cell responses against cancer antigens," *Cancer Research*, 62(5):1477-1480, 2002.
McKenzie et al., "A potent new class of reductively activated peptide gene delivery agents", *Journal of Biological Chemistry*, 275(14):9970-9977, 2000.
McKenzie et al., "Low molecular weight disulfide cross-linking peptides as nonviral gene discovery carriers", *Bioconjugate Chemistry*, 11(6):901-909, 2000.
Milich et al., "The hepatitis B virus core and e antigens elicit different Th cell subsets: antigen structure can affect Th cell phenotype", J Virol., 71(3):2192-201, 1997.
Minks et al., "Structural requirements of double-stranded RNA for the activation of 2',5'-oligo(A)polymerase and protein kinase of interferon-treated HeLa cells", *The Journal of Biological Chemistry*, 254(20):10180-10183, 1979.
Miyata et al., "Block catiomer polyplexes with regulated densities of charge and disulfide cross-linking directed to enhance gene expression", *Journal of the American Chemical Society*, 126(8):2355-2361, 2004.
Nakamura Yet al., "Octaarginine-modified multifunctional envelope-type nano device for siRNA," *J Control Release*. Jun. 22, 2007, 119(3):360-7. Epub Mar. 23, 2007.
Neu Met al., "Recent advances in rational gene transfer vector design based on poly( ethylene imine) and its derivatives," *J Gene Med.*, 7(8):992-1009, Aug. 2005.
Nicholson et al., "Accurate in vitro cleavage by RNase III of phosphorothioate-substituted RNA processing signals in bacteriophage T7 early mRNA", *Nucleic Acids Res.*, 16(4):1577-91, 1988.
Notice of Allowance issued in U.S. Appl. No. 13/378,241, dated Nov. 22, 2013.
Office Action issued in U.S. Appl. No. 13/203,653, dated Jul. 17, 2014.
Office Action issued in U.S. Appl. No. 13/203,653, dated Jan. 30, 2014.
Office Action issued in U.S. Appl. No. 13/378,241, dated Apr. 24, 2013.
Office Action issued in U.S. Appl. No. 13/378,241, dated Jan. 10, 2013.
Office Action issued in U.S. Appl. No. 14/195,864, dated Feb. 13, 2015.
Office Action issued in U.S. Appl. No. 14/195,864, dated Jul. 16, 2015.
Oupicky D. et al., "Importance of lateral and steric stabilization of polyelectrolyte gene delivery vectors for extended systemic circulation," *Mol Ther.*, 5(4):463-72, Apr. 2002.
Oupicky D. et al., "Laterally stabilized complexes of DNA with linear reducible polycations: strategy for triggered intracellular activation of DNA delivery vectors," *J Am Chem. Soc.*, 124(1):8-9, Soc., Jan. 9, 2002.
Parker A.L. et al., "Enhanced gene transfer activity of peptide-targeted gene-delivery vectors," *J Drug Target.*, 13(1):39-51, Jan. 2005.
Parkinson et al., "A transcriptomic analysis of the phylum Nematoda", *Nature Genetics*, 36(12):1259-1267, 2004.

Pichon C. et al., "Poly [Lys-(AEDTP)] : a cationic polymer that allows dissociation of pDNA/cationic polymer complexes in a reductive medium and enhances polyfection," *Bioconjug Chem.*, 13(1):76-82, Jan.-Feb. 2002.
Pomroy N.C. et al., "Solubilization of hydrophobic peptides by reversible cysteine PEGylation," Biochem Biophys Res Commun., 245(2):618-21, Apr. 17, 1998.
Racanelli et al., "Presentation of HCV antigens to naïve CD8+T cells: why the where, when, what and how are important for virus control and infection outcome", *Clin Immunol.*, 124(1):5-12, 2007.
Radu D.L. et al, "Plasmid expressing the influenza HA gene protects old mice from lethal challenge with influenza viraus," *Viral Immunology*, vol. 12, No. 3, pp. 217-226, 1999.
Ramazeilles et al., "Antisense phosphorothioate oligonucleotides: selective killing of the intracellular parasite *Leishmania amazonensis*", *Proc Natl Acad Sci USA*, 91(17):7859-63, 1994.
Read M.L. et al., "A versatile reducible polycation-based system for efficient delivery of a broad range of nucleic acids," *Nucleic Acids Res.*, 33(9):e86, May 24, 2005.
Read M.L. et al., "RNA-based therapeutic strategies for cancer," *Expert Opinion on Therapeutic Patents*, vol. 13, No. 5, pp. 627-638, 2003.
Read M.L. et al., "Vectors based on reducible polycations facilitate intracellular release of nucleic acids," *J Gene Med.*, 5(3):232-45. Mar. 2003.
Riedl et al., "Priming Th1 immunity to viral core particles is facilitated by trace amounts of RNA bound to its arginine-rich domain", *J Immunol.*, 168(10):4951-9, 2002.
Rittner et al., "New basic membrane-destabilizing peptides for plasmid-based gene delivery in Vitro and in Vivo," *Molecular Therapy*, 5(2)104-114, 2002.
Rollier et al., "Control of heterologous hepatitis C virus infection in chimpanzees is associated with the quality of vaccine-induced peripheral t-helper immune response", *J Virol.*, 78(1):187-196, 2004.
Romagne et al., "Current and future drugs targeting one class of innate immunity receptors: the toll-like receptors", *Drug Discov Today*, 12(1-2):80-7, 2007.
Rozenfeld et al., "Stable assemblies of cationic bilayer fragments and CpG oligonucleotide with enhanced immunoadjuvant activity in vivo", *Journal of Controlled Release*, 160(2):367-373, 2011.
Saenz-Badillos et al., "RNA as a tumor vaccine: a review of the literature", *Exp Dermatol.*, 10(3):143-154, 2001.
Sakae M. et al, "Highly efficient in vivo gene transfection by plasmid/PEI complexes coated by anionic PEG derivatives bearing carboxyl groups and RGD peptide," *Biomedicine and Pharmacotherapy*, vol. 62, No. 7, pp. 448-453, Sep. 1, 2008.
Scheel et al., "Therapeutic anti-tumor immunity triggered by injections of immunostimulating single-stranded RNA," *Eur J Immunol*, vol. 36, No. 10, pp. 2807-2816, 2006.
Scheel et al., "Toll-like receptor-dependent activation of several human blood cell types by protamine-condensed mRNA," *Eur J Imnunol*, vol. 35, No. 5, pp. 1557-1566, 2005.
Scheel et al., "Immunostimulating capacities of stabilized RNA molecules", *Eur J Immunol.*, 24:537-547, 2004.
Scheel et al., "mRNA as immunostimulatory molecule", Krebsimmuntherapie Annual Meeting, Oral Presentation May 9, 2003. (Abstract).
Schirrmacher et al., "Intra-pinna anti-tumor vaccinaton with self-replicating infectious RNA or with DNA encoding a model tumor antigen and a cytokine", *Gene Therapy*, 7(13):1137-1147, 2000.
Shea et al., "Synthesis, hybridization properties and antiviral activity of lipid-oligodeoxynucleotide conjugates", *Nucleic Acids Research*, 18(13):3777-3783, 1990.
Shiffman et al., "Protein dissociation from DNA in model systems and chromatin," *Nucleic Acids Res.*, 5(9):3409-3426, 1978.
Shirai et al., "An epitope in hepatitis C virus core region recognized by cytotoxic T cells in mice and humans",*J Virol.*, 68(5):3334-3342, 1994.
Stephens et al., "Sequence analysis of the major outer membrane protein gene from *Chlamydia trachomatis* serovar L2", *Journal of Bacteriology*, 168(3):1277-1282, 1986.

(56) References Cited

OTHER PUBLICATIONS

Sun et al., "Advances in saponin-based adjuvants," *Vaccine*, 27:1787-1796, 2009.
Takae S. et al., "PEG-detachable polyplex micelles based on disulfide-linked block catiomers as bioresponsive nonviral gene vectors," *J Am Chem Soc.*, 130(18):6001-9, May 7, 2008. Epub Apr. 9, 2008.
Tan et al., "Strategies for hepatitis C therapeutic intervention: now and next", *Curr Opin in Pharmacology*, 4:465-470, 2004.
Teplova et al., "Crystal structure and improved antisense properties of 2'-O-(2-methoxyethyl)-RNA", *Nature Structural Biology*, 6(6):535-539, 1999.
Tokunaga et al., "Effect of oligopeptides on gene expression: comparison of DNA/peptide and DNA/peptide/liposome complexes", *International Journal of Pharmaceutics*, 269(1):71-80, 2004.
Tönges L. et al., "Stearylated octaarginine and artificial virus-like particles for transfection of siRNA into primary rat neurons," *RNA*, 12(7):1431-8. Epub May 12, 2006.
Trinchieri et al., "Cooperation of toll-like receptor signals in innate immune defence", *Nature Reviews Immunology*, 7:179-190, 2007.
Tse et al., "Update on toll-like receptor-directed therapies for human disease", *Ann Rheum Dis.*, 66 Suppl 3:iii77-80, 2007.
Unnamalai N. et al., "Cationic oligopeptide-mediated delivery of dsRNA for posttranscriptional gene silencing in plant cells," *FEBS Lett.*, 566(1-3):307-10, May 21, 2004.
Vivès E. et al., "A truncated HIV-1 Tat protein basic domain rapidly translocates through the plasma membrane and accumulates in the cell nucleus," *J Biol Chem.*, 272(25):16010-7, Jun. 20, 1997.
Wang Y.H. et al., "An intracellular delivery method for siRNA by an arginine-rich peptide," *J Biochem Biophys Methods*, 70(4):579-86, Jun. 10, 2007. Epub Jan. 30, 2007.
Wyman et al., "Design, synthesis, and characterization of a cationic peptide that binds to nucleic acids and permeabilizes bilayers," *Biochemistry*, 36:3008-3017, 1997.
Xiong et al., "pH-responsive multi-PEGylated dual cationic nanoparticles enable charge modulations for safe gene delivery," *Chem Med Chem*, 2:1321-1327, 2007.
Yoshitomi et al., "Design of core-shell-type nanoparticles carrying stable radicals in the core," *Biomacromolecules*, 10:596-601, 2009.
Zhang et al., "Delivery of telomerase reverse transcriptase small interfering RNA in complex with positively charged single-walled carbon nanotubes suppresses tumor growth," *Clinical Cancer Research*, 12:4933-4939, 2006.
Zhou et al., "RNA melanoma vaccine: induction of antitumor immunity by human glycoprotein 100 mRNA immunization", *Human Gene Therapy*, 10:2719-2724, 1999.
Zimmermann et al., "Immunostimulatory DNA as adjuvant: efficacay of phosphodiester CpG oligonucleotides is enhanced by 3' sequence modifications", *Vaccine*, 21(9-10):990-5, 2003. (abstract only).
Zohra et al., "Effective delivery with enhanced translational activity synergistically accelerates mRNA-based transfection," *Biochem Biphys Res Commun.*, 358(1):373-378, 2007.
Andreu et al., "Formation of disulfide bonds in synethetic peptides and proteins," Chapter 7, *Methods in Molecular Biology*, vol. 35, Peptide Synthesis Protocols, Pennington and Dunn, 1994.
Hamm et al., "Immunostimulatory RNA is a potent inducer of antigen-specific cytotoxic and humoral immune response in vivo," *International Immunology*, 19(3):297-304, 2007.
Hwang et al., "A brain-targeted rabies virus glycoprotein-disulfide linked PEI nanocarrier for delivery of neurogenic microRNA," Biomaterials, 32:4968-4975, 2011.
Weide et al., "Direct injection of protamine-protected mRNA: results of a phase 1/2 vaccination trial in metastatic melanoma patients," *J Immunother.*, 32(5):498-507, 2009.
Zhao et al., "N/P ratio significantly influences the transfection efficiency and cytotoxicity of a polyethylenimine/chitosan/DNA complex," *Biol. Pharm. Bull.*, 32(4):706-710, 2009.

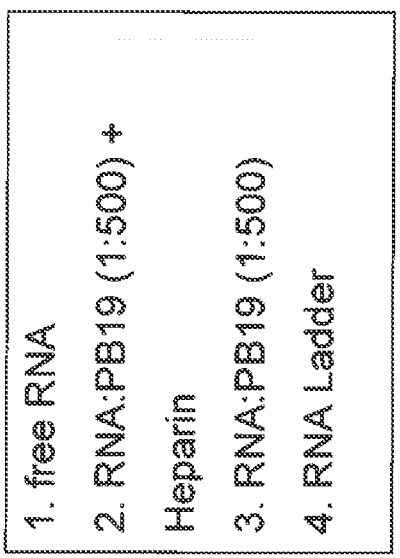
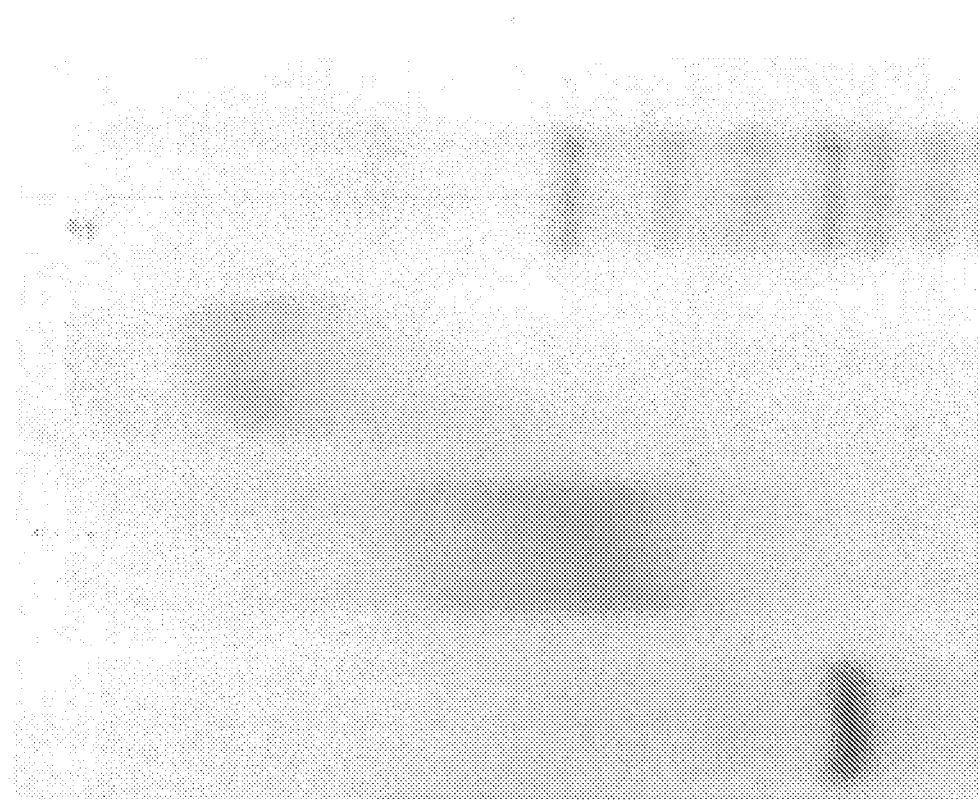
Figure 4

A
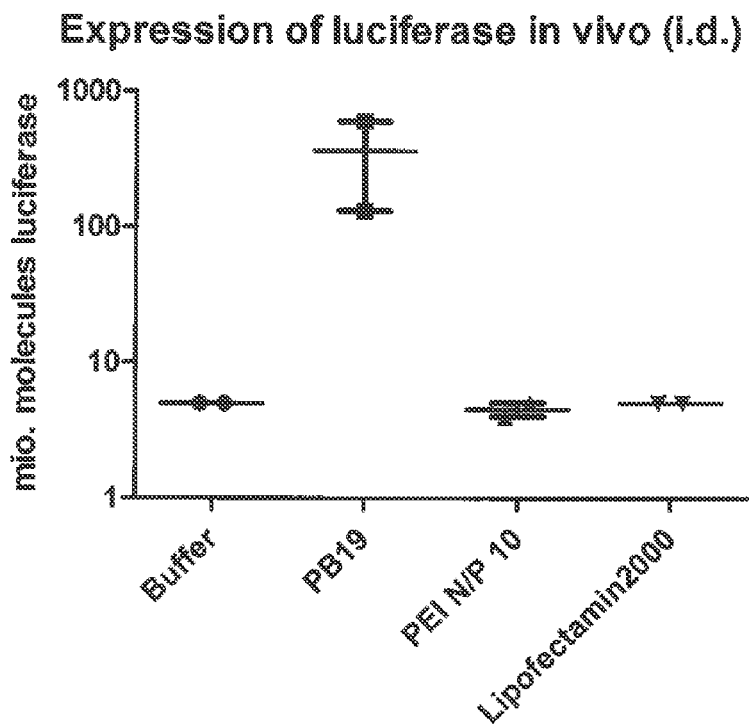
B
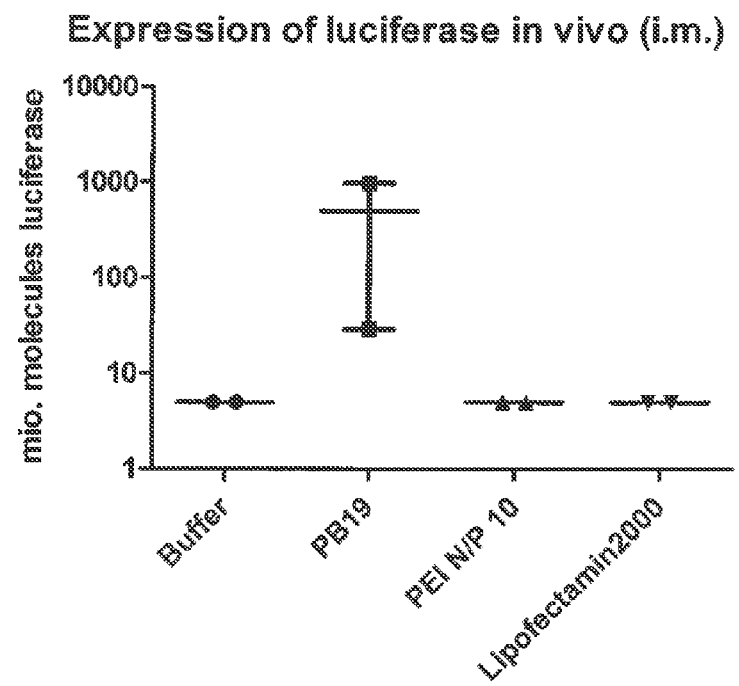
FIGS. 9A-B

```
   1  GGGAGAAAGC UUGAGGAUGG AGGACGCCAA GAACAUCAAG AAGGGCCCGG
  51  CGCCCUUCUA CCCGCUGGAG GACGGGACCG CCGGCGAGCA GCUCCACAAG
 101  GCCAUGAAGC GGUACGCCCU GGUGCCGGGC ACGAUCGCCU UCACCGACGC
 151  CCACAUCGAG GUCGACAUCA CCUACGCGGA GUACUUCGAG AUGAGCGUGC
 201  GCCUGGCCGA GGCCAUGAAG CGGUACGGCC UGAACACCAA CCACCGGAUC
 251  GUGGUGUGCU CGGAGAACAG CCUGCAGUUC UUCAUGCCGG UGCUGGGCGC
 301  CCUCUUCAUC GGCGUGGCCG UCGCCCCGGC GAACGACAUC UACAACGAGC
 351  GGGAGCUGCU GAACAGCAUG GGGAUCAGCC AGCCGACCGU GGUGUUCGUG
 401  AGCAAGAAGG GCCUGCAGAA GAUCCUGAAC GUGCAGAAGA AGCUGCCCAU
 451  CAUCCAGAAG AUCAUCAUCA UGGACAGCAA GACCGACUAC CAGGGCUUCC
 501  AGUCGAUGUA CACGUUCGUG ACCAGCCACC UCCCGCCGGG CUUCAACGAG
 551  UACGACUUCG UCCCGGAGAG CUUCGACCGG GACAAGACCA UCGCCCUGAU
 601  CAUGAACAGC AGCGGCAGCA CCGGCCUGCC GAAGGGGGUG GCCCUGCCGC
 651  ACCGGACCGC CUGCGUGCGC UUCUCGCACG CCCGGGACCC CAUCUUCGGC
 701  AACCAGAUCA UCCCGGACAC CGCCAUCCUG AGCGUGGUGC CGUUCCACCA
 751  CGGCUUCGGC AUGUUCACGA CCCUGGGCUA CCUCAUCUGC GGCUUCCGGG
 801  UGGUCCUGAU GUACCGGUUC GAGGAGGAGC UGUUCCUGCG GAGCCUGCAG
 851  GACUACAAGA UCCAGAGCGC GCUGCUCGUG CCGACCCUGU UCAGCUUCUU
 901  CGCCAAGAGC ACCCUGAUCG ACAAGUACGA CCUGUCGAAC CUGCACGAGA
 951  UCGCCAGCGG GGGCGCCCCG CUGAGCAAGG AGGUGGGCGA GGCCGUGGCC
1001  AAGCGGUUCC ACCUCCCGGG CAUCCGCCAG GGCUACGGCC UGACCGAGAC
1051  CACGAGCGCG AUCCUGAUCA CCCCCGAGGG GGACGACAAG CCGGGCGCCG
1101  UGGGCAAGGU GGUCCCGUUC UUCGAGGCCA AGGUGGUGGA CCUGGACACC
1151  GGCAAGACCC UGGGCGUGAA CCAGCGGGGC GAGCUGUGCG UGCGGGGGCC
1201  GAUGAUCAUG AGCGGCUACG UGAACAACCC GGAGGCCACC AACGCCCUCA
1251  UCGACAAGGA CGGCUGGCUG CACAGCGGCG ACAUCGCCUA CUGGGACGAG
1301  GACGAGCACU UCUUCAUCGU CGACCGGCUG AAGUCGCUGA UCAAGUACAA
1351  GGGCUACCAG GUGGCGCCGG CCGAGCUGGA GAGCAUCCUG CUCCAGCACC
1401  CCAACAUCUU CGACGCCGGC GUGGCCGGGC UGCCGGACGA CGACGCCGGC
1451  GAGCUGCCGG CCGCGGUGGU GGUGCUGGAG CACGGCAAGA CCAUGACGGA
1501  GAAGGAGAUC GUCGACUACG UGGCCAGCCA GGUGACCACC GCCAAGAAGC
1551  UGCGGGGCGG CGUGGUGUUC GUGGACGAGG UCCCGAAGGG CCUGACCGGG
1601  AAGCUCGACG CCCGGAAGAU CCGCGAGAUC CUGAUCAAGG CCAAGAAGGG
1651  CGGCAAGAUC GCCGUGUAAG ACUAGUUAUA AGACUGACUA GCCCGAUGGG
1701  CCUCCCAACG GGCCCUCCUC CCUCCUUGC  ACCGAGAUUA AUAAAAAAAA
1751  AAAAAAAAAA AAAAAAAAAA AAAAAAAAAA AAAAAAAAAA AAAAAAAAAA
1801  AAAAAUAUU  CCCCCCCCC  CCCCCCCCC  CCCCCCCCC  UCUAGACAAU
1851  UGGAAUU
```

Figure 16

DISULFIDE-LINKED POLYETHYLENEGLYCOL/PEPTIDE CONJUGATES FOR THE TRANSFECTION OF NUCLEIC ACIDS

This application is a continuation of U.S. application Ser. No. 14/195,864, filed Mar. 4, 2014, which is a continuation of U.S. application Ser. No. 13/378,241, filed May 11, 2012, now U.S. Pat. No. 8,703,906, which is a national phase application under 35 U.S.C. § 371 of International Application No. PCT/EP2010/005438, filed Sep. 3, 2010, which was a continuation-in-part of U.S. application Ser. No. 12/553,559, filed Sep. 3, 2009, now abandoned. The entire text of each of the above referenced disclosures is specifically incorporated herein by reference.

The present invention is directed to an inventive polymeric carrier molecule according to generic formula (I) and variations thereof, which allows for efficient transfection of nucleic acids into cells in vivo and in vitro, a polymeric carrier cargo complex formed by a nucleic acid and the inventive polymeric carrier molecule, but also to methods of preparation of this inventive polymeric carrier molecule and of the inventive polymeric carrier cargo complex. The present invention also provides methods of application and use of this inventive polymeric carrier molecule and the inventive polymeric carrier cargo complex as a medicament, for the treatment of various diseases, and in the preparation of a pharmaceutical composition for the treatment of such diseases.

Various diseases today require a treatment which involves administration of peptide-, protein-, and nucleic acid-based drugs, particularly the transfection of nucleic acids into cells or tissues. The full therapeutic potential of peptide-, protein-, and nucleic acid-based drugs is frequently compromised by their limited ability to cross the plasma membrane of mammalian cells, resulting in poor cellular access and inadequate therapeutic efficacy. Today this hurdle represents a major challenge for the biomedical development and commercial success of many biopharmaceuticals (see e.g. Foerg and Merkle, Journal of Pharmaceutical Sciences, published online at www.interscience.wiley.com, 2008, 97(1): 144-62).

For some diseases or disorders, gene therapeutic approaches have been developed as a specific form of such treatments. These treatments in general utilize transfection of nucleic acids or genes into cells or tissues, whereas gene therapeutic approaches additionally involve the insertion of one or more of these nucleic acids or genes into an individual's cells and tissues to treat a disease, e.g. hereditary diseases, in which a defective mutant allele is replaced with a functional one.

Transfer or insertion of one or more of these nucleic acids or genes into an individual's cells, however, still represents a major challenge today and is absolutely necessary for ensuring a good therapeutical effect of a nucleic acid based medicaments, particularly in the field of gene therapy.

To achieve successful transfer of nucleic acids or genes into an individual's cells, a number of different hurdles have to be passed. The transport of nucleic acids typically occurs via association of the nucleic acid with the cell membrane and subsequent uptake by the endosomes. In the endosomes, the introduced nucleic acids are separated from the cytosol. As expression occurs in the cytosol, these nucleic acids have to depart the cytosol. If the nucleic acids do not manage departing the cytosol, either the endosome fuses with the lysosome leading to a degradation of its content, or the endosome fuses with the cell membrane leading to a return of its content into the extracellular medium. For efficient transfer of nucleic acids, the endosomal escape thus appears to be one of the most important steps additional to the efficiency of transfection itself. Until now, there are different approaches addressing these issues. However, no approach was at least successful in all aspects.

Transfection agents used in the art today typically comprise peptides, different polymers, lipids as well as nano- and microparticles (see e.g. Gao, X., K. S. Kim, et al. (2007), Aaps J 9(1): E92-104). These transfection agents typically have been used successfully only in in vitro reactions. When transfecting nucleic acids in vivo into cells of a living animal, further requirements have to be fulfilled. As an example, the complex has to be stable in physiological salt solutions with respect to agglomerisation. Furthermore, it does not interact with parts of the complement system of the host. Additionally, the complex shall protect the nucleic acid from early extracellular degradation by ubiquitously occurring nucleases. For genetherapeutic applications it is furthermore of utmost importance, that the carrier is not recognized by the adaptive immune system (immunogenicity) and does not stimulate an unspecific cytokine storm (acute immune response) (see Gao, Kim et al., (2007, supra); Martin, M. E. and K. G. Rice (2007), Aaps J 9(1): E18-29; and Foerg and Merkle, (2008, supra)). Foerg and Merkle (2008, supra), discuss therapeutic potential of peptide-, protein- and nucleic acid-based drugs. According to their analysis, the full therapeutic potential of these drugs is frequently compromised by their limited ability to cross the plasma membrane of mammalian cells, resulting in poor cellular access and inadequate therapeutic efficacy. Today this hurdle represents a major challenge for the biomedical development and commercial success of many biopharmaceuticals.

In this context, Gao et al. (Gao et al. The AAPS Journal 2007; 9(1) Article 9) see the primary challenge for gene therapy in the development of a method that delivers a therapeutic gene to selected cells where proper gene expression can be achieved. Gene delivery and particularly successful transfection of nucleic acids into cells or tissue is, however, not simple and typically dependent on many factors. For successful delivery, e.g., delivery of nucleic acids or genes into cells or tissue, many barriers must be overcome. According to Gao et al. (2007) an ideal gene delivery method needs to meet 3 major criteria: (1) it should protect the transgene against degradation by nucleases in intercellular matrices, (2) it should bring the transgene across the plasma membrane and (3) it should have no detrimental effects.

These goals may be achieved by using a combination of different compounds or vectors. Notably, there are some compounds or vectors, which overcome at least some of these barriers.

Most usually, transfection, e.g. of nucleic acids, is carried out using viral or non-viral vectors. For successful delivery, these viral or non-viral vectors must be able to overcome the above mentioned barriers. The most successful gene therapy strategies available today rely on the use of viral vectors, such as adenoviruses, adeno-associated viruses, retroviruses, and herpes viruses. Viral vectors are able to mediate gene transfer with high efficiency and the possibility of long-term gene expression, and satisfy 2 out of 3 criteria. However, the acute immune response, immunogenicity, and insertion mutagenesis uncovered in gene therapy clinical trials have raised serious safety concerns about some commonly used viral vectors.

A solution to this problem may be found in the use of non-viral vectors. Although non-viral vectors are not as efficient as viral vectors, many non-viral vectors have been developed to provide a safer alternative in gene therapy. Methods of nonviral gene delivery have been explored using physical (carrier-free gene delivery) and chemical approaches (synthetic vector-based gene delivery). Physical approaches usually include needle injection, electroporation, gene gun, ultrasound, and hydrodynamic delivery, employ a physical force that permeates the cell membrane and facilitates intracellular gene transfer. The chemical approaches typically use synthetic or naturally occurring compounds (cationic lipids, cationic polymers, lipid-polymer hybrid systems) as carriers to deliver the transgene into cells. Although significant progress has been made in the basic science and applications of various nonviral gene delivery systems, the majority of nonviral approaches is still much less efficient than viral vectors, especially for in vivo gene delivery (see e.g. Gao et al. The AAPS Journal 2007; 9(1) Article 9).

Over the past decade, attractive prospects for a substantial improvement in the cellular delivery of nucleic acids have been announced that were supposed to result from their physical assembly or chemical ligation to so-called cell penetrating peptides (CPPs) also denoted as protein-transduction domains (PTDs) (see Foerg and Merkle, (2008, supra)). CPPs represent short peptide sequences of 10 to about 30 amino acids which can cross the plasma membrane of mammalian cells and may thus offer unprecedented opportunities for cellular drug delivery. Nearly all of these peptides comprise a series of cationic amino acids in combination with a sequence, which forms an α-helix at low pH. As the pH is continuously lowered in vivo by proton pumps, a conformational change of the peptide is usually initiated rapidly. This helix motif mediates an insertion into the membrane of the endosome leading to a release of its content into the cytoplasma (see Foerg and Merkle, (2008, supra); and Vives, E., P. Brodin, et al. (1997). "A truncated HIV-1 Tat protein basic domain rapidly translocates through the plasma membrane and accumulates in the cell nucleus." J Biol Chem 272(25): 16010-7). Despite these advantages, a major obstacle to CPP mediated drug delivery is thought to consist in the often rapid metabolic clearance of the peptides when in contact or passing the enzymatic barriers of epithelia and endothelia. In conclusion, metabolic stability of CPPs represents an important biopharmaceutical factor for their cellular bioavailability. However, there are no CPPs available in the art, which are on the one hand side stable enough to carry their cargo to the target before they are metabolically cleaved, and which on the other hand side can be cleared from the tissue before they can accumulate and reach toxic levels.

One further approach in the art for delivering cargo molecules into cells, e.g. for gene therapy, comprises peptide ligands (see Martin and Rice (see Martin and Rice, The AAPS Journal 2007; 9 (1) Article 3)). Peptide ligands can be short sequences taken from larger proteins that represent the essential amino acids needed for receptor recognition, such as EGF peptide used to target cancer cells. Other peptide ligands have been identified including the ligands used to target the lectin-like oxidized LDL receptor (LOX-1). Up-regulation of LOX-1 in endothelial cells is associated with dysfunctional states such as hypertension and atherosclerosis. Such peptide ligands, however, are not suitable for many gene therapeutic approaches, as they cannot be linked to their cargo molecules by complexation or adhesion but require covalent bonds, e.g. crosslinkers, which typically exhibit cytotoxic effects in the cell.

Synthetic vectors may also be used in the art for delivering cargo molecules into cells, e.g., for the purpose of gene therapy. However, one main disadvantage of many synthetic vectors is their poor transfection efficiency compared to viral vectors and significant improvements are required to enable further clinical development. Several barriers that limit nucleic acid transfer both in vitro and in vivo have been identified, and include poor intracellular delivery, toxicity and instability of vectors in physiological conditions (see. e.g. Read, M. L., K. H. Bremner, et al. (2003). "Vectors based on reducible polycations facilitate intracellular release of nucleic acids." J Gene Med 5(3): 232-45).

One specific approach in gene therapy uses cationic lipids. However, although many cationic lipids show excellent transfection activity in cell culture, most do not perform well in the presence of serum, and only a few are active in vivo. A dramatic change in size, surface charge, and lipid composition occurs when lipoplexes are exposed to the overwhelming amount of negatively charged and often amphipatic proteins and polysaccharides that are present in blood, mucus epithelial lining fluid, or tissue matrix. Once administered in vivo, lipoplexes tend to interact with negatively charged blood components and form large aggregates that could be absorbed onto the surface of circulating red blood cells, trapped in a thick mucus layer or embolized in microvasculatures, preventing them from reaching the intended target cells in the distal location. Furthermore, toxicity related to gene transfer by lipoplexes has been observed. Symptoms include inter alia induction of inflammatory cyokines. In humans, various degrees of adverse inflammatory reactions, including flu-like symptoms were noted among subjects who received lipoplexes. Accordingly, it appears questionable, as to whether lipoplexes can be safely used in humans at all.

One further, more promising approach in gene therapy utilizes cationic polymers. Cationic polymers turned out to be efficient in transfection of nucleic acids, as they can tightly complex and condense a negatively charged nucleic acid. Thus, a number of cationic polymers have been explored as carriers for in vitro and in vivo gene delivery. These include polyethylenimine (PEI), polyamidoamine and polypropylamine dendrimers, polyallylamine, cationic dextran, chitosan, cationic proteins and cationic peptides. Although most cationic polymers share the function of condensing DNA into small particles and facilitating cellular uptake via endocytosis through charge-charge interaction with anionic sites on cell surfaces, their transfection activity and toxicity differ dramatically. Interestingly, cationic polymers exhibit better transfection efficiency with rising molecular weight due to stronger complexation of the negatively charged nucleic acid cargo. However, a rising molecular weight also leads to a rising toxicity of the cationic polymer. PEI is perhaps the most active and most studied polymer for gene delivery, but its main drawback as a transfection reagent relates to its non-biodegradable nature and toxicity. Furthermore, even though polyplexes formed by high molecular weight polymers exhibit improved stability under physiological conditions, data have indicated that such polymers can hinder vector unpacking. For example, poly (L-lysine) (PLL) of 19 and 36 residues was shown to dissociate from DNA more rapidly than PLL of 180 residues resulting in significantly enhanced short-term gene expression. A minimum length of six to eight cationic amino acids is required to compact DNA into structures active in receptor-mediated gene delivery. However, polyplexes formed with short polycations are unstable under physiological conditions and typically aggregate rapidly in physiological salt solutions. To overcome this negative impact, Read et al. (see Read, M. L., K. H. Bremner, et al. (2003). "Vectors based on reducible polycations facilitate intracellular release of nucleic acids." J Gene Med 5(3): 232-45; and Read, M. L., S. Singh, et al. (2005). "A versatile reducible polycation-based system for efficient delivery of a broad range of nucleic acids." Nucleic Acids Res 33(9): e86) developed a new type of synthetic vector based on a linear reducible polycation (RPC) prepared by oxidative polycondensation of the peptide Cys-Lys$_{10}$-Cys that can be cleaved by the intracellular environment to facilitate release of nucleic acids. They could show that polyplexes formed by RPC are destabilised by reducing conditions enabling efficient release of DNA and mRNA. Cleavage of the RPC also reduced toxicity of the polycation to levels comparable with low molecular weight peptides. The disadvantage of this approach of Read et al. (2003, supra) was that the endosomolytic agent chloroquine or the cationic lipid DOTAP was additionally necessary to enhance transfection efficiency to adequate levels. As a consequence Read et al. (2005, supra) included histidine residues in the RPCs which have a known endosomal buffering capacity. They could show that histidine-rich RPCs can be cleaved by the intracellular reducing environment enabling efficient cytoplasmic delivery of a broad range of nucleic acids, including plasmid DNA, mRNA and siRNA molecules without the requirement for the endosomolytic agent chloroquine.

Unfortunately; Read et al. (2005, supra) did not assess whether histidine-rich RPCs can be directly used for in vivo applications. In their study, transfections were performed in the absence of serum to avoid masking the ability of histidine residues to enhance gene transfer that may have arisen from binding of serum proteins to polyplexes restricting cellular uptake. Preliminary experiments indicate that the transfection properties of histidine-rich RPC polyplexes can be affected by the presence of serum proteins with a 50% decrease in GFP-positive cells observed in 10% FCS (fetal calf serum). For in vivo application they propose modifications with the hydrophilic polymer poly-[N-(2 hydroxypropyl)methacrylamide]. Unfortunately, Read et al. (2005, supra) did not prevent aggregation of polyplexes and binding of polycationic proteins to serum proteins. Furthermore, due to the large excess of polymer, which is characterized by the high N/P ratio, strong cationic complexes are formed when complexing the nucleic acid, which are only of limited use in vivo due to their strong tendency of salt induced agglomeration and interactions with serum contents (opsonization). Additionally, these complexes may excite an acute immune response, when used for purposes of gene therapy. Read et al. (2003, supra) did also not provide in vivo data for the RPC based complexes shown in the publication. It has also turned out that these strong cationic RPC based complexes are completely inactive subsequent to local administration into the dermis. Furthermore Read et al. (2005, supra) used stringent oxidation conditions (30% DMSO) to induce the generation of high molecular polymers with as long as possible chain lengths ("step-growth polymerization") to ensure complete complexation of the nucleic acid cargo.

In an approach similar to Read et al., McKenzie et al. (McKenzie, D. L., K. Y. Kwok, et al. (2000), J Biol Chem 275(14): 9970-7., McKenzie, D. L., E. Smiley, et al. (2000), Bioconjug Chem 11(6): 901-9, and U.S. Pat. No. 6,770,740 B1) developed self-crosslinking peptides as gene delivery agents by inserting multiple cysteines into short synthetic peptides for the purpose of decreasing toxicity as observed with high-molecular polycations. For complexation of DNA they mixed the self-crosslinking peptides with DNA to induce interpeptide disulfide bonds concurrently to complexation of the DNA cargo. For in vivo gene delivery approaches they propose the derivatization of the self-crosslinking peptides with a stealthing (e.g. polyethylene glycol) or targeting agent operatively attached to the peptide at a site distal from each terminus. In a further approach the same authors developed for the purpose of masking DNA peptide condensates and thereby reducing interaction with blood components, the derivatization of the non crosslinking cationic peptide CWK$_{18}$ with polyethylene glycol by reducible or non-reducible linkages (Kwok, K. Y., D. L. McKenzie, et al. (1999). "Formulation of highly soluble polyethylene glycol)-peptide DNA condensates." J Pharm Sci 88(10): 996-1003).

Summarizing the above, the present prior art as exemplified above suffers from various disadvantages, One particular disadvantage of the self-crosslinking peptides as described by Read et al. (2003, supra) or McKenzie et al. (2000 I and II, supra and U.S. Pat. No. 6,770,740 B1) concerns the high positive charge on the surface of the particles formed. Due to the high positive charge the particles exhibit a high instability towards agglomeration when subjecting these particles in vivo to raised salt concentrations. Such salt concentrations, however, typically occur in vivo in cells or extracellular media. Furthermore, high positively charged complexes show a strong tendency of opsonization. This leads to an enhanced uptake by macrophages and furthermore to a fast inactivation of the complex due to degradation. Particularly the uptake of these complexes by cells of the immune system in general leads to a downstream stimulation of different cytokines. This unspecific activation of the innate immune system, however, represents a severe disadvantage of these systems and should be avoided, particularly for the purpose of several aspects of gene therapy, where an acute immune response (cytokine storm) is strictly to be avoided. Additionally, in biological systems positively charged complexes can easily be bound or immobilized by negatively charged components of the extracellular matrix or the serum. Also, the nucleic acids in the complex may be released too early, leading to reduced efficiency of the transfer and half life of the complexes in vivo. Furthermore, a reversible derivatization of carriers with a stealthing agent being advantageous for in vivo gene delivery, such as polyethylene glycol (PEG), was only possible for peptide monomers but not for self-crosslinking peptides or rather for a polymeric carrier with a defined polymer chain length. In particular, such a reversible derivatization was not possible at the terminal ends of the crosslinked cationic peptide carrier. Additionally, in the prior art only high-molecular polymers with long polymer chains or with an undefined polymer chain length consisting of self-crosslinking peptides were described, which unfortunately compact their cargo to such an extent that cargo release in the cell is limited. The extremely undefined polymer chain length is further problematic regarding approvement of a medicament based on RPC. One precondition for an approvement of a medicament is that every preparation of the medicament has always the same composition, the same structure and the same properties. This cannot be ensured for complexes based on RFC's from the prior art. Furthermore the RPC-based polymers or complexes provided in the prior art are difficult to characterize due to their undefined structure or polymer chain length. But characterization of the resulting complex or of the polymeric carrier is absolutely necessary for the approvement of a medicament.

In consequence, no feasible method or carrier has been presented until today, which allows both compacting and stabilizing a nucleic acid for the purposes of gene therapy and other therapeutic applications, which show a good transfection activity in combination with a good release of the nucleic acid cargo, particularly in vivo and low or even no toxicity, e.g. due to the combination of a reversible stealthing and a reversible complexation of the nucleic acid by self-crosslinking polymers. Accordingly, there is still an intensive need in the art to provide carriers for the purpose of gene transfer, which are on the one hand side stable enough to carry their cargo to the target before they are metabolically cleaved, and which on the other hand side can be cleared from the tissue before they can accumulate and reach toxic levels.

The object underlying the present invention is therefore to provide a carrier or a complexing agent, particularly for the transfection of nucleic acids for the purposes of gene therapy or other therapeutic applications, which is capable to compact nucleic acids, preferably coding DNA or coding RNA, such as mRNA, and which allows efficient transfection of the nucleic acid into different cell lines in vitro but also transfection in vivo. As uptake by cells occurs via the endosomal route, such a carrier or a complexing agent shall also allow or provide for efficient release of the nucleic acid. Additionally, it is preferred, that the inventive polymeric carrier cargo complex formed by the nucleic acid cargo and such carrier or a complexing agent shows improved resistance to agglomeration. It should preferably also confer enhanced stability to the nucleic acid cargo with respect to serum containing media. Most importantly, in vivo activity shall be obtained, thereby suppressing at least in part an acute immune reaction. Furthermore a reproducible production and a characterization of the carrier should be assured.

This object is solved by the subject matter of the present invention, preferably by the subject matter of the attached claims. Particularly, according to the first embodiment of the present invention the above object is solved by a polymeric carrier molecule according to generic formula (I):

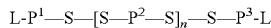

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with $(AA)_x$, or $[(AA)_x]_z$ if such components are used as a linker between $P^1$ and $P^2$ or $P^3$ and $P^2$) and/or with further components (e.g. $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy) ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20;

is a cationic or polycationic polymer, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. $(AA)_x$, or $[(AA)_x]_z$)

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, $(AA)_x$, $[(AA)_x]_z$, etc.); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc.), small molecules (e.g. carbohydrates like mannose or galctose or synthetic ligands), small molecule agonists, inhibitors or antagonists of receptors (e.g. RGD peptidomimetic analogues) etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

The inventive polymeric carrier molecule according to generic formula (I) is prepared by a new synthesis strategy and advantageously allows to define the length of the polymer chain and to combine desired properties of different (short) polymers in one polymer, e.g. to efficiently compact nucleic acids for the purpose of efficient transfection of nucleic acids for the purposes of gene therapy or other therapeutic applications without loss of activity, particularly efficient transfection of a nucleic acid into different cell lines in vitro but also transfection in vivo. The inventive polymeric carrier molecule is furthermore not toxic to cells and provides for efficient release of its nucleic acid cargo. Finally, it shows improved resistance to agglomeration due to the reversible addition of hydrophilic polymer chains (e.g. PEG-monomers) particularly to the terminal ends of the inventive polymeric carrier molecule according to generic formula (I), which additionally confers enhanced stability of the nucleic acid cargo with respect to serum containing media and prevents recognition of the polymeric carrier cargo complex by the immune system.

Even more advantageously, the inventive polymeric carrier molecule according to generic formula (I) allows to considerably vary its peptide or polymeric content and thus to modulate its biophysical/biochemical properties, particularly the cationic properties of component $[S-P^2-S]_n$, quite easily and fast, e.g. by incorporating as components $P^2$ the same or different cationic peptide(s), protein(s) or polymer(s) and optionally adding other components, e.g. amino acid component(s) $(AA)_x$, into the repetitive component $[S-P^2-S]$ to form a modified repetitive component such as $\{[S-P^2-S]_a/[S-(AA)_x-S]_b\}$ as a core motif of the inventive polymeric carrier (wherein a+b=n, see below). Even though consisting of quite small non-toxic monomer units the inventive polymeric carrier molecule forms a cationic binding sequence with a defined chain length providing a strong condensation of the nucleic acid cargo and complex stability. Under the reducing conditions of the cytosole (e.g. cytosolic GSH), the complex is rapidly degraded into its monomers, which are further degraded (e.g. oligopeptides) or secreted (e.g. PEG). This supports deliberation of the nucleic acid cargo in the cytosol. Due to degradation into small oligopeptides in the cytosole, no toxicity is observed as known for high-molecular oligopeptides, e.g. from high-molecular oligoarginine. The PEG-"coating" also allows to somehow "coat" the polymeric carrier with a hydrophilic coating at its terminal ends, which prevents salt-mediated agglomeration and undesired interactions with serum contents. In the cytosole, this "coating" is easily removed under the reducing conditions of the cell. Also, this effect promotes deliberation of the nucleic acid cargo in the cytosol.

As defined above, ligands (L), may be optionally used in the inventive polymeric carrier molecule according to generic formula (I), e.g. for direction of the inventive carrier polymer and its complexed nucleic acid into specific cells. They may be selected independent from the other from RGD, Transferrin, Folate, a signal peptide or signal sequence, a localization signal or sequence, a nuclear localization signal or sequence (NLS), an antibody, a cell penetrating peptide, (e.g. TAT), a ligand of a receptor (e.g. cytokines, hormones, growth factors etc.), small molecules (e.g. carbohydrates like mannose or galctose or synthetic ligands), small molecule agonists, inhibitors or antagonists of receptors (e.g. RGD peptidomimetic analogues) etc. Particularly preferred in this context is mannose as ligand to target antigen presenting cells which carries on their cell membrane mannose receptors. In a further preferred aspect of the first embodiment of the present invention galactose as optional ligand can be used to target hepatocytes. Such ligands may be attached to component $P^1$ and/or $P^3$ by reversible disulfide bonds as defined below or by any other possible chemical attachment, e.g. by amide formation (e.g. carboxylic acids, sulphonic acids, amines, etc.), by Michael addition (e.g. maleinimide moieties, α,β unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components.

In the context of formula (I) of the present invention components $P^1$ and $P^3$ represent a linear or branched hydrophilic polymer chain, containing at least one —SH-moiety, each $P^1$ and $P^3$ independently selected from each other, e.g. from polyethylene glycol (PEG), poly-N-(2-hydroxypropyl) methacrylamide, poly-2-(methacryloyloxy)ethyl phosphorylcholines, poly(hydroxyalkyl L-asparagine) or poly(hydroxyalkyl L-glutamine). $P^1$ and $P^3$ may be identical or different to each other. Preferably, each of hydrophilic polymers $P^1$ and $P^3$ exhibits a molecular weight of about 1 kDa to about 100 kDa, preferably of about 1 kDa to about 75 kDa, more preferably of about 5 kDa to about 50 kDa, even more preferably of about 5 kDa to about 25 kDa. Additionally, each of hydrophilic polymers $P^1$ and $P^3$ typically exhibits at least one —SH-moiety, wherein the at least one —SH-moiety is capable to form a disulfide linkage upon condensation with component $P^2$ or with component $(AA)_x$, if used as linker between $P^1$ and $P^2$ or $P^3$ and $P^2$ as defined below and optionally with a further component, e.g. L and/or $(AA)_x$, e.g. if two or more —SH-moieties are contained. The following subformulas "$P^1-S-S-P^2$" and "$P^2-S-S-P^3$" of generic formula (I) above (the brackets are omitted for better readability), wherein any of S, $P^1$ and $P^3$ are as defined herein, typically represent a situation, wherein one —SH-moiety of hydrophilic polymers $P^1$ and $P^3$ was condensed with one —SH-moiety of component $P^2$ of generic formula (I) above, wherein both sulphurs of these —SH-moieties form a disulfide bond S—S— as defined herein in formula (I). These —SH-moieties are typically provided by each of the hydrophilic polymers $P^1$ and $P^3$, e.g. via an internal cysteine or any further (modified) amino acid or compound which carries a —SH moiety. Accordingly, the subformulas "$P^1-S-S-P^2$" and "$P^2-S-S-P^3$" may also be written as "$P^1$-Cys-Cys-$P^2$" and "$P^2$-Cys-Cys-$P^3$", if the —SH-moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulfur of the —SH-moiety of cysteine. Likewise, the terms "—S-Cys" and "—Cys-S" indicate a disulfide bond between a —SH containing moiety and a cysteine, which may also be written as "—S—(S—Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (I) according to the present invention via chemical reactions or binding of compounds, e.g. by binding of a 3-thio propionic acid or thioimolane, by amide formation (e.g. carboxylic acids, sulphonic acids, amines, etc.), by Michael addition (e.g. maleinimide moieties, α,β unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the —SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, e.g. a ligand, an amino acid component $(AA)_x$, antibodies, cell penetrating peptides (e.g. TAT), etc.

According to a further preferred aspect of the first embodiment of the present invention, each of hydrophilic polymers $P^1$ and $P^3$ may also contain at least one further functional moiety, which allows attaching further components as defined herein, e.g. a ligand, an amino acid component $(AA)_x$, etc. Such functional moieties may be selected from functionalities which allow the attachment of further components, e.g. functionalities as defined herein, e.g. by amide formation (e.g. carboxylic acids, sulphonic acids, amines, etc.), by Michael addition (e.g. maleinimide moieties, $\alpha,\beta$ unsatured carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components.

Component $P^2$ in the context of formula (I) of the present invention preferably represents a cationic or polycationic peptide or protein or alternatively a cationic or polycationic polymer. Each component $P^2$ typically exhibits at least two —SH-moieties, capable to form a disulfide linkage upon condensation with further components $P^2$, component(s) $P^1$ and/or $P^3$ or alternatively with further components, e.g. amino acid components $(AA)_x$. Component $P^2$ typically occurs within the repetitive component $[—S—P^2—S—]_n$ of formula (I) of the present invention. The term "cationic or polycationic" typically refers to a charged molecule, which is positively charged (cation) at a pH value of about 1 to 9, preferably 4 to 9, 5 to 8 or even 6 to 8, more preferably of a pH value of or below 9, of or below 8, of or below 7, most preferably at physiological pH values, e.g. about 7.3 to 7.4. Accordingly, a cationic or polycationic peptide or protein as component $P^2$ or alternatively a cationic or polycationic polymer as component $P^2$ according to the present invention is positively charged under physiological conditions, particularly under physiological salt conditions of the cell in viva In the specific case that component $P^2$ of formula (I) of the present invention is a cationic or polycationic peptide or protein the cationic properties of component $[S—P^2—S]_n$ or $\{[S—P^2—S]_a/[S-(AA)_x-S]_b\}$ (as defined below) may be determined upon its content of cationic amino acids in the entire component $[S—P^2—S]_n$ or $\{[S—P^2—S]_a/[S-(AA)_x-S]_b\}$. Preferably, the content of cationic amino acids in component $[S—P^2—S]_n$ or $\{[S—P^2—S]_a/[S-(AA)_x-S]_b\}$ is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the entire component $[S—P^2—S]_n$ or $\{[S—P^2—S]_a/[S-(AA)_x-S]_b\}$ is 100%.

In the specific case that component $P^2$ of formula (I) of the present invention is a cationic or polycationic polymer the cationic properties of component $[S—P^2—S]_n$ or $\{[S—P^2—S]_a/[S-(AA)_x-S]_b\}$ may be determined upon its content of cationic charges in the entire component $[S—P^2—S]_n$ or $\{[S—P^2—S]_a/[S-(AA)_x-S]_b\}$ when compared to the overall charges of component $[S—P^2—S]_n$ or $\{[S—P^2—S]_a/[S-(AA)_x-S]_b\}$. Preferably, the content of cationic charges in component $[S—P^2—S]_n$ or $\{[S—P^2—S]_a/[S-(AA)_x-S]_b\}$ at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even preferably in the range of about 20% to 50%, e.g. 20, 30, 40 or 50%, or in a range formed by any two of the afore mentioned values, provided, that the content of all charges, e.g. positive and negative charges at a (physiological) pH as defined herein, in the entire component $[S—P^2—S]_n$ or $\{[S—P^2—S]_a/[S-(AA)_x-S]_b\}$ is 100%.

In the specific context of the inventive polymeric carrier cargo complex formed by the nucleic acid cargo and a polymeric carrier molecule according to generic formula (I) $L-P^1—S—[S—P^2—S]_n—S—P^3-L$ as defined herein (or according to any of its subformulas herein) it is particularly preferred that at least 10% of all charges in the whole repetitive component $[S—P^2—S]_n$ or $\{[S—P^2—S]_a/[S-(AA)_x-S]_b\}$ are cationic to allow complexation of the negatively charged nucleic acid cargo.

The cationic or polycationic peptide or protein as component $P^2$, or the cationic or polycationic polymer as component $P^2$, is preferably a linear molecule, however, branched cationic or polycationic peptides or proteins as component $P^2$ or branched cationic or polycationic polymers as component $P^2$ may also be used.

Typically, component $P^2$, e.g. the cationic or polycationic peptide or protein or the cationic or polycationic polymer as defined herein, is linked to its neighboring components, e.g. components $P^1$ and $P^3$, and/or as a part of repetitive component $[S—P^2—S]_n$ to further components $P^2$, via disulfide bonds (—S—S—) or to $(AA)_x$ components as part of $\{[S—P^2—S]_a/[S-(AA)_x-S]_b\}$. In this context, the sulfurs adjacent to component $P^2$ in the repetitive component $[S—P^2—S]_n$ and as defined in generic formula (I) $L-P^1—S—[S—P^2—S]_n—S—P^3-L$, necessary for providing a disulfide bond, may be provided by component $P^2$ itself by a —SH moiety as defined herein or may be provided by modifying component $P^2$ accordingly to exhibit a —SH moiety within the above definition of repetitive component $[S—P^2—S]_n$. The —SH moieties for component $P^2$ are preferably as defined herein for components $P^1$ and $P^3$. If such —SH-moieties, necessary to form a disulfide bond (—S—S—) within the above meaning, are provided by component $P^2$ itself this may occur e.g. by at least two cysteines or any further (modified) amino acids or chemical compounds, which carry a —SH moiety, already occurring within the amino acid sequence of component $P^2$ at whatever position of the amino acid sequence of component $P^2$. Alternatively, component $P^2$ may be modified accordingly with a chemical compound, e.g. a cysteine or any further (modified) amino acid or chemical compound, which carries a (free) —SH moiety. Thereby, component $P^2$ preferably carries at least two —SH-moieties, which sulphurs atoms are capable to form a disulfide bond upon condensation with a —SH-moiety of components $P^1$ or $P^3$ as defined herein, or between a first component $P^2$ and a further component $P^2$, etc. Such —SH-moieties are preferably as defined herein. Preferably the at least two SH-moieties are located at the terminal ends or near to the terminal ends of component $P^2$.

According to one specific aspect of the first embodiment of the present invention, component $P^2$ within repetitive component $[S—P^2—S]_n$ of generic formula (I) above may comprise a cysteine as a —SH moiety. In this context, repetitive component $[S—P^2—S]_n$ may thus be written as follows:

[Cys-$P^2$-Cys]$_n$ wherein n and $P^2$ are as defined herein and each Cys provides for the —SH-moiety for the disulfide bond. Cys is the amino acid cysteine in its three letter code. (For illustrative purposes, in the present description the disulfide bond —S—S— generally may also be written as -(Cys-S)—(S-Cys)-, wherein Cys-S represents a Cysteine with an naturally occurring —SH moiety, wherein this —SH moiety forms a disulfide bond with a —SH moiety of a second cysteine. Accordingly, repetitive component [Cys-$P^2$-Cys]$_n$ may also be written as [(S-Cys)-$P^2$-(Cys-S)]$_n$, which indicates that the —SH-moiety is provided by a cysteine and the Cysteine itself provides for the sulfur of the disulfide bond.)

In the context of the entire formula (I) above, this specific aspect of the first embodiment thus may be defined as follows:

L-$P^1$—S-[Cys-$P^2$-Cys]$_n$—S—$P^3$-L wherein L, $P^1$, $P^2$, $P^3$ and n are as defined herein, S is sulphur and each Cys provides for one —SH-moiety for the disulfide bond.

In each case, the SH-moiety, e.g. of a cysteine or any further (modified) amino acid or further compound used for modification of component $P^2$, may be present in the cationic or polycationic peptide or protein or cationic or polycationic polymer as component $P^2$, internally or at one or both of its terminal ends, e.g. if a cationic or polycationic peptide or protein is used as component $P^2$ at the N-terminal end or at the C-terminal end, at both these terminal ends, and/or internally at any position of the cationic or polycationic peptide or protein as component $P^2$. Preferably, the —SH moiety may be present in component $P^2$ at least at one terminal end, more preferably at both terminal ends, e.g. at the N-terminal end and/or at the C-terminal end, more preferably at both the N-terminal and the C-terminal end of a cationic or polycationic peptide or protein as component $P^2$.

Due to its repetitive character component $[S—P^2—S]_n$ may represent a situation, wherein one of the at least two —SH-moieties of component $P^2$ was condensed with a —SH-moiety of a further component $P^2$ of generic formula (I) above, wherein both sulphurs of these —SH-moieties form a disulfide bond (—S—S—) between a first component $P^2$ and at least one further component $P^2$.

In this context, the number of repetitions of component $P^2$ in formula (I) according to the present invention is defined by integer n. n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. If, for example, in repetitive component $[S—P^2—S]_n$ integer n is 5, repetitive component $[S—P^2—S]_n$ preferably reads as follows:

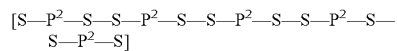

In the above example component $P^2$ occurs 5 times (preferably in a linear order), wherein each component $P^2$ is linked to its neighbor component by a disulfide bond within the above definition of repetitive component $[S—P^2—S]_n$. Any of components $P^2$ may be the same or different from each other.

According to one particular aspect of this embodiment, component $P^2$ represents a cationic or polycationic peptide or protein having a length of about 3 to about 100 amino acids, more preferably having a length of about 3 to about 50 amino acids, even more preferably having a length of about 3 to about 25 amino acids, e.g. having a length of about 3 to 10, 5 to 15, 10 to 20 or 15 to 25 amino acids, more preferably a length of about 5 to about 20 and even more preferably a length of about 10 to about 20.

The cationic or polycationic peptide or protein as component $P^2$ may be any protein or peptide suitable for this purpose and exhibiting at least two —SH-moieties, particular any cationic or polycationic peptide or protein capable to complex a nucleic acid as defined according to the present invention, and thereby preferably condensing the nucleic acid.

Particularly preferred, cationic or polycationic peptides or proteins as component $P^2$ exhibiting at least two —SH-moieties may be selected from protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila antennapedia*), pAntp, plsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, Loligomere, Arginine-rich peptides, Calcitonin-peptides, FGF, Lactoferrin, histones, VP22 derived or analog peptides, HSV, VP22 (Herpes simplex), MAP, KALA or protein transduction domains (PTDs, PpT620, prolin-rich peptides, lysine-rich peptides, Pep-1, L-oligomers, Calcitonin peptide(s), etc.

According to one particular preferred aspect of the first embodiment of the present invention, cationic or polycationic peptides or proteins as component $P^2$ are selected from following cationic peptides having the following total sum formula (II), preferably under the provison that they exhibit additionally at least two —SH-moieties:

$\{(Arg)_l;(Lys)_m;(His)_n;(Orn)_o;(Xaa)_x\};$ (formula (II))

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 10% of all amino acids of the oligopeptide; and Xaa may be any amino acid selected from native (=naturally occurring) or non-native amino acids except of Arg, Lys, His or Orn; and x may be any number selected from 0, 1, 2, 3, 4, 5, 6, 7, 8, 9, 10, 11, 12, 13 or 14, provided, that the overall content of Xaa does not exceed 90% of all amino acids of the oligopeptide. Any of amino acids Arg, Lys, His, Orn and Xaa may be positioned at any place of the peptide. Particularly preferred peptides of this formula are oligoarginines such as e.g. $Arg_7$, $Arg_8$, $Arg_9$, Arg $H_3R_9$, $R_9H_3$, $H_3R_9H_3$, $YSSR_9SSY$, $(RKH)_4$, $Y(RKH)_2R$, etc. (SEQ ID NOs: 1-9).

According to a particular preferred aspect of the first embodiment, cationic or polycationic peptides or proteins as component $P^2$, having the empirical formula (II) as shown above and additionally exhibiting at least two —SH-moieties, may be, without being restricted thereto, selected from the following subgroup of formulae:

(SEQ ID NOs: 2-3, 10-15)
$Arg_8$, $Arg_9$, $Arg_{10}$, $Arg_{11}$, $Arg_{12}$, $Arg_{13}$, $Arg_{14}$, $Arg_{15}$;

(SEQ ID NOs: 16-23)
$Lys_8$, $Lys_9$, $Lys_{10}$, $Lys_{11}$, $Lys_{12}$, $Lys_{13}$, $Lys_{14}$, $Lys_{15}$;

(SEQ ID NOs: 24-31)
$His_8$, $His_9$, $His_{10}$, $His_{11}$, $His_{12}$, $His_{13}$, $His_{14}$, $His_{15}$;

(SEQ ID NOs: 32-39)
$Orn_8$, $Orn_9$, $Orn_{10}$, $Orn_{11}$, $Orn_{12}$, $Orn_{13}$, $Orn_{14}$, $Orn_{15}$;

According to a further particularly preferred aspect of the first embodiment, cationic or polycationic peptides or proteins as component $P^2$, having the empirical formula (II) as shown above and additionally exhibiting at least two —SH-moieties, may be, without being restricted thereto, selected from the following subgroup of formulae, wherein the following formulae (as with empirical formula (II)) do not specify any amino acid order, but are intended to reflect empirical formulae by exclusively specifying the (number of) amino acids as components of the respective peptide. Accordingly, as an example, empirical formula $Arg_{(7-14)}Lys_1$ is intended to mean that peptides falling under this formula contain 7 to 14 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(7-14)}Lys_1$, $Arg_{(7-14)}His_1$, $Arg_{(7-14)}Orn_1$, $Lys_{(7-14)}His_1$, $Lys_{(7-14)}Orn_1$, $His_{(7-14)}Orn_1$;

$Arg_{(6-13)}Lys_2$, $Arg_{(6-13)}His_2$, $Arg_{(6-13)}Orn_2$, $Lys_{(6-13)}His_2$, $Lys_{(6-13)}Orn_2$, $His_{(6-13)}Orn_2$;

$Arg_{(5-12)}Lys_3$, $Arg_{(5-12)}His_3$, $Arg_{(5-12)}Orn_3$, $Lys_{(5-12)}His_3$, $Lys_{(5-12)}Orn_3$, $His_{(5-12)}Orn_3$;

$Arg_{(4-11)}Lys_4$, $Arg_{(4-11)}His_4$, $Arg_{(4-11)}Orn_4$, $Lys_{(4-11)}His_4$, $Lys_{(4-11)}Orn_4$, $His_{4-11)}Orn_4$;

$Arg_{(3-10)}Lys_5$, $Arg_{(3-10)}His_5$, $Arg_{(3-10)}Orn_5$, $Lys_{(3-10)}His_5$, $Lys_{(3-10)}Orn_5$, $His_{(3-10)}Orn_5$;

$Arg_{(2-9)}Lys_6$, $Arg_{(2-9)}His_6$, $Arg_{(2-9)}Orn_6$, $Lys_{(2-9)}His_6$, $Lys_{(2-9)}Orn_6$, $His_{(2-9)}Orn_6$;

$Arg_{(1-8)}Lys_7$, $Arg_{(1-8)}His_7$, $Arg_{(1-8)}Orn_7$, $Lys_{(1-8)}His_7$, $Lys_{(1-8)}Orn_7$, $His_{(1-8)}Orn_7$;

$Arg_{(6-13)}Lys_1His_1$, $Arg_{(6-13)}Lys_1Orn_1$, $Orn_1$, $Arg_{(6-13)}His_1Orn_1$, $Arg_1Lys_{(6-13)}His_1$, $Arg_1Lys_{(6-13)}Orn_1$, $Lys_{(6-13)}His_1Orn_1$, $Arg_1Lys_1His_{(6-13)}$, $Arg_1His_{(6-13)}Orn_1$, $Lys_1His_{(6-13)}Orn_1$;

$Arg_{(5-12)}Lys_2His_1$, $Arg_{(5-12)}Lys_1His_2$, $Arg_{(5-12)}Lys_2Orn_1$, $Arg_{(5-12)}Lys_1Orn_2$, $Arg_{(5-12)}His_2Orn_1$, $Arg_{(5-12)}His_1Orn_2$, $Arg_2Lys_{(5-12)}His_1$, $Arg_1Lys_{(5-12)}His_2$, $Arg_2Lys_{(5-12)}Orn_1$, $Arg_1Lys_{(5-12)}Orn_2$, $Lys_{(5-12)}His_2Orn_1$, $Lys_{(5-12)}His_1Orn_2$, $Arg_2Lys_1His_{(5-12)}$, $Arg_1Lys_2His_{(5-12)}$, $Arg_2His_{(5-12)}Orn_1$, $Arg_1His_{(5-12)}Orn_2$, $Lys_2His_{(5-12)}Orn_1$, $Lys_1His_{(5-12)}Orn_2$;

$Arg_{(4-11)}Lys_3His_1$, $Arg_{(4-11)}Lys_2His_2$, $Arg_{(4-11)}Lys_1His_3$, $Arg_{(4-11)}Lys_3Orn_1$, $Arg_{(4-11)}Lys_2Orn_2$, $Arg_{(4-11)}Lys_1Orn_3$, $Arg_{(4-11)}His_3Orn_1$, $Arg_{(4-11)}His_2Orn_2$, $Arg_{(4-11)}His_1Orn_3$, $Arg_3Lys_{(4-11)}His_1$, $Arg_2Lys_{(4-11)}His_2$, $Arg_1Lys_{(4-11)}His_3$, $Arg_3Lys_{(4-11)}Orn_1$, $Arg_2Lys_{(4-11)}Orn_2$, $Arg_1Lys_{(4-11)}Orn_3$, $Lys_{(4-11)}His_3Orn_1$, $Lys_{(4-11)}His_2Orn_2$, $Lys_{(4-11)}His_1Orn_3$, $Arg_3Lys_1His_{(4-11)}$, $Arg_2Lys_2His_{(4-11)}$, $Arg_1Lys_3His_{(4-11)}$, $Arg_3His_{(4-11)}Orn_1$, $Arg_2His_{(4-11)}Orn_2$, $Arg_1His_{(4-11)}Orn_3$, $Lys_3His_{(4-11)}Orn_1$, $Lys_2His_{(4-11)}Orn_2$, $Lys_1His_{(4-11)}Orn_3$;

$Arg_{(3-10)}Lys_4His_1$, $Arg_{(3-10)}Lys_3His_2$, $Arg_{(3-10)}Lys_2His_3$, $Arg_{(3-10)}Lys_1His_4$, $Arg_{(3-10)}Lys_4Orn_1$, $Arg_{(3-10)}Lys_3Orn_2$, $Arg_{(3-10)}Lys_2Orn_3$, $Arg_{(3-10)}Lys_1Orn_4$, $Arg_{(3-10)}His_4Orn_1$, $Arg_{(3-10)}His_3Orn_2$, $Arg_{(3-10)}His_2Orn_3$, $Arg_{(3-10)}His_1Orn_4$, $Arg_4Lys_{(3-10)}His_1$, $Arg_3Lys_{(3-10)}His_2$, $Arg_2Lys_{(3-10)}His_3$, $Arg_1Lys_{(3-10)}His_4$, $Arg_4Lys_{(3-10)}Orn_1$, $Arg_3Lys_{(3-10)}Orn_2$, $Arg_2Lys_{(3-10)}Orn_3$, $Arg_1Lys_{(3-10)}Orn_4$, $Lys_{(3-10)}His_4Orn_1$, $Lys_{(3-10)}His_3Orn_2$, $Lys_{(3-10)}His_2Orn_3$, $Lys_{(3-10)}His_1Orn_4$, $Arg_4Lys_1His_{(3-10)}$, $Arg_3Lys_2His_{(3-10)}$, $Arg_2Lys_3His_{(3-10)}$, $Arg_1Lys_4His_{(3-10)}$, $Arg_4His_{(3-10)}Orn_1$, $Arg_3His_{(3-10)}Orn_2$, $Arg_2His_{(3-10)}Orn_3$, $Arg_1His_{(3-10)}Orn_4$, $Lys_4His_{(3-10)}Orn_1$, $Lys_3His_{(3-10)}Orn_2$, $Lys_2His_{(3-10)}Orn_3$, $Lys_1His_{(3-10)}Orn_4$;

$Arg_{(2-9)}Lys_5His_1$, $Arg_{(2-9)}Lys_4His_2$, $Arg_{(2-9)}Lys_3His_3$, $Arg_{(2-9)}Lys_2His_4$, $Arg_{(2-9)}Lys_1His_5$, $Arg_{(2-9)}Lys_5Orn_1$, $Arg_{(2-9)}Lys_4Orn_2$, $Arg_{(2-9)}Lys_3Orn_3$, $Arg_{(2-9)}Lys_2Orn_4$, $Arg_{(2-9)}Lys_1Orn_5$, $Arg_{(2-9)}His_5Orn_1$, $Arg_{(2-9)}His_4Orn_2$, $Arg_{(2-9)}His_3Orn_3$, $Arg_{(2-9)}His_2Orn_4$, $Arg_{(2-9)}His_1Orn_5$, $Arg_5Lys_{(2-9)}His$, $Arg_4Lys_{(2-9)}His_2$, $Arg_3Lys_{(2-9)}His_3$, $Arg_2Lys_{(2-9)}His_4$, $Arg_1Lys_{(2-9)}His_5$, $Arg_5Lys_{(2-9)}Orn_1$, $Arg_4Lys_{(2-9)}Orn_2$, $Arg_3Lys_{(2-9)}Orn_3$, $Arg_2Lys_{(2-9)}Orn_4$, $Arg_1Lys_{(2-9)}Orn_5$, $Lys_{(2-9)}His_5Orn$, $Lys_{(2-9)}His_4Orn_2$, $Lys_{(2-9)}His_3Orn_3$, $Lys_{(2-9)}His_2Orn_4$, $Lys_{(2-9)}His_1Orn_5$, $Arg_5Lys_1His_{(2-9)}$, $Arg_4Lys_2His_{(2-9)}$, $Arg_3Lys_3His_{(2-9)}$, $Arg_2Lys_4His_{(2-9)}$, $Arg_1Lys_5His_{(2-9)}$, $Arg_5His_{(2-9)}Orn_1$, $Arg_4His_{(2-9)}Orn_2$, $Arg_3His_{(2-9)}Orn_3$, $Arg_2His_{(2-9)}Orn_4$, $Arg_1His_{(2-9)}Orn_5$, $Lys_5His_{(2-9)}Orn_1$, $Lys_4His_{(2-9)}Orn_2$, $Lys_3His_{(2-9)}Orn_3$, $Lys_2His_{(2-9)}Orn_4$, $Lys_1His_{(2-9)}Orn_5$;

$Arg_{(1-8)}Lys_6His_1$, $Arg_{(1-8)}Lys_5His_2$, $Arg_{(1-8)}Lys_4His_3$, $Arg_{(1-8)}Lys_3His_4$, $Arg_{(1-8)}Lys_2His_5$, $Arg_{(5-8)}Lys_1His_6$, $Arg_{(1-8)}Lys_6Orn_1$, $Arg_{(1-8)}Lys_5Orn_2$, $Arg_{(1-8)}Lys_4Orn_3$, $Arg_{(1-8)}Lys_3Orn_4$, $Arg_{(1-8)}Lys_2Orn_5$, $Arg_{(1-8)}Lys_1Orn_6$, $Arg_{(1-8)}His_6Orn_1$, $Arg_{(1-8)}His_5Orn_2$, $Arg_{(1-8)}His_4Orn_3$, $Arg_{(1-8)}His_3Orn_4$, $Arg_{(1-8)}His_2Orn_5$, $Arg_{(1-8)}His_1Orn_6$, $Arg_6Lys_{(1-8)}His_1$, $Arg_5Lys_{(1-8)}His_2$, $Arg_4Lys_{(1-8)}His_3$, $Arg_3Lys_{(1-8)}His_4$, $Arg_2Lys_{(1-8)}His_5$, $Arg_1Lys_{(1-8)}His_6$, $Arg_6Lys_{(1-8)}Orn_1$, $Arg_5Lys_{(1-8)}Orn_2$, $Arg_4Lys_{(1-8)}Orn_3$, $Arg_3Lys_{(1-8)}Orn_4$, $Arg_2Lys_{(1-8)}Orn_5$, $Arg_1Lys_{(1-8)}Orn_6$, $Lys_{(1-8)}His_6Orn_1$, $Lys_{(1-8)}His_5Orn_2$, $Lys_{(1-8)}His_4Orn_3$, $Lys_{(1-8)}His_3Orn_4$, $Lys_{(1-8)}His_2Orn_5$, $Lys_{(1-8)}His_1Orn_6$, $Arg_6Lys_1His_{(1-8)}$, $Arg_5Lys_2His_{(1-8)}$, $Arg_4Lys_3His_{(1-8)}$, $Arg_3Lys_4His_{(1-8)}$, $Arg_2Lys_5His_{(1-8)}$, $Arg_1Lys_6His_{(1-8)}$, $Arg_6His_{(1-8)}Orn_1$, $Arg_5His_{(1-8)}Orn_2$, $Arg_4His_{(1-8)}Orn_3$, $Arg_3His_{(1-8)}Orn_4$, $Arg_2His_{(1-8)}Orn_5$, $Arg_1His_{(1-8)}Orn_6$, $Lys_6His_{(1-8)}Orn_1$, $Lys_5His_{(1-8)}Orn_2$, $Lys_4His_{(1-8)}Orn_3$, $Lys_3His_{(1-8)}Orn_4$, $Lys_2His_{(1-8)}Orn_4$, $Lys_1His_{(1-8)}Orn_6$, $Arg_{(5-12)}Lys_1His_1Orn_1$, $Arg_1Lys_{(5-12)}His_1Orn_1$, $Arg_1Lys_1His_{(5-12)}Orn_1$, $Arg_1Lys_1His_1Orn_{(5-12)}$;

$Arg_{(4-11)}Lys_2His_1Orn_1$, $Arg_{(4-11)}Lys_1His_2Orn$, $Arg_{(4-11)}Lys_1His_1Orn_2$, $Arg_2Lys_{(4-11)}His_1Orn_1$, $Arg_1Lys_{(4-11)}His_2Orn_1$, $Arg_1Lys_{(4-11)}His_1Orn_2$, $Arg_2Lys_1His_{(4-11)}Orn_1$, $Arg_1Lys_2His_{(4-11)}Orn_1$, $Arg_1Lys_1His_{(4-11)}Orn_2$, $Arg_2Lys_1His_1Orn_{(4-11)}$, $Arg_1Lys_2His_1Orn_{(4-11)}$, $Arg_1Lys_1His_2Orn_{(4-11)}$;

$Arg_{(3-10)}Lys_3His_1Orn_1$, $Arg_{(3-10)}Lys_2His_2Orn_1$, $Arg_{(3-10)}Lys_2His_1Orn_2$, $Arg_{(3-10)}Lys_1His_2Orn_2$, $Arg_{(3-10)}Lys_1His_1Orn_3$, $Arg_3Lys_{(3-10)}His_1Orn_1$, $Arg_2Lys_{(3-10)}His_2Orn_1$, $Arg_2Lys_{(3-10)}His_1Orn_2$, $Arg_1Lys_{(3-10)}His_2Orn_2$, $Arg_1Lys_{(3-10)}His_1Orn_3$, $Arg_3Lys_1His_{(3-10)}Orn_1$, $Arg_2Lys_2His_{(3-10)}Orn_1$, $Arg_2Lys_1His_{(3-10)}Orn_2$, $Arg_1Lys_2His_{(3-10)}Orn_2$, $Arg_1Lys_1His_{(3-10)}Orn_3$, $Arg_3Lys_1His_1Orn_{(3-10)}$, $Arg_2Lys_2His_1Orn_{(3-10)}$, $Arg_2Lys_1His_2Orn_{(3-10)}$, $Arg_1Lys_2His_2Orn_{(3-10)}$, $Arg_1Lys_1His_3Orn_{(3-10)}$;

$Arg_{(2-9)}Lys_4His_1Orn_1$, $Arg_{(2-9)}Lys$, $His_4Orn_1$, $Arg_{(2-9)}Lys_1His_1Orn_4$, $Arg_{(2-9)}Lys_3His_2Orn_1$, $Arg_{(2-9)}Lys_3His_1Orn_2$, $Arg_{(2-9)}Lys_2His_3Orn_1$, $Arg_{(2-9)}Lys_2His_1Orn_3$, $Arg_{(2-9)}Lys_1His_2Orn_3$, $Arg_{(2-9)}Lys_1His_3Orn_2$, $Arg_{(2-9)}Lys_2His_2Orn_2$, $Arg_4Lys_{(2-9)}His_1Orn_1$, $Arg_1Lys_{(2-9)}His_4Orn_1$, $Arg_1Lys_{(2-9)}His_1Orn_4$, $Arg_3Lys_{(2-9)}His_2Orn_1$, $Arg_3Lys_{(2-9)}His_1Orn_2$, $Arg_2Lys_{(2-9)}His_3Orn_1$, $Arg_2Lys_{(2-9)}His_1Orn_3$, $Arg_1Lys_{(2-9)}His_2Orn_3$, $Arg_1Lys_{(2-9)}His_3Orn_2$, $Arg_2Lys_{(2-9)}His_2Orn_2$, $Arg_4Lys_1His_{(2-9)}Orn_1$, $Arg_1Lys_4His_{(2-9)}Orn_1$, $Arg_1Lys_1His_{(2-9)}Orn_4$, $Arg_3Lys_2His_{(2-9)}Orn_1$, $Arg_3Lys_1His_{(2-9)}Orn_2$, $Arg_2Lys_3His_{(2-9)}Orn_1$, $Arg_2Lys_1His_{(2-9)}Orn_3$, $Arg_1Lys_2His_{(2-9)}Orn_3$, $Arg_1Lys_3His_{(2-9)}Orn_2$, $Arg_2Lys_2His_{(2-9)}Orn_2$, $Arg_4Lys_1His_1Orn_{(2-9)}$, $Arg_1Lys_4His_1Orn_{(2-9)}$, $Arg_1Lys_1His_4Orn_{(2-9)}$, $Arg_3Lys_2His_1Orn_{(2-9)}$, $Arg_3Lys_1His_2Orn_{(2-9)}$, $Arg_2Lys_3His_1Orn_{(2-9)}$, $Arg_2Lys_1His_3Orn_{(2-9)}$, $Arg_1Lys_2His_3Orn_{(2-9)}$, $Arg_1Lys_3His_2Orn_{(2-9)}$, $Arg_2Lys_2His_2Orn_{(2-9)}$;

$Arg_{(1-8)}Lys_5His_1Orn_1$, $Arg_{(1-8)}Lys_1His_5Orn_1$, $Arg_{(1-8)}Lys_1His_1Orn_5$, $Arg_{(1-8)}Lys_4His_2Orn$, $Arg_{(1-8)}Lys_2His_4Orn_1$, $Arg_{(1-8)}Lys_2His_1Orn_4$, $Arg_{(1-8)}Lys_1His_2Orn_4$, $Arg_{(1-8)}Lys_1His_4Orn_2$, $Arg_{(1-8)}Lys_4His_1Orn_2$, $Arg_{(1-8)}Lys_3His_3Orn_1$, $Arg_{(1-8)}Lys_3His_1Orn_3$, $Arg_{(1-8)}Lys_1His_3Orn_3$, $Arg_5Lys_{(1-8)}His_1Orn_1$, $Arg_1Lys_{(1-8)}His_5Orn$, $Arg_1Lys_{(1-8)}His_1Orn_5$, $Arg_4Lys_{(1-8)}His_2Orn_1$, $Arg_2Lys_{(1-8)}His_4Orn_1$, $Arg_2Lys_{(1-8)}His_1Orn_4$, $Arg_1Lys_{(1-8)}His_2Orn_4$, $Arg_1Lys_{(1-8)}His_4Orn_2$, $Arg_4Lys_{(1-8)}His_1Orn_2$, $Arg_3Lys_{(1-8)}His_3Orn_1$, $Arg_3Lys_{(1-8)}His_1Orn_3$, $Arg_1Lys_{(1-8)}His_3Orn_3$, $Arg_5Lys$, $His_{(1-8)}Orn_1$, $Arg_1Lys_5His_{(1-8)}Orn_1$, $Arg_1Lys_1His_{(1-8)}Orn_5$, $Arg_4Lys_2His_{(1-8)}Orn_1$, $Arg_2Lys_4His_{(1-8)}Orn_1$, $Arg_2Lys_1His_{(1-8)}Orn_4$, $Arg_1Lys_2His_{(1-8)}Orn_4$, $Arg_1Lys_4His_{(1-8)}Orn_2$, $Arg_4Lys_1His_{(1-8)}Orn_2$, $Arg_3Lys_3His_{(1-8)}Orn_1$, $Arg_3Lys_1His_{(1-8)}Orn_3$, $Arg_1Lys_3His_{(1-8)}Orn_3$, $Arg_5Lys$, $His_1Orn_{(1-8)}$, $Arg_1Lys_5His_1Orn_{(1-8)}$, $Arg_1Lys_1His_5Orn_{(1-8)}$, $Arg_4Lys_2His_1Orn_{(1-8)}$, $Arg_2Lys_4His_1Orn_{(1-8)}$, $Arg_2Lys_1His_4Orn_{(1-8)}$, $Arg_1Lys_2His_4Orn_{(1-8)}$, $Arg_1Lys_4His_2Orn_{(1-8)}$, $Arg_4Lys_1His_2Orn_{(1-8)}$, $Arg_3Lys_3His_1Orn_{(1-8)}$, $Arg_3Lys_1His_3Orn_{(1-8)}$, $Arg_1Lys_3His_3Orn_{(1-8)}$;

According to another particular preferred aspect of the first embodiment, cationic or polycationic peptides or proteins as component $P^2$, having the empirical formula (II) as shown above, and additionally exhibiting at least two —SH-moieties may be, without being restricted thereto, selected from following formulae: $Arg_8$, $Arg_9$, $Arg_{10}$, $Arg_{11}$, $Arg_{12}$, $Arg_{13}$, $Arg_{14}$, $Arg_{15}$; $Lys_8$, $Lys_9$, $Lys_{10}$, $Lys_{11}$, $Lys_{12}$, $Lys_{13}$, $Lys_{14}$, $Lys_{15}$; $His_8$, $His_9$, $His_{10}$, $His_{11}$, $His_{12}$, $His_{13}$, $His_{14}$, $His_{15}$; $Orn_8$, $Orn_9$, $Orn_{10}$, $Orn_{11}$, $Orn_{12}$, $Orn_{13}$, $Orn_{14}$, $Orn_{15}$; (SEQ ID NOs: 2-3, 10-39, see above).

According to a further particular preferred aspect of the first embodiment, cationic or polycationic peptides or proteins as component $P^2$, having the empirical formula (II) as shown above, and additionally exhibiting at least two —SH-moieties may be, without being restricted thereto, selected from the subgroup consisting of generic formulas $Arg_9$ (also termed $R_9$), $Arg_9His_3$ (also termed $R_9H_3$), $His_3Arg_9His_3$ (also termed $H_3R_9H_3$), $TyrSerSerArg_9SerSerTyr$ (also termed $YSSR_9SSY$), $His_3Arg_9SerSerTyr$ (also termed $H_3R_9SSY$), $(ArgLysHis)_4$ (also termed $(RKH)_4$), $Tyr(ArgLysHis)_2Arg$ (also termed $Y(RKH)_2R$); (SEQ ID NOs: 2, 5-9, 40, see above). Even more preferably, these generic formulas are defined as follows:

According to a one further particular preferred aspect of the first embodiment, the cationic or polycationic peptide or protein as component $P^2$, when defined according to formula $\{(Arg)_i;(Lys)_m;(His)_n;(Orn)_o;(Xaa)_x\}$ (formula (II)) as shown above, and additionally exhibiting at least two —SH-moieties may be, without being restricted thereto, selected from formula (IIa), preferably under the provision that at least one —SH-moiety is provided by a cysteine residue:

$$\{(Arg)_i;(Lys)_m;(His)_n;(Orn)_o;(Cys)_x\} \quad \text{(formula (IIa))}$$

wherein $(Arg)_i;(Lys)_n;(His)_n;(Orn)_o;$ and x are as defined herein,

Alternatively, the cationic or polycationic peptide or protein as component $P^2$, when defined according to formula $\{(Arg)_i;(Lys)_m;(His)_n;(Orn)_o;(Xaa)_x\}$ (formula (II)) as shown above, and additionally exhibiting at least two —SH-moieties may be, without being restricted thereto, selected from formula (IIa'), preferably under the provision that at least one —SH— moiety is provided by a cysteine residue:

$$\{(Arg)_i;(Lys)_m;(His)_n;(Orn)_o;(Xaa')_x;(Cys)_y\} \quad \text{(formula (IIa'))}$$

wherein $(Arg)_i;(Lys)_m;(His)_n;(Orn)_o;$ and x are as defined herein, Xaa' is any amino acid selected from native (=naturally occurring) or non-native amino acids except of Arg, Lys, His, Orn or Cys and y is any number selected from 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

These aspects of the first embodiment of the present invention may apply to situations, wherein component $P^2$ is selected from a cationic or polycationic peptide or protein according to empirical formula $(Arg)_i;(Lys)_m;(His)_n;(Orn)_o;(Xaa)_x$ (formula (II)) as shown above, which comprises or has been modified with at least one cysteine as —SH moiety in the above meaning such that the cationic or polycationic peptide as component $P^2$ carries at least one cysteine, which is capable to form a disulfide bond with other components of formula (I).

According to another particular preferred aspect of the first embodiment, the cationic or polycationic peptide or protein as component $P^2$, when defined according to formula $\{(Arg)_i;(Lys)_m;(His)_n;(Orn)_o;(Xaa)_x\}$ (formula (II)) as shown above, and preferably additionally exhibiting at least two —SH-moieties may be, without being restricted thereto, selected from formula (IIb), preferably under the provision that the at least two —SH-moieties are provided by two terminal cysteine residues:

$$Cys\{(Arg)_i;(Lys)_m;(His)_n;(Orn)_o;(Xaa)_x\}Cys \quad \text{(formula (IIb))}$$

wherein $(Arg)_i;(Lys)_m;(His)_n;(Orn)_o;(Xaa)_x$ are as defined herein and form a core of amino acids according to (semiempirical) formula (II). Exemplary examples may comprise any of the above sequences flanked by two Cys and following sequences:

(SEQ ID NOs: 41 to 72)
Cys(Arg$_8$)Cys, Cys(Arg$_9$)Cys, Cys(Arg$_{10}$)Cys,

Cys(Arg$_{11}$)Cys, Cys(Arg$_{12}$)Cys, Cys(Arg$_{13}$)Cys,

Cys(Arg$_{14}$)Cys, Cys(Arg$_{15}$)Cys; Cys(Lys$_8$)Cys,

Cys(Lys$_9$)Cys, Cys(Lys$_{10}$)Cys, Cys(Lys$_{11}$)Cys,

Cys(Lys$_{12}$)Cys, Cys(Lys$_{13}$)Cys, Cys(Lys$_{14}$)Cys,

Cys(Lys$_{15}$)Cys; Cys(His$_8$)Cys, Cys(His$_9$)Cys,

Cys(His$_{10}$)Cys, Cys(His$_{11}$)Cys, Cys(His$_{12}$)Cys,

Cys(His$_{13}$)Cys, Cys(His$_{14}$)Cys, Cys(His$_{15}$)Cys;

Cys(Orn$_8$)Cys, Cys(Orn$_9$)Cys, Cys(Orn$_{10}$)Cys,

Cys(Orn$_{11}$)Cys, Cys(Orn$_{12}$)Cys, Cys(Orn$_{13}$)Cys,

Cys(Orn$_{14}$)Cys, Cys(Orn$_{15}$)Cys, more preferably following exemplary sequences (SEQ ID NOs: 73 to 84):

| | |
|---|---|
| CysArg$_9$Cys: | Cys-Arg-Arg-Arg-Arg-Arg-Arg-Arg-Arg-Cys |
| CysArg$_9$His$_3$Cys: | Cys-Arg-Arg-Arg-Arg-Arg-Arg-Arg-Arg-His-His-His-Cys |
| CysHis$_3$Arg$_9$His$_3$Cys: | Cys-His-His-His-Arg-Arg-Arg-Arg-Arg-Arg-Arg-Arg-Arg-His-His-His-Cys |
| CysTyrSerSerArg$_9$SerSerTyrCys: | Cys-Tyr-Ser-Ser-Arg-Arg-Arg-Arg-Arg-Arg-Arg-Arg-Arg-Ser-Ser-Tyr-Cys |
| CysHis$_3$Arg$_9$SerSerTyrCys: | Cys-His-His-His-Arg-Arg-Arg-Arg-Arg-Arg-Arg-Arg-Arg-Ser-Ser-Tyr-Cys |
| Cys(ArgLysHis)$_4$Cys: | Cys-Arg-Lys-His-Arg-Lys-His-Arg-Lys-His-Arg-Lys-His-Cys |
| CysTyr(ArgLysHis)$_2$ArgCys: | Cys-Tyr-Arg-Lys-His-Arg-Lys-His-Arg-Cys |
| CysHis$_3$Arg$_9$His$_3$Cys: | Cys-His-His-His-Arg-Arg-Arg-Arg-His-His-His-Cys |
| CysHis$_6$Arg$_9$His$_6$Cys: | Cys-His-His-His-His-His-His-Arg-Arg-Arg-Arg-Arg-Arg-Arg-His-His-His-His-His-His-Cys |
| CysHis$_3$Arg$_4$His$_3$Cys: | Cys-His-His-His-Arg-Arg-Arg-Arg-His-His-His-Cys |
| CysHis$_6$Arg$_4$His$_6$Cys: | Cys-His-His-His-His-His-His-Arg-Arg-Arg-Arg-His-His-His-His-His-His-Cys |
| CysArg$_{12}$Cys: | Cys-Arg-Arg-Arg-Arg-Arg Arg-Arg-Arg-Arg-Arg-Arg-Arg-Cys |

This aspect of the first embodiment of the present invention may apply to situations, wherein the polycationic peptide or protein as component $P^2$, e.g. when defined according to empirical formula $(Arg)_l;(Lys)_m;(His)_n;(Orn)_o;(Xaa)_x$ (formula (II)) as shown above, has been modified with at least two (terminal) cysteines as —SH moieties in the above meaning such that component $P^2$ carries at least two (terminal) cysteines, which are capable to form a disulfide bond with other components of formula (I).

According to another aspect of the first embodiment, component $P^2$ represents a cationic or polycationic polymer, selected from e.g. any cationic polymer suitable in this context, provided that this cationic polymer exhibits at least two —SH-moieties, which provide for a disulfide bond linking component $P^2$ with component $P^1$ or $P^3$, or with further component(s) $P^2$ or amino acid components $(AA)_x$. Thus, likewise as defined herein, component $P^2$ may occur as a repetitive component as defined herein as represented by subformula $[S—P^3—S]$, or $\{[S—P^2—S]_a/[S-(AA)_x-S]_b\}$, wherein the same or different cationic or polycationic polymers $P^2$ may be used in said repetitive component.

Preferably, component $P^2$ represents a cationic or polycationic polymer, typically exhibiting a molecular weight of about 0.5 kDa to about 100 kDa, of about 1 kDa to about 75 kDa, of about 5 kDa to about 50 kDa, of about 5 kDa to about 30 kDa, or a molecular weight of about 10 kDa to about 50 kDa, or of about 10 kDa to about 30 kDa, preferably of about 0.5 kDa to about 30 kDa, more preferably of about 1 kDa to about 20 kDa, and even more preferably of about 1.5 kDa to about 10 kDa. Additionally, the cationic or polycationic polymer as component $P^2$ typically exhibits at least two —SH moieties, which are capable to form a disulfide linkage upon condensation with either components $P^1$ or $P^3$ or with other components $P^2$ or amino acid components $(AA)_x$, as defined herein.

When component $P^2$ represents a cationic or polycationic polymer, such a polymer may be selected from acrylates, modified acrylates, such as pDMAEMA (poly(dimethylaminoethyl methylacrylate)), chitosanes, aziridines or 2-ethyl-2-oxazoline (forming oligo ethylenimines or modifed oligoethylenimines), polymers obtained by reaction of bisacrylates with amines forming oligo beta aminoesters or poly amido amines, or other polymers like polyesters, polycarbonates, etc. Each molecule of these cationic or polycationic polymers typically exhibits at least two —SH-moieties, wherein these at least two —SH-moieties may be introduced into the cationic or polycationic polymer by chemical modifications, e.g. using imonothiolan, 3-thio propionic acid or introduction of —SH-moieties containing amino acids, such as cystein, methionine or any further (modified) amino acid. Such —SH-moieties are preferably as already defined above for components $P^1$, $P^2$ or $P^3$.

Component $P^2$ of formula (I) of the present invention preferably occurs as repetitive component $[—S—P^2—S—]_n$. Such a repetitive component $[S—P^2—S]_n$ may be prepared using at least one or even more of the same or different of the above defined components $P^2$ and polymerizing same in a polymerization condensation reaction via their —SH-moieties.

According to one specific aspect of the first embodiment, such a repetitive component $[S—P^2—S]_n$ may be prepared using at least one or even more of the same or different of the above defined cationic or polycationic peptides or proteins, and polymerizing same in a polymerization condensation reaction via their —SH-moieties. Accordingly, such a repetitive component $[S—P^2—S]_n$ contains a number of at least one or even more of the same or different of the above defined cationic or polycationic proteins or peptides determined by integer n.

According to another specific aspect of the first embodiment, such a repetitive component $[S—P^2—S]_n$ may be prepared using at least one or even more of the same or different of the above defined cationic or polycationic polymers, and polymerizing same in a polymerization condensation reaction via their —SH-moieties. Accordingly, such a repetitive component $[S—P^2—S]_n$ contains a number of at least one or even more of the same or different of the above defined cationic or polycationic polymers determined by integer n.

According to a further specific aspect of the first embodiment, such a repetitive component $[S—P^2—S]_n$ may be prepared using at least one or even more of the same or different of the above defined cationic or polycationic polymers and at least one or even more of the same or different of the above defined cationic or polycationic proteins or peptides, and polymerizing same in a polymerization condensation reaction via their —SH-moieties. Accordingly, such a repetitive component $[S—P^2—S]_n$ contains a number of at least one or even more of the same or different of the above defined cationic or polycationic polymers and at least one or even more of the same or different of the above defined cationic or polycationic proteins or peptides, both together determined by integer n.

According to a further aspect of the first embodiment, the inventive polymeric carrier according to formula (I) above, may comprise at least one amino acid component $(AA)_x$, wherein AA is preferably an amino acid as defined in the following, which, when occurring as amino acid component $(AA)_x$, allows to (substantially) modify the biophysical/biochemical properties of the inventive polymeric carrier according to formula (I) as defined herein. According to the present invention, the number of amino acids in such an amino acid component $(AA)_x$ (repetitions) is defined by x. In the above context, x is preferably an integer and may be selected from a range of about 1 to 100, preferably from a range of about 1 to 50, more preferably 1 to 30, and even more preferably selected from a number comprising 1, 2, 3, 4, 5, 6, 7, 8, 9, 10, 11, 12, 13, 14 or 15-30, e.g. from a range of about 1 to 30, from a range of about 1 to 15, or from a number comprising 1, 2, 3, 4, 5, 6, 7, 8, 9, 10, 11, 12, 13, 14 or 15, or may be selected from a range formed by any two of the afore mentioned values.

Such components $(AA)_x$ may be contained in every parts of the inventive polymeric carrier according to formula (I) above and therefore may be attached to all components of the inventive polymeric carrier according to formula (I). It is particularly preferred that $(AA)_x$ is present as ligand or part of the repetitive component $[S—P^2—S]_n$.

In this context it is particularly preferred that the amino acid component $(AA)_x$ contains or is flanked (e.g. terminally) by at least one —SH containing moiety, which allows introducing this component $(AA)_x$ via a disulfide bond into the polymeric carrier according to formula (I) as defined herein. In this context, the amino acid component $(AA)_x$ may also be read as a component $—S-(AA)_x-$ or $—S-(AA)_x-S—$, wherein S represents a —SH containing moiety (or, of course, one sulfur of a disulfide bond), e.g. a cysteine residue. In the specific case that the —SH containing moiety represents a cysteine, the amino acid component $(AA)_x$ may also be read as -Cys-$(AA)_x$- or -Cys-$(AA)_x$-Cys- wherein Cys represents Cysteine and provides for the necessary —SH-moiety for a disulfide bond. (Accordingly, -Cys-$(AA)_x$-Cys- may also be written as (S-Cys)-$(AA)_x$-(Cys-S)— and -Cys-$(AA)_x$- may also be written as (S-Cys)-$(AA)_x$-).) The —SH containing moiety may be also introduced into the amino acid component $(AA)_x$ using any of modifications or reactions as shown above for components $P^1$, $P^2$ or $P^3$. In the specific case that the amino acid component $(AA)_x$ is linked to two components of the inventive polymeric carrier according to formula (I) it is preferred that $(AA)_x$ contains at least two —SH-moieties, e.g. at least two Cysteines, preferably at its terminal ends. This is particularly preferred if $(AA)_x$ is part of the repetitive component $[S—P^2—S]_n$.

In an alternative the amino acid component $(AA)_x$ is introduced into the inventive polymeric carrier according to formula (I) as defined herein via any chemical possible addition reaction. Therefore the amino acid component $(AA)_x$ contains at least one further functional moiety, which allows attaching same to a further component as defined herein, e.g. component $P^1$ or $P^3$, $P^2$, L, or a further amino acid component $(AA)_x$, etc. Such functional moieties may be selected from functionalities which allow the attachment of further components, e.g. functionalities as defined herein, e.g. by amide formation (e.g. carboxylic acids, sulphonic acids, amines, etc.), by Michael addition (e.g. maleinimide moieties, α,β unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components.

The amino acid component $(AA)_x$ may also occur as a mixed repetitive amino acid component $[(AA)_x]_z$ wherein the number of amino acid components $(AA)_x$ is further defined by z. In this context, z is an integer and may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values. Such a mixed repetitive amino acid component $[(AA)_x]_z$ may be used to integrate several of the same or different amino acid components $(AA)_x$ as defined herein in the inventive polymeric carrier. Preferably, in the mixed repetitive amino acid component $[(AA)_x]_z$ the amino acid component $(AA)_x$ may contain or may be flanked (e.g. terminally) by at least one —SH containing moiety, preferably at least two —SH containing moieties as already defined above, which allows coupling the different amino acid components $(AA)_x$ using a disulfide bond via a condensation polymerization. Likewise as above, the mixed repetitive amino acid component $[(AA)_x]_z$ may also be read as $[S-(AA)_x-S]_z$, wherein S represents a —SH containing moiety, e.g. a cysteine residue. In the specific case that the —SH containing moiety represents a cysteine, the mixed repetitive amino acid component $[(AA)_x]_z$ may also be read as $[Cys-(AA)_x-Cys]_z$, wherein Cys represents Cysteine and provides for the necessary —SH-moiety for a disulfide bond. The —SH containing moiety may be also introduced into the amino acid component $(AA)_x$ using any of modifications or reactions as shown above for components $P^1$, $P^2$ or $P^3$.

The amino acid component $(AA)_x$ or the mixed repetitive amino acid component $[(AA)_x]_z$ may be provided with at least one —SH-moiety, e.g. in a form represented by formula $(AA)_x$-SH. Then, the component $(AA)_x$ according to formula $(AA)_x$-SH or the mixed repetitive amino acid component $[(AA)_x]_z$ according to formula $[(AA)_x]_z$-SH, may be bound to any of components L, $P^1$, $P^2$ and/or $P^3$ or another component $(AA)_x$ via a disulfide bond. If bound to component $P^1$ and/or component $P^3$, components $P^1$ and/or $P^3$ preferably exhibit at least two —SH-moieties to allow further binding of components $P^1$ and/or $P^3$ to a component $P^2$ via a —SH-moiety forming a disulfide bond (see above). The amino acid component $(AA)_x$ in a form represented by formula $(AA)_x$-SH or the mixed repetitive amino acid component $[(AA)_x]_z$ according to formula $[(AA)_x]_z$—SH may be also used to terminate a condensation reaction due to its single —SH moiety. In this case, the amino acid component $(AA)_x$ in a form represented by formula $(AA)_x$-SH is preferably coupled terminally to components $P^1$ and/or $P^3$. The amino acid component $(AA)_x$ in a form represented by formula $(AA)_x$-SH or the mixed repetitive amino acid component $[(AA)_x]_z$ according to formula $[(AA)_x]_z$—SH may be also used to bind internally to any of components L, $P^1$, $P^2$ and/or $P^3$ or a further component $(AA)_x$ via a further internal —SH-moiety of any of components L, $P^1$, $P^2$ and/or $P^3$ or $(AA)_x$.

Furthermore, the amino acid component $(AA)_x$ may be provided with two —SH-moieties (or even more), e.g. in a form represented by formula HS-$(AA)_x$-SH. Additionally, the mixed repetitive amino acid component $[(AA)_x]_z$ may be provided with two —SH-moieties (or even more), e.g. in a form represented by formula HS-$[(AA)_x]_z$—SH, to allow binding to two functionalities via disulfide bonds, e.g. if the amino acid component $(AA)_x$ or the mixed repetitive amino acid component $[(AA)_x]_z$ is used as a linker between two further components (e.g. as a linker between components L and $P^1$, between components $P^1$ and $P^2$, in or as a part of repetitive component $[S-P^2-S]_n$, between components $P^2$ and $P^3$ and/or between components $P^3$ and L). In this case, one —SH moiety is preferably protected in a first step using a protecting group as known in the art, leading to an amino acid component $(AA)_x$ of formula HS-$(AA)_x$-S-protecting group or to a mixed repetitive amino acid component $[(AA)_x]_z$ of formula HS-$[(AA)_x]_z$-S-protecting group. Then, the amino acid component $(AA)_x$ or the mixed repetitive amino acid component MALL may be bound to a component L, $P^1$, $P^2$ and/or $P^3$, to form a first disulfide bond via the non-protected —SH moiety. The protected-SH-moiety is then typically deprotected and bound to a further free —SH-moiety of a further component L, $P^1$, $P^2$ and/or $P^3$ to form a second disulfide bond. In the case that the amino acid component $(AA)_x$ or the mixed repetitive amino acid component MALL is part of the repetitive component $[S-P^2-S]_n$ it is preferred that the formation of the disulfide bonds between $(AA)_x$ and $P^2$ concurrently occurs with the polycondensation reaction of the repetitive component $[S-P^2-S]_n$ and therefore no protection of the at least two terminal —SH-moieties is not necessary.

Alternatively, the amino acid component $(AA)_x$ or the mixed repetitive amino acid component $[(AA)_x]_z$ may be provided with other functionalities as already described above for components $P^1$ and $P^2$ and/or $P^3$, which allow binding of the amino acid component $(AA)_x$ or binding of the mixed repetitive amino acid component $[(AA)_x]_z$ to any of components $P^1$, $P^2$ and/or $P^3$ or $(AA)_x$ and optionally to component L.

Thus, according to the present invention, the amino acid component $(AA)_x$ and/or the mixed repetitive amino acid component $[(AA)_x]_z$ may be bound to $P^1$, $P^2$, $P^3$, $(AA)_x$ and/or L with or without using a disulfide linkage. Binding without using a disulfide linkage may be accomplished by any of the reactions described above, preferably by binding the amino acid component $(AA)_x$ or the mixed repetitive amino acid component $[(AA)_x]_z$ to $P^1$, $P^2$, $P^3$, $(AA)_x$ and/or L using an amid-chemistry as defined herein. If desired or necessary, the other terminus of the amino acid component $(AA)_x$ or the mixed repetitive amino acid component $[(AA)_x]_z$, e.g. the N- or C-terminus, may be used to couple another component, e.g. a ligand L. For this purpose, the other terminus of the amino acid component $(AA)_x$ or the mixed repetitive amino acid component $[(AA)_x]_z$ preferably comprises or is modified to comprise a further functionality, e.g. an alkyn-species (see above), which may be used to add the other component via e.g. click-chemistry. Such a construct, e.g. L-$(AA)_x$-$P^1$—S— or L-$[(AA)_x]_z$-$P^1$—S—, may be used to terminate the polymerization condensation reaction of repetitive component $[S-P^2-S]_n$. If the ligand is bound via an acid-labile bond, the bond may be cleaved off in the endosome and the inventive polymeric carrier presents amino acid component $(AA)_x$ or the mixed repetitive amino acid component $[(AA)_x]_z$ at its surface.

The amino acid component $(AA)_x$ or the mixed repetitive amino acid component $[(AA)_x]_z$ may occur as a further component of generic formula (I) above, e.g. as a linker between components $P^1$ or $P^3$ and $P^2$, as a linker between components L and $P^1$ or $P^2$ or as an additional component of the repetitive component $[S-P^2-S]_n$.

According to a first alternative, such an amino acid component $(AA)_x$ or the mixed repetitive amino acid component $[(AA)_x]_z$ may be present as a linker between components $P^1$ or $P^3$ and component $P^2$. This is preferably represented in the context of the entire inventive polymeric carrier according to formula (I) by following formulae:

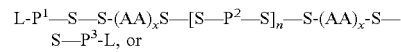

L-$P^1$—S—S-$(AA)_x$S—$[S-P^2-S]_n$—S-$(AA)_x$-S—S—$P^3$-L, or

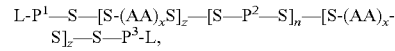

L-$P^1$—S—$[S-(AA)_xS]_z$—$[S-P^2-S]_n$—$[S-(AA)_x-S]_z$—S—$P^3$-L, wherein n, x, z, S, L, AA, $P^1$, $P^2$ and $P^3$ are preferably as defined herein. In the above formulae, the term "—S—S—" represents a disulfide bond, wherein this at least one sulfur of the disulfide bond may also be provided by a cysteine. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" may also be understood generally as "-(Cys-S)—(S-Cys)-", wherein in this specific case S indicates the sulfur of the —SH-moiety of cysteine. Likewise, the terms "—S-Cys" and "—Cys-S" indicate a disulfide bond between a —SH containing moiety and a cysteine, which may also be written as "—S—(S—Cys)" and "-(Cys-S)—S".

According to a second alternative, such an amino acid component $(AA)_x$ or the mixed repetitive amino acid component $[(AA)_x]_z$ may be present as a linker between components $P^1$ or $P^3$ and component L. This is preferably represented in the context of the entire inventive polymeric carrier according to formula (I) by following formulae:

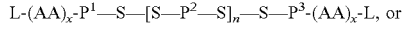
L-$(AA)_x$-$P^1$—S—[S—$P^2$—S]$_n$—S—$P^3$-$(AA)_x$-L, or

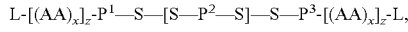
L-$[(AA)_x]_z$-$P^1$—S—[S—$P^2$—S]$_n$—S—$P^3$-$[(AA)_x]_z$-L, or alternatively

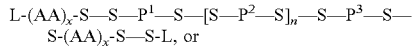
L-$(AA)_x$-S—S—$P^1$—S—[S—$P^2$—S]$_n$—S—$P^3$—S—S-$(AA)_x$-S—S-L, or

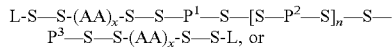
L-S—S-$(AA)_x$-S—S—$P^1$—S—[S—$P^2$—S]$_n$—S—$P^3$—S—S-$(AA)_x$-S—S-L, or

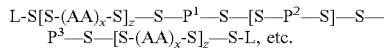
L-S[S-$(AA)_x$-S]$_z$—S—$P^1$—S—[S—$P^2$—S]—S—$P^3$—S—[S-$(AA)_x$-S]$_z$—S-L, etc.

wherein n, x, z, S, L, AA, $P^1$, $P^2$ and $P^3$ are preferably as defined herein. In the above formulae, the term "—S—S—" represents a disulfide bond, as already defined above.

According to a third alternative, such an amino acid component $(AA)_x$ or the mixed repetitive amino acid component $[(AA)_x]_z$ may be present as a part of components $P^1$ and/or $P^3$, wherein the amino acid component $(AA)_x$ may be directly bound to (e.g. the terminus of) component $P^1$ and/or $P^3$ without a further ligand L. In this case the $(AA)_x$ component may be in the form of a ligand as defined above. This is preferably represented in the context of the entire inventive polymeric carrier according to formula (I) by following formulae:

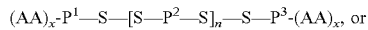
$(AA)_x$-$P^1$—S—[S—$P^2$—S]$_n$—S—$P^3$-$(AA)_x$, or

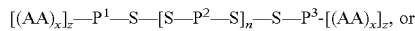
$[(AA)_x]_z$—$P^1$—S—[S—$P^2$—S]$_n$—S—$P^3$-$[(AA)_x]_z$, or or alternatively

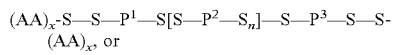
$(AA)_x$-S—S—$P^1$—S[S—$P^2$—S$_n$]—S—$P^3$—S—S-$(AA)_x$, or

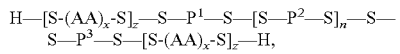
H—[S-$(AA)_x$-S]$_z$—S—$P^1$—S—[S—$P^2$—S]$_n$—S—S—$P^3$—S—[S-$(AA)_x$-S]$_z$—H, wherein n, x, z, S, AA, $P^1$, $P^2$ and $P^3$ are preferably as defined herein. In the above formulae, the term "—S—S—" represents a disulfide bond, as already defined above. The free —SH moiety at the terminal ends in the last formula may also be terminated using a monothiol compound as defined herein.

According to a fourth and particularly preferred alternative, the amino acid component $(AA)_x$, preferably written as S-$(AA)_x$-S or [S-$(AA)_x$-S] may be used to modify component $P^2$, particularly the content of component S—$P^2$—S in repetitive component [S—$P^2$—S]$_n$ of formula (I) above. This may be represented in the context of the entire polymeric carrier according to formula (I) e.g. by following formula (Ia):

L-$P^1$—S—{[S—$P^2$—S]$_a$[S-$(AA)_x$-S]$_b$}—S—$P^3$-L, wherein x, S, L, AA, $P^1$, $P^2$ and $P^3$ are preferably as defined herein. In formula (Ia) above, any of the single components [S—$P^2$—S] and [S-$(AA)_x$-S] may occur in any order in the subformula {[S—$P^2$—S]$_a$[S-$(AA)_x$-S]$_b$}. The numbers of single components [S—$P^2$—S] and [S-$(AA)_x$-S] in the subformula {[S—$P^2$—S]$_a$[S-$(AA)_x$-S]$_b$} are determined by integers a and b, wherein a+b=n. n is an integer and is defined as above for formula (I).

a is an integer, typically selected independent from integer b from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, a is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

b is an integer, typically selected independent from integer a from a range of about 0 to 50 or 1 to 50, preferably from a range of about 0, 1, 2 or 3 to 30, more preferably from a range of about 0, 1, 2, 3, 4, or 5 to 25, or a range of about 0, 1, 2, 3, 4, or 5 to 20, or a range of about 0, 1, 2, 3, 4, or 5 to 15, or a range of about 0, 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, b is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In the above formula, the term "—S—S—" (the brackets are omitted for better readability) represents a disulfide bond as already defined above.

The modification of component $P^2$, particularly of component S—$P^2$—S of repetitive component [S—$P^2$—S]$_n$, by "diluting" same with amino acid components $(AA)_x$ may be also realized in the context of any of the afore mentioned alternatives of the entire polymeric carrier according to formula (I),

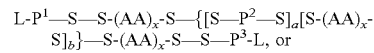
L-$P^1$—S—S-$(AA)_x$-S—{[S—$P^2$—S]$_a$[S-$(AA)_x$-S]$_b$}—S-$(AA)_x$-S—S—$P^3$-L, or

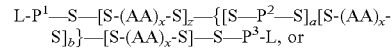
L-$P^1$—S—[S-$(AA)_x$-S]$_z$—{[S—$P^2$—S]$_a$[S-$(AA)_x$-S]$_b$}—[S-$(AA)_x$-S]—S—$P^3$-L, or

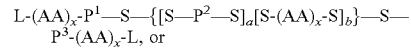
L-$(AA)_x$-$P^1$—S—{[S—$P^2$—S]$_a$[S-$(AA)_x$-S]$_b$}—S—$P^3$-$(AA)_x$-L, or

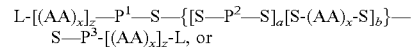
L-$[(AA)_x]_z$—$P^1$—S—{[S—$P^2$—S]$_a$[S-$(AA)_x$-S]$_b$}—S—$P^3$-$[(AA)_x]_z$-L, or

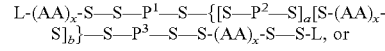
L-$(AA)_x$-S—S—$P^1$—S—{[S—$P^2$—S]$_a$[S-$(AA)_x$-S]$_b$}—S—$P^3$—S—S-$(AA)_x$-S—S-L, or

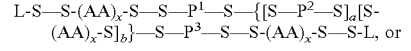
L-S—S-$(AA)_x$-S—S—$P^1$—S—{[S—$P^2$—S]$_a$[S-$(AA)_x$-S]$_b$}—S—$P^3$—S—S-$(AA)_x$-S—S-L, or

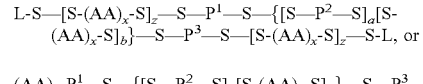
L-S—[S-$(AA)_x$-S]$_z$—S—$P^1$—S—{[S—$P^2$—S]$_a$[S-$(AA)_x$-S]$_b$}—S—$P^3$—S—[S-$(AA)_x$-S]$_z$—S-L, or

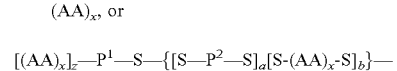
$(AA)_x$-$P^1$—S—{[S—$P^2$—S]$_a$[S-$(AA)_x$-S]$_b$}—S—$P^3$-$(AA)_x$, or

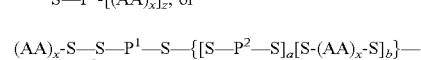
$[(AA)_x]_z$—$P^1$—S—{[S—$P^2$—S]$_a$[S-$(AA)_x$-S]$_b$}—S—$P^3$-$[(AA)_x]_z$, or

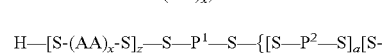
$(AA)_x$-S—S—$P^1$—S—{[S—$P^2$—S]$_a$[S-$(AA)_x$-S]$_b$}—S—$P^3$—S—S-$(AA)_x$, or H—[S-$(AA)_x$-S]$_z$—S—$P^1$—S—{[S—$P^2$—S]$_a$[S-$(AA)_x$-S]$_b$}—S—$P^3$—S—[S-$(AA)_x$-S]$_z$—H, wherein n, x, z, a, b, S, L, AA, $P^1$, $P^2$ and $P^3$ are preferably as defined herein. Likewise, the term "—S—S—" represents a disulfide bond and is preferably as defined herein.

In the above alternatives, wherein the component [S—P²—S] is preferably "diluted" with amino acid components [S-(AA)$_x$-S], the ratio is determined by integers a and b, wherein a+b=n. Preferably, integers a and b are selected such that the cationic binding properties of component [S—P²—S] are not lost but remain to a minimum extent in subformula/component {[S—P²—S]$_a$[S-(AA)$_x$-S]$_b$}. This allows to weaken ("dilute") the cationic binding strength of component [S—P²—S] in repetitive component [S—P²—S]$_n$ of inventive polymeric carrier of formula (I) to a desired extent.

In this specific context the (desired) cationic binding strength of subformula/component {([S—P²—S]$_a$[S-(AA)$_x$-S]$_b$} may be determined using different methods.

According to a first alternative, component P² of formula (I) of the present invention is particularly preferable a cationic or polycationic peptide as defined herein. Furthermore, the amino acid component (AA)$_x$, preferably written as [S-(AA)$_x$-S], typically resembles a peptide sequence. In this specific case, the cationic properties of subformula/component {[S—P²—S]$_a$[S-(AA)$_x$-S]$_b$} may be determined upon their content of cationic amino acids in the entire subformula/component. Preferably, the content of cationic amino acids in subformula/component {[S—P²—S]$_a$[S-(AA)$_x$-S]$_b$} is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the entire subformula/component {[S—P²—S]$_a$[S-(AA)$_x$-S]$_b$} is 100%.

According to a second alternative, component P² of formula (I) of the present invention is particularly preferable a cationic or polycationic polymer as defined herein. The amino acid component (AA)$_x$, preferably written as [S-(AA)$_x$-S], typically resembles a peptide sequence. In this specific case, the cationic properties of subformula/component {[S—P²—S]$_a$[S-(AA)$_x$-S]$_b$} may be determined upon their content of cationic charges in the entire subformula/component. Preferably, the content of cationic charges in subformula/component {[S—P²—S]$_a$[S-(AA)$_x$-S]$_b$} at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even preferably in the range of about 20% to 50%, e.g. 20, 30, 40 or 50%, or in a range formed by any two of the afore mentioned values, provided, that the content of all charges, e.g. positive and negative charges at a (physiological) pH as defined herein, in the entire subformula/component {[S—P²—S]$_a$[S-(AA)$_x$-S]$_b$} is 100%.

In the context of the present invention, the amino acid component (AA)$_x$ may be selected from the following alternatives.

According to a first alternative, the amino acid component (AA)$_x$ may be an aromatic amino acid component (AA)$_x$. The incorporation of aromatic amino acids or sequences as an amino aromatic acid component (AA)$_x$ into the inventive polymeric carrier according to formula (I) of the present invention enables a different (second) binding of the inventive polymeric carrier to the nucleic acid due to interactions of the aromatic amino acids with the bases of the nucleic acid cargo in contrast to the binding thereof by cationic charged sequences of the polymeric carrier molecule to the phosphate backbone. This interaction may occur e.g. by intercalations or by minor or major groove binding. This kind of interaction is not prone to decompaction by anionic complexing partners (e.g. Heparin, Hyaluronic acids) which are found mainly in the extracellular matrix in vivo and is also less susceptible to salt effects.

For this purpose, the amino acid AA in the aromatic amino acid component (AA)$_x$ may be selected from either the same or different aromatic amino acids e.g. selected from Trp, Tyr, or Phe. Alternatively, the amino acid AA (or the entire aromatic amino acid component (AA)$_x$) may be selected from following peptide combinations Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr, Tyr-Trp-Tyr-Trp, Trp-Trp-Trp-Trp, Phe-Tyr, Tyr-Phe, Phe-Phe, Phe-Tyr-Phe, Tyr-Phe-Tyr, Phe-Phe-Phe, Phe-Tyr-Phe-Tyr, Tyr-Phe-Tyr-Phe, Phe-Phe-Phe-Phe, Phe-Trp, Trp-Phe, Phe-Phe, Phe-Trp-Phe, Trp-Phe-Trp, Phe-Trp-Phe-Trp, Trp-Phe-Trp-Phe, or Tyr-Tyr-Tyr-Tyr, etc. (SEQ ID NOs: 85-112) or combinations thereof.

Additionally, the aromatic amino acid component (AA)$_x$ may contain or may be flanked by a —SH containing moiety, which allows introducing this component via a disulfide bond as a further part of generic formula (I) above, e.g. as a linker or more preferably as a component of the repetitive component [S—P²—S]$_n$. Such a —SH containing moiety may be any moiety as defined herein suitable to couple one component as defined herein to a further component as defined herein. As an example, such a —SH containing moiety may be a cysteine. Then, e.g. the aromatic amino acid component (AA)$_x$ may be selected from e.g. peptide combinations Cys-Tyr-Cys, Cys-Trp-Cys, Cys-Trp-Tyr-Cys, Cys-Tyr-Trp-Cys, Cys-Trp-Trp-Cys, Cys-Tyr-Tyr-Cys, Cys-Trp-Tyr-Trp-Cys, Cys-Tyr-Trp-Tyr-Cys, Cys-Trp-Trp-Trp-Cys, Cys-Tyr-Tyr-Tyr-Cys, Cys-Trp-Tyr-Trp-Cys, Cys-Tyr-Trp-Tyr-Trp-Cys, Cys-Trp-Trp-Trp-Trp-Cys, Cys-Tyr-Tyr-Tyr-Tyr-Cys, Cys-Phe-Cys, Cys-Phe-Tyr-Cys, Cys-Tyr-Phe-Cys, Cys-Phe-Phe-Cys, Cys-Tyr-Tyr-Cys, Cys-Phe-Tyr-Phe-Cys, Cys-Tyr-Phe-Tyr-Cys, Cys-Phe-Phe-Phe-Cys, Cys-Tyr-Phe-Tyr-Phe-Cys, Cys-Tyr-Tyr-Tyr-Cys, Cys-Phe-Tyr-Phe-Cys, Cys-Tyr-Phe-Tyr-Phe-Cys, or Cys-Phe-Phe-Phe-Phe-Cys, Cys-Phe-Trp-Cys, Cys-Trp-Phe-Cys, Cys-Trp-Trp-Cys, Cys-Phe-Trp-Phe-Cys, Cys-Trp-Phe-Trp-Cys, Cys-Phe-Trp-Phe-Trp-Cys, Cys-Trp-Phe-Trp-Phe-Cys, etc. (SEQ ID NOs: 113-145) or combinations thereof. Each Cys above may also be replaced by any modified peptide or chemical compound carrying a free —SH-moiety as defined herein.

Additionally, the aromatic amino acid component (AA)$_x$ may contain at least one proline, which may serve as a structure breaker of longer repetitive sequences of Trp, Tyr and Phe in the aromatic amino acid component (AA)$_x$, preferably two, three or more prolines.

According to a second alternative, the amino acid component (AA)$_x$ may be a hydrophilic (and preferably non charged polar) amino acid component (AA)$_x$. The incorporation of hydrophilic (and preferably non charged polar) amino acids or sequences as amino hydrophilic (and preferably non charged polar) acid component (AA)$_x$ into the inventive polymeric carrier according to formula (I) of the present invention enables a more flexible binding to the nucleic acid cargo. This leads to a more effective compaction of the nucleic acid cargo and hence to a better protection against nucleases and unwanted decompaction. It also allows provision of a (long) inventive polymeric carrier according to formula (I) which exhibits a reduced cationic charge over the entire carrier or preferably within repetitive component $[S—P^2—S]_n$ and in this context to better adjusted binding properties, if desired or necessary.

For this purpose, the amino acid AA in the hydrophilic (and preferably non charged polar) amino acid component $(AA)_x$ may be selected from either the same or different hydrophilic (and preferably non charged polar) amino acids e.g. selected from Thr, Ser, Asn or Gln. Alternatively, the amino acid AA (or the entire hydrophilic (and preferably non charged polar) amino acid component $(AA)_x$) may be selected from following peptide combinations Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr, Thr-Ser-Thr-Ser, Ser-Ser-Ser-Ser, Thr-Thr-Thr-Thr, Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. (SEQ ID NOs: 146-181) or combinations thereof.

Additionally, the hydrophilic (and preferably non charged polar) amino acid component $(AA)_x$ may contain or may be flanked by a —SH containing moiety, which allows introducing this component via a disulfide bond as a further part of generic formula (I) above, e.g. as a linker or more preferably as component of the repetitive component $[S—P^2—S]_n$. Such a —SH containing moiety may be any moiety as defined herein suitable to couple one component as defined herein to a further component as defined herein. As an example, such a —SH containing moiety may be a cysteine. Then, e.g. the hydrophilic (and preferably non charged polar) amino acid component $(AA)_x$ may be selected from e.g. peptide combinations Cys-Thr-Cys, Cys-Ser-Cys, Cys-Ser-Thr-Cys, Cys-Thr-Ser-Cys, Cys-Ser-Ser-Cys, Cys-Thr-Thr-Cys, Cys-Ser-Thr-Ser-Cys, Cys-Thr-Ser-Thr-Cys, Cys-Ser-Ser-Ser-Cys, Cys-Thr-Thr-Thr-Cys, Cys-Ser-Thr-Ser-Thr-Cys, Cys-Thr-Ser-Thr-Ser-Cys, Cys-Ser-Ser-Ser-Ser-Cys, Cys-Thr-Thr-Thr-Thr-Cys, Cys-Asn-Cys, Cys-Gln-Cys, Cys-Gln-Asn-Cys, Cys-Asn-Gln-Cys, Cys-Gln-Gln-Cys, Cys-Asn-Asn-Cys, Cys-Gln-Asn-Gln-Cys, Cys-Asn-Gln-Asn-Cys, Cys-Gln-Gln-Gln-Cys, Cys-Asn-Asn-Asn-Cys, Cys-Gln-Asn-Gln-Asn-Cys, Cys-Asn-Gln-Asn-Gln-Cys, Cys-Gln-Gln-Gln-Gln-Cys, Cys-Asn-Asn-Asn-Asn-Cys, Cys-Asn-Cys, Cys-Ser-Cys, Cys-Ser-Asn-Cys, Cys-Asn-Ser-Cys, Cys-Ser-Ser-Cys, Cys-Asn-Asn-Cys, Cys-Ser-Asn-Ser-Cys, Cys-Asn-Ser-Asn-Cys, Cys-Ser-Ser-Ser-Cys, Cys-Asn-Asn-Asn-Cys, Cys-Ser-Asn-Ser-Asn-Cys, Cys-Asn-Ser-Asn-Ser-Cys, Cys-Ser-Ser-Ser-Ser-Cys, or Cys-Asn-Asn-Asn-Asn-Cys, etc. (SEQ ID NOs: 182-223) or combinations thereof. Each Cys above may also be replaced by any modified peptide or chemical compound carrying a free —SH-moiety as defined herein.

Additionally, the hydrophilic (and preferably non charged polar) amino acid component $(AA)_x$ may contain at least one proline, which may serve as a structure breaker of longer repetitive sequences of Ser, Thr and Asn in the hydrophilic (and preferably non charged polar) amino acid component $(AA)_x$, preferably two, three or more prolines.

According to a third alternative, the amino acid component $(AA)_x$ may be a lipophilic amino acid component $(AA)_x$. The incorporation of lipophilic amino acids or sequences as amino lipophilic acid component $(AA))_x$ into the inventive polymeric carrier according to formula (I) of the present invention enables a stronger compaction of the nucleic acid cargo and/or the polymeric carrier according to formula (I) and its nucleic acid cargo when forming a complex. This is particularly due to interactions of one or more polymer strands of the inventive polymeric carrier, particularly of lipophilic sections of lipophilic amino acid component $(AA)_x$, preferably in the context of subformula/component $\{[S—P^2—S]_a[S-(AA)_x-S]_b\}$, and the nucleic acid cargo. This interaction will preferably add an additional stability to the complex between the polymeric carrier according to formula (I) and its nucleic acid cargo. This stabilization may somehow be compared to a sort of non covalent crosslinking between different polymerstrands. Especially in aqueous environment this interaction is typically strong and provides a significant effect.

For this purpose, the amino acid AA in the lipophilic amino acid component $(AA)_x$ may be selected from either the same or different lipophilic amino acids e.g. selected from Leu, Val, Ile, Ala, Met. Alternatively, the amino acid AA (or the entire lipophilic amino acid component $(AA)_x$) may be selected from following peptide combinations Leu-Val, Val-Leu, Leu-Leu, Val-Val, Leu-Val-Leu, Val-Leu-Val, Leu-Leu-Leu, Val-Val-Val, Leu-Val-Leu-Val, Val-Leu-Val-Leu, Leu-Leu-Leu-Leu, Val-Val-Val-Val, Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala, Ala-Ile-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. (SEQ ID NOs: 224-258) or combinations thereof.

Additionally, the lipophilic amino acid component $(AA)_x$ may contain or may be flanked by a —SH containing moiety, which allows introducing this component via a disulfide bond as a further part of generic formula (I) above, e.g. as a linker or more preferably as component of the repetitive component $[S—P^2—S]_n$. Such a —SH containing moiety may be any moiety as defined herein suitable to couple one component as defined herein to a further component as defined herein. As an example, such a —SH containing moiety may be a cysteine. Then, e.g. the lipophilic amino acid component $(AA)_x$ may be selected from e.g. peptide combinations Cys-Val-Cys, Cys-Leu-Cys, Cys-Leu-Val-Cys, Cys-Val-Leu-Cys, Cys-Leu-Leu-Cys, Cys-Val-Val-Cys, Cys-Leu-Val-Leu-Cys, Cys-Val-Leu-Val-Cys, Cys-Leu-Leu-Leu-Cys, Cys-Val-Val-Val-Cys, Cys-Leu-Val-Leu-Val-Cys, Cys-Val-Leu-Val-Leu-Cys, Cys-Leu-Leu-Leu-Leu-Cys, Cys-Val-Val-Val-Val-Cys, Cys-Ala-Cys, Cys-Ile-Cys, Cys-Ile-Ala-Cys, Cys-Ala-Ile-Cys, Cys-Ile-Ile-Cys, Cys-Ala-Ala-Cys, Cys-Ile-Ala-Ile-Cys, Cys-Ala-Ile-Ala-Cys, Cys-Ile-Ile-Ile-Cys, Cys-Ala-Ala-Ala-Cys, Cys-Ile-Ala-Ile-Ala-Cys, Cys-Ala-Ile-Ala-Ile-Cys, Cys-Ile-Ile-Ile-Ile-Cys, or Cys-Ala-Ala-Ala-Ala-Cys, Cys-Met-Cys, Cys-Met-Ala-Cys, Cys-Ala-Met-Cys, Cys-Met-Met-Cys, Cys-Ala-Ala-Cys, Cys-Met-Ala-Met-Cys, Cys-Ala-Met-Ala-Cys, Cys-Met-Met-Met-Cys, Cys-Ala-Ala-Ala-Cys, Cys-Met-Ala-Met-Ala-Cys, Cys-Ala-Met-Ala-Met-Cys, Cys-Met-Met-Met-Met-Cys, or Cys-Ala-Ala-Ala-Ala-Cys, etc. (SEQ ID NOs: 289-299) or combinations thereof. Each Cys above may also be replaced by any modified peptide or chemical compound carrying a free —SH-moiety as defined herein.

Additionally, the lipophilic amino acid component $(AA)_x$ may contain at least one proline, which may serve as a structure breaker of longer repetitive sequences of Leu, Val, Ile, Ala and Met in the lipophilic amino acid component $(AA)_x$, preferably two, three or more prolines.

According to a fourth alternative, the amino acid component $(AA)_x$ may be a weak basic amino acid component $(AA)_x$. The incorporation of weak basic amino acids or sequences as weak basic amino acid component $(AA)_x$ into the inventive polymeric carrier according to formula (I) of the present invention may serve as a proton sponge and facilitates endosomal escape (also called endosomal release) (proton sponge effect). Incorporation of such a weak basic amino acid component $(AA)_x$ preferably enhances transfection efficiency.

For this purpose, the amino acid AA in the weak basic amino acid component $(AA)_x$ may be selected from either the same or different weak amino acids e.g. selected from histidine or aspartate (aspartic acid). Alternatively, the weak basic amino acid AA (or the entire weak basic amino acid component $(AA)_x$) may be selected from following peptide combinations Asp-His, His-Asp, Asp-Asp, His-His, Asp-His-Asp, His-Asp-His, Asp-Asp-Asp, His-His-His, Asp-His-Asp-His, His-Asp-His-Asp, Asp-Asp-Asp-Asp, or His-His-His-His, etc. (SEQ ID NOs: 300-311) or combinations thereof.

Additionally, the weak basic amino acid component $(AA)_x$ may contain or may be flanked by a —SH containing moiety, which allows introducing this component via a disulfide bond as a further part of generic formula (I) above, e.g. as a linker or more preferably as component of the repetitive component $[S-P^2-S]_n$. Such a —SH containing moiety may be any moiety as defined herein suitable to couple one component as defined herein to a further component as defined herein. As an example, such a —SH containing moiety may be a cysteine. Then, e.g. the weak basic amino acid component $(AA)_x$, may be selected from e.g. peptide combinations Cys-His-Cys, Cys-Asp-Cys, Cys-Asp-His-Cys, Cys-His-Asp-Cys, Cys-Asp-Asp-Cys, Cys-His-His-Cys, Cys-Asp-His-Asp-Cys, Cys-His-Asp-His-Cys, Cys-Asp-Asp-Asp-Cys, Cys-His-His-His-Cys, Cys-Asp-His-Asp-His-Cys, Cys-His-Asp-His-Asp-Cys, Cys-Asp-Asp-Asp-Asp-Cys, or Cys-His-His-His-His-Cys, etc. (SEQ ID NOs: 312-325) or combinations thereof. Each Cys above may also be replaced by any modified peptide or chemical compound carrying a free —SH-moiety as defined herein.

Additionally, the weak basic amino acid component $(AA)_x$ may contain at least one proline, which may serve as a structure breaker of longer repetitive sequences of histidine or aspartate (aspartic acid) in the weak basic amino acid component $(AA)_x$, preferably two, three or more prolines.

Additionally, the inventive polymeric carrier according to formula (I) above (or according to any of its subformulas herein), may comprise as an additional component, preferably as a ligand L or as an amino acid component $(AA)_x$ a signal peptide, a localization signal or sequence or a nuclear localization signal or sequence (NLS), which allows a translocalization of the inventive polymeric carrier according to formula (I) above to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytosceleton, etc. Such a signal peptide, localization signal or sequence or nuclear localization signal may be used for the transport of any of the herein defined nucleic acids, preferably an RNA or a DNA, more preferably an shRNA or a pDNA, e.g. into the nucleus. Without being limited thereto, such a signal peptide, localization signal or sequence or nuclear localization signal may comprise, e.g., localisation sequences for the endoplasmic reticulum. Particular localization signals or sequences or nuclear localization signals may include e.g. KDEL (SEQ ID NO: 326), DDEL (SEQ ID NO: 327), DEEL (SEQ ID NO: 328), QEDL (SEQ ID NO: 329), RDEL (SEQ ID NO: 330), and GQNLSTSN (SEQ ID NO: 331), nuclear localisation sequences, including PKK-KRKV (SEQ ID NO: 332), PQKKIKS (SEQ ID NO: 333), QPKKP (SEQ ID NO: 334), RKKR (SEQ ID NO: 335), RKKRRQRRRAHQ (SEQ ID NO: 336), RQARRN-RRRRWRERQR (SEQ ID NO: 337), MPL-TRRRPAASQALAPPTP (SEQ ID NO: 338), GAALTILV (SEQ ID NO: 339), and GAALTLLG (SEQ ID NO: 340), localisation sequences for the endosomal compartment, including MDDQRDLISNNEQLP (SEQ ID NO: 341), localisation sequences for the mitochondrial matrix, including MLFNLRXXLNNAAFRHGHNFMVRNFRCGQPLX (SEQ ID NO: 342), localisation sequences for the plasma membrane: GCVCSSNP (SEQ ID NO: 343), GQTVTTPL (SEQ ID NO: 344), GQELSQHE (SEQ ID NO: 345), GNSPSYNP (SEQ ID NO: 346), GVSGSKGQ (SEQ ID NO: 347), GQTITTPL (SEQ ID NO: 348), GQTLTTPL (SEQ ID NO: 349), GQIFSRSA (SEQ ID NO: 350), GQI-HGLSP (SEQ ID NO: 351), GARASVLS (SEQ ID NO: 352), and GCTLSAEE (SEQ ID NO: 353), localisation sequences for the endoplasmic reticulum and the nucleus, including GAQVSSQK (SEQ ID NO: 354), and GAQLSRNT (SEQ ID NO: 355), localisation sequences for the Golgi apparatus, the nucleus, the cytoplasm and the cytosceleton, including GNAAAAKK (SEQ ID NO: 356), localisation sequences for the cytoplasm and cytosceleton, including GNEASYPL (SEQ ID NO: 357), localisation sequences for the plasma membrane and cytosceleton, including GSSKSKPK (SEQ ID NO: 358), etc. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulines as defined herein, signal sequences of the invariant chain of immunoglobulines or antibodies as defined herein, signal sequences of Lamp1, Tapasin, Erp57, Calretikulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention. Most preferably such an additional component may occur as component L as defined herein. Alternatively, such an additional component may also be bound e.g. to a component L, $P^1$, $P^2$, r $P^3$ or $(AA)_x$ as defined herein, e.g. to a side chain of any of components L, $P^1$, $P^2$, $P^3$ or $(AA)_x$, preferably via a side chain of component $P^2$, or optionally as a linker between components L and $P^1$ or $P^3$ and L. The binding to any of components L, $P^1$, $P^2$, or $P^3$ may also be accomplished using an acid-labile bond, preferably via a side chain of any of components L, $P^1$, $P^2$, $P^3$, which allows to detach or release the additional component at lower pH-values, e.g. at physiological pH-values as defined herein.

Additionally, the inventive polymeric carrier according to formula (I) above (or according to any of its subformulas herein), may comprise further functional peptides or proteins preferably as ligand or amino acid component $(AA)_x$, which may modulate the functionality of the inventive polymeric carrier accordingly. According to one alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the inventive polymeric carrier (in complex with a nucleic acid) from the endosome by insertion into the lipid layer of the liposome. Such called cell penetrating peptides (CPPs) or cationic peptides for transportation, may include, without being limited thereto protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila antennapecha*), pAntp, plsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc. Likewise, such an additional component L or $(AA)_x$, as defined herein. Alternatively, such an additional component may also be bound to a component L, $P^1$, $P^2$, $P^3$ or $(AA)_x$, as defined herein, e.g. to a side chain of any of components L, $P^1$, $P^2$, $P^3$, or $(AA)_x$, preferably via a side chain of component $P^2$, or optionally as a linker between components L and $P^1$ or $P^3$ and L. The binding to any of components L, $P^1$, $P^2$, $P^3$ or $(AA)_x$ may also be accomplished using an acid-labile bond, preferably via a side chain of any of components L, $P^1$, $P^2$, $P^3$, or $(AA)_x$ which allows to detach or release the additional component at lower pH-values, e.g. at physiological pH-values as defined herein. In this context it is particularly preferred that this additional component occurs as ligand L or as amino acid component $(AA)_x$ of the repetitive component $[S—P^2—S]_n$ of formula (I).

According to a last alternative, the inventive polymeric carrier according to formula (I) above (or according to any of its subformulas herein), may comprise as an additional component, preferably as amino acid component $(AA)_x$, any peptide or protein which can execute any favorable function in the cell. Particularly preferred are peptides or proteins selected from therapeutically active proteins or peptides, from antigens, e.g. tumour antigens, pathogenic antigens (animal antigens, viral antigens, protozoal antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application as defined below for coding nucleic acids. Particularly preferred are peptide epitopes from antigens as defined herein. Likewise, such an additional component may occur preferably as $(AA)_x$ as defined herein. Alternatively, such an additional component may also be bound to a component L, $P^1$, $P^2$, $P^3$ or $(AA)_x$ as defined herein, e.g. to a side chain of any of components L, $P^1$, $P^2$, $P^3$, or $(AA)_x$, preferably via a side chain of component $P^2$, or optionally as a linker between components L and $P^1$ or $P^3$ and L. The binding to any of components L, $P^1$, $P^2$, $P^3$ or $(AA)_x$ may also be accomplished using an acid-labile bond, preferably via a side chain of any of components L, $P^1$, $P^2$, $P^3$, or $(AA)_x$ which allows to detach or release the additional component at lower pH-values, e.g. at physiological pH-values as defined herein. In this context it is particularly preferred that this additional component occurs as amino acid component $(AA)_x$ of the repetitive component $[S—P^2—S]_n$ of formula (I).

The inventive polymeric carrier according to formula (I) may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

The object underlying the present invention is furthermore solved according to a second embodiment of the present invention by the inventive polymeric carrier cargo complex formed by the nucleic acid cargo and a polymeric carrier molecule according to generic formula (I) L-$P^1$—S—[S—$P^2$—S]$_n$—S—$P^3$-L as defined herein (or according to any of its subformulas as defined herein). This complex may also be termed "complexed nucleic acid" for the purposes of the present application.

In the inventive polymeric carrier cargo complex, the polymeric carrier molecule according to generic formula (I) L-$P^1$—S—[S—$P^2$—S]$_n$—S—$P^3$-L as defined herein (or according to any of its subformulas herein) and the nucleic acid cargo are typically provided in a molar ratio of about 5 to 10000, preferably in a molar ratio of about 5 to 5000, more preferably in a molar ratio of about 5 to 2500, even more preferably in a molar ratio of about 5 to 2000, and most preferably in a molar ratio of about 5 to 1000 of inventive polymeric carrier molecule:nucleic acid, or in a molar ratio of about 50 to 1000 of inventive polymeric carrier molecule: nucleic acid, e.g. in a molar ratio of about 10 to 5000, in a molar ratio of about 20 to 2500, in a molar ratio of about 25 to 2000 of inventive polymeric carrier molecule:nucleic acid.

Furthermore, in the inventive polymeric carrier cargo complex, the polymeric carrier molecule according to generic formula (I) L-$P^1$—S—[S—$P^2$—S]$_n$—S—$P^3$-L as defined herein (or according to any of its subformulas herein) and the nucleic acid cargo are preferably provided in an N/P-ratio of about 0.1 to 20, preferably in an N/P-ratio of about 0.2 to 12, and even more preferably in an N/P-ratio of about 0.4 to 10 or 0.6 to 5. In this context, an N/P-ratio is defined as the nitrogen/phosphate ratio (N/P-ratio) of the entire inventive polymeric carrier cargo complex. This is typically illustrative for the content/amount of peptides, if peptides are used, in the inventive polymeric carrier and characteristic for the content/amount of nucleic acids bound or complexed in the inventive polymeric carrier cargo complex. It may be calculated on the basis that, for example, 1 µg RNA typically contains about 3 nmol phosphate residues, provided that the RNA exhibits a statistical distribution of bases. Additionally, 1 µg peptide typically contains about x*1 µg/M (peptide) nmol nitrogen residues, dependent on the molecular weight and the number x of its (cationic) amino acids.

In the context of the present invention such a nucleic acid cargo of the inventive polymeric carrier cargo complex formed by the nucleic acid cargo and a polymeric carrier molecule according to generic formula (I) (or according to any of its subformulas herein) may be any suitable nucleic acid, selected e.g. from any DNA, preferably, without being limited thereto, e.g. genomic DNA, single-stranded DNA molecules, double-stranded DNA molecules, coding DNA, DNA primers, DNA probes, a pDNA, immunostimulating DNA or may be selected e.g. from any PNA (peptide nucleic acid) or may be selected e.g. from any RNA, preferably, without being limited thereto, a coding RNA, a messenger RNA (mRNA), an siRNA, an shRNA, an antisense RNA, or riboswitches, immunostimulating RNA (isRNA) ribozymes or aptamers; etc. The nucleic acid may also be a ribosomal RNA (rRNA), a transfer RNA (tRNA), a messenger RNA (mRNA), or a viral RNA (vRNA). Preferably, the nucleic acid is RNA, more preferably a coding RNA. Even more preferably, the nucleic acid may be a (linear) single-stranded RNA, even more preferably an mRNA. In the context of the present invention, an mRNA is typically an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. an RNA which carries the coding sequences of one, two or more (identical or different) proteins or peptides as defined herein. Such coding sequences in di-, or even multicistronic mRNA may be separated by at least one IRES (internal ribosomal entry site) sequence.

Furthermore, the nucleic acid of the inventive polymeric carrier cargo complex formed by the nucleic acid cargo and a polymeric carrier molecule according to generic formula (I) (or according to any of its subformulas herein) may be a single- or a double-stranded nucleic acid (molecule) (which may also be regarded as a nucleic acid (molecule) due to non-covalent association of two single-stranded nucleic acid(s) (molecules)) or a partially double-stranded or partially single stranded nucleic acid, which are at least partially self complementary (both of these partially double-stranded or partially single stranded nucleic acid molecules are typically formed by a longer and a shorter single-stranded nucleic acid molecule or by two single stranded nucleic acid molecules, which are about equal in length, wherein one single-stranded nucleic acid molecule is in part complementary to the other single-stranded nucleic acid molecule and both thus form a double-stranded nucleic acid molecule in this region, i.e. a partially double-stranded or partially single stranded nucleic acid (molecule). Preferably, the nucleic acid (molecule) may be a single-stranded nucleic acid molecule. Furthermore, the nucleic acid (molecule) may be a circular or linear nucleic acid molecule, preferably a linear nucleic acid molecule.

Coding Nucleic Acids:

The nucleic acid molecule of the inventive polymeric carrier cargo complex may encode a protein or a peptide, which may be selected, without being restricted thereto, e.g. from therapeutically active proteins or peptides, selected e.g. from adjuvant proteins, from antigens, e.g. tumour antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, or from any other protein or peptide suitable for a specific (therapeutic) application, wherein the coding nucleic acid may be transported into a cell, a tissue or an organism and the protein may be expressed subsequently in this cell, tissue or organism.

The coding region of the nucleic acid molecule of the inventive polymeric carrier cargo complex may occur as a mono-, di-, or even multicistronic nucleic acid, i.e. a nucleic acid which carries the coding sequences of one, two or more proteins or peptides. Such coding sequences in di-, or even multicistronic nucleic acids may be separated by at least one internal ribosome entry site (IRES) sequence, or by signal peptides which induce the cleavage of the resulting polypeptide which comprises several proteins or peptides.

In particular preferred aspects the encoded peptides or proteins are selected from human, viral, bacterial, protozoan proteins or peptides.

a) Therapeutically Active Proteins

In the context of the present invention, therapeutically active proteins or peptides may be encoded by the nucleic acid molecule of the herein defined inventive polymeric carrier cargo complex. Therapeutically active proteins are defined herein as proteins which have an effect on healing, prevent prophylactically or treat therapeutically a disease, preferably as defined herein, or are proteins of which an individual is in need of. These may be selected from any naturally or synthetically designed occurring recombinant or isolated protein known to a skilled person from the prior art. Without being restricted thereto therapeutically active proteins may comprise proteins, capable of stimulating or inhibiting the signal transduction in the cell, e.g. cytokines, lymphokines, monokines, growth factors, receptors, signal transduction molecules, transcription factors, etc; anticoagulants; antithrombins; antiallergic proteins; apoptotic factors or apoptosis related proteins, therapeutic active enzymes and any protein connected with any acquired disease or any hereditary disease.

A therapeutically active protein, which may be encoded by the nucleic acid molecule of the herein defined inventive polymeric carrier cargo complex, may also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. More preferably, the adjuvant protein is selected from human adjuvant proteins or from pathogenic adjuvant proteins, selected from the group consisting of, without being limited thereto, bacterial proteins, protozoan proteins, viral proteins, or fungal proteins, animal proteins, in particular from bacterial adjuvant proteins. In addition, nucleic acids encoding human proteins involved in adjuvant effects (e.g. ligands of pattern recognition receptors, pattern recoginition receptors, proteins of the signal transduction pathways, transcription factors or cytokines) may be used as well.

b) Antigens

The nucleic acid molecule of the herein defined inventive polymeric carrier cargo complex may alternatively encode an antigen. According to the present invention, the term "antigen" refers to a substance which is recognized by the immune system and is capable of triggering an antigen-specific immune response, e.g. by formation of antibodies or antigen-specific T-cells as part of an adaptive immune response. In this context an antigenic epitope, fragment or peptide of a protein means particularly B cell and T cell epitopes which may be recognized by B cells, antibodies or T cells respectively.

In the context of the present invention, antigens as encoded by the nucleic acid molecule of the herein defined inventive polymeric carrier cargo complex typically comprise any antigen, antigenic epitope or antigenic peptide, falling under the above definition, more preferably protein and peptide antigens, e.g. tumour antigens, allergenic antigens, auto-immune self-antigens, pathogenic antigens, etc. In particular antigens as encoded by the nucleic acid molecule of the herein defined inventive polymeric carrier cargo complex may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens, allergenic antigens, etc. Allergenic antigens (allergy antigens) are typically antigens, which cause an allergy in a human and may be derived from either a human or other sources. Additionally, antigens as encoded by the nucleic acid molecule of the herein defined inventive polymeric carrier cargo complex may be furthermore antigens generated inside the cell, the tissue or the body. Such antigens include antigens derived from the host organism (e.g. a human) itself, e.g. tumour antigens, self-antigens or auto-antigens, such as auto-immune self-antigens, etc., but also (non-self) antigens as defined herein, which have been originally been derived from host cells outside the host organism, but which are fragmented or degraded inside the body, tissue or cell, e.g. by (protease) degradation, metabolism, etc.

One class of antigens as encoded by the nucleic acid molecule of the herein defined inventive polymeric carrier cargo complex comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies.

According to a preferred aspect, such tumor antigens as encoded by the nucleic acid of the inventive polymeric carrier cargo complex are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CAl25, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gpl 00, GPC3, GPNMB/m, HAGE, HAST-2, hepsin, Her2/neu, HERV-K-MEL, HLA-A*0201-R171, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, MEl/m, mesothelin, MG50/PXDN, MMP11, MN/CA IX-antigen, MRP-3, MUC-1, MUC-2, MUM-1/m, MUM-2/m, MUM-3/m, myosin class l/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Spl 7, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRll, TGM-4, TPI/m, TRAG-3, TRG, TRP-1, TRP-2/6b, TRP/INT2, TRP-p8, tyrosinase, UPA, VEGF, VEGFR-2/FLK-1, and WT1, or a fragment, variant or epitope thereof. Epitopes typically comprise 5 to 15, preferably 5 to 12, more preferably 6 to 9 amino acids of the antigen, preferably in its native form.

According to another alternative, one further class of antigens as encoded by the nucleic acid molecule of the herein defined inventive polymeric carrier cargo complex comprises allergenic antigens. Such allergenic antigens may be selected from antigens derived from different sources, e.g. from animals, plants, fungi, bacteria, etc. Allergens in this context include e.g. grasses, pollens, molds, drugs, or numerous environmental triggers, etc. Allergenic antigens typically belong to different classes of compounds, such as nucleic acids and their fragments, proteins or peptides and their fragments, carbohydrates, polysaccharides, sugars, lipids, phospholipids, etc. Of particular interest in the context of the present invention are antigens, which may be encoded by the nucleic acid molecule of the inventive polymeric carrier cargo complex, i.e. protein or peptide antigens and their fragments or epitopes, or nucleic acids and their fragments, particularly nucleic acids and their fragments, encoding such protein or peptide antigens and their fragments or epitopes.

c) Antibodies

According to a further alternative, the nucleic acid molecule of the herein defined inventive polymeric carrier cargo complex may encode an antibody or an antibody fragment. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, the term "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$.

In the context of the present invention, antibodies as encoded by the nucleic acid molecule of the herein defined inventive polymeric carrier cargo complex may preferably comprise full-length antibodies, i.e. antibodies composed of the full heavy and full light chains, as described above. However, derivatives of antibodies such as antibody fragments, variants or adducts may also be encoded by the nucleic acid molecule of the herein defined inventive polymeric carrier cargo complex. Antibody fragments are preferably selected from Fab, Fab', F(ab')$_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

In the present context it is preferable that the different chains of the antibody or antibody fragment are encoded by a multicistronic nucleic acid molecule. Alternatively, the different strains of the antibody or antibody fragment are encoded by several monocistronic nucleic acid(s) (sequences).

siRNA:

According to a further alternative, the nucleic acid of the inventive polymeric carrier cargo complex formed by the nucleic acid cargo and a polymeric carrier molecule according to generic formula (I) (or according to any of its subformulas herein) may be in the form of dsRNA, preferably siRNA. A dsRNA, or a siRNA, is of interest particularly in connection with the phenomenon of RNA interference. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

The nucleic acid of the inventive polymeric carrier cargo complex may thus be a double-stranded RNA (dsRNA) having a length of from 17 to 29, preferably from 19 to 25, and preferably being at least 90%, more preferably 95% and especially 100% (of the nucleotides of a dsRNA) complementary to a section of the nucleic acid sequence of a (therapeutically relevant) protein or antigen described (as active ingredient) hereinbefore, either a coding or a non-coding section, preferably a coding section. 90% complementary means that with a length of a dsRNA described herein of, for example, 20 nucleotides, this contains not more than 2 nucleotides without corresponding complementarity with the corresponding section of the mRNA. The sequence of the double-stranded RNA used according to the invention as the nucleic acid of the inventive polymeric carrier cargo complex is, however, preferably wholly complementary in its general structure with a section of the nucleic acid of a therapeutically relevant protein or antigen described hereinbefore. In this context the nucleic acid of the inventive polymeric carrier cargo complex formed by the nucleic acid cargo and a polymeric carrier molecule according to generic formula (I) may be a dsRNA having the general structure 5'-($N_{17-29}$)-3', preferably having the general structure 5'-($N_{19-25}$)-3', more preferably having the general structure 5'-($N_{19-24}$)-3', or yet more preferably having the general structure 5'-($N_{21-23}$)-3', wherein for each general structure each N is a (preferably different) nucleotide of a section of the mRNA of a therapeutically relevant protein or antigen described hereinbefore, preferably being selected from a continuous number of 17 to 29 nucleotides of the mRNA of a therapeutically relevant protein or antigen and being present in the general structure 5'-($N_{1-29}$)-3' in their natural order. In principle, all the sections having a length of from 17 to 29, preferably from 19 to 25, base pairs that occur in the coding region of the mRNA can serve as target sequence for a dsRNA herein. Equally, dsRNAs used as nucleic acid of the inventive polymeric carrier cargo complex can also be directed against nucleotide sequences of a (therapeutically relevant) protein or antigen described (as active ingredient) hereinbefore that do not lie in the coding region, in particular in the 5' non-coding region of the mRNA, for example, therefore, against non-coding regions of the mRNA having a regulatory function. The target sequence of the dsRNA used as nucleic acid of the inventive polymeric carrier cargo complex can therefore lie in the translated and untranslated region of the mRNA and/or in the region of the control elements of a protein or antigen described hereinbefore. The target sequence of a dsRNA used as nucleic acid of the inventive polymeric carrier cargo complex can also lie in the overlapping region of untranslated and translated sequence; in particular, the target sequence can comprise at least one nucleotide upstream of the start triplet of the coding region of the mRNA.

Immunostimulatory Nucleic Acids:

a) Immunostimulatory CpG Nucleic Acids:

According to another alternative, the nucleic acid of the inventive polymeric carrier cargo complex formed by the nucleic acid cargo and a polymeric carrier molecule according to generic formula (I) (or according to any of its subformulas herein) may be in the form of a a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

b) Immunostimulatory RNA (isRNA):

Likewise, according to a further alternative, the nucleic acid of the inventive polymeric carrier cargo complex formed by the nucleic acid cargo and a polymeric carrier molecule according to generic formula (I) (or according to any of its subformulas herein) may be in the form of a of an immunostimulatory RNA (isRNA), which preferably elicits an innate immune response. Such an immunostimulatory RNA may be any (double-stranded or single-stranded) RNA, e.g. a coding RNA, as defined herein. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1)) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1 TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc NatlAcadSci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (isRNA) used as the nucleic acid molecule of the inventive polymeric carrier cargo complex formed by the nucleic acid cargo and a polymeric carrier molecule according to generic formula (I) (or according to any of its subformulas herein) may thus comprise any RNA sequence known to be immunostimulatory, including, without being limited thereto, RNA sequences representing and/or encoding ligands of TLRs, preferably selected from human family members TLR1 TLR10 or murine family members TLR1 TLR13, more preferably selected from (human) family members TLR1 TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules, used as the nucleic acid molecule of the inventive polymeric carrier cargo complex may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred aspect of this embodiment of the present invention, such immunostimulatory nucleic acid sequences particularly isRNA consist of or comprise a nucleic acid of formula (III) or (IV):

$$G_l X_m G_n \quad \text{(formula (III))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n \quad \text{(formula (IV))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

The nucleic acids of formula (III) or (IV), which may be used as the nucleic acid cargo of the inventive polymeric carrier cargo complex may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of the inventive nucleic acid cargo complex has a maximum length of e.g. 100 nucleotides, m will typically be <=98. The number of nucleotides G in the nucleic acid of formula (III) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_l$ or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (III) according to the invention is preferably not a uracil. Similarly, the number of nucleotides C in the nucleic acid of formula (IV) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_l$ or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (IV) according to the invention is preferably not a uracil. Preferably, for formula (III), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15.

The lower limit of l or n can be varied if necessary and is at least 1, preferably at least 2, more preferably at least 3, 4, 5, 6, 7, 8, 9 or 10. This definition applies correspondingly to formula (IV).

According to a further particularly preferred aspect of this embodiment, such immunostimulatory nucleic acid sequences particularly isRNA consist of or comprise a nucleic acid of formula (V) or (VI):

$$(N_u G_l X_m G_n N_v)_a, \quad \text{(formula (V))}$$

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, G is guanosine (guanine) or an analogue thereof, when l>1, at least 50% of these nucleotides (nucleosides) are guanosine (guanine) or an analogue thereof;
m is an integer and is at least 3;
  wherein when m=3, X is uridine (uracil) or an analogue thereof, and
  when m>3, at least 3 successive uridines (uracils) or analogues of uridine (uracil) occur;

n is an integer from 1 to 40,
  wherein when n=1, G is guanosine (guanine) or an analogue thereof,
    when n>1, at least 50% of these nucleotides (nucleosides) are guanosine (guanine) or an analogue thereof;
u,v may be independently from each other an integer from 0 to 50,
  preferably wherein when u=0, v≥1, or
    when v=0, u≥1;
wherein the nucleic acid molecule of formula (V) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a \quad \text{(formula (VI))}$$

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, C is cytidine (cytosine) or an analogue thereof,
    when l>1, at least 50% of these nucleotides (nucleosides) are cytidine (cytosine) or an analogue thereof;
m is an integer and is at least 3;
  wherein when m=3, X is uridine (uracil) or an analogue thereof,
    when m>3, at least 3 successive uridines (uracils) or analogues of uridine (uracil) occur;
n is an integer from 1 to 40,
  wherein when n=1, C is cytidine (cytosine) or an analogue thereof,
    when n>1, at least 50% of these nucleotides (nucleosides) are cytidine (cytosine) or an analogue thereof.
u, v may be independently from each other an integer from 0 to 50,
  preferably wherein when u=0, v≥1, or
    when v=0, u≥1;
wherein the nucleic acid molecule of formula (VI) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (VI), any of the definitions given above for elements N (i.e. $N_u$ and $N_v$) and X ($X_m$), particularly the core structure as defined above, as well as for integers a, l, m, n, u and v, similarly apply to elements of formula (V) correspondingly, wherein in formula (VI) the core structure is defined by $C_l X_m C_n$. The definition of bordering elements $N_u$ and $N_v$ is identical to the definitions given above for $N_u$ and $N_v$.

According to a very particularly preferred aspect of this embodiment, the inventive nucleic acid molecule according to formula (V) may be selected from e.g. any of the following sequences:

```
                                                  (SEQ ID NO: 359)
UAGCGAAGCUCUUGGACCUAGGUUUUUUUUUUUUUUUGGGUGCGUUCCUAGAAGUACACG (SEQ ID NO: 360)
UAGCGAAGCUCUUGGACCUAGGUUUUUUUUUUUUUUUGGGUGCGUUCCUAGAA

GUACACGAUCGCUUCGAGAACCUGGAUCCAAAAAAAAAAAAAAAACCCACGCAAGGA

UCUUCAUGUGC (SEQ ID NO: 361)
GGGAGAAAGCUCAAGCUUGGAGCAAUGCCCGCACAUUGAGGAAACCGAGUUGCAU

AUCUCAGAGUAUUGGCCCCCGUGUAGGUUAUUCUUGACAGACAGUGGAGCUUAU

UCACUCCCAGGAUCCGAGUCGCAUACUACGGUACUGGUGACAGACCUAGGUCGUC

AGUUGACCAGUCCGCCACUAGACGUGAGUCCGUCAAAGCAGUUAGAUGUUACACU

CUAUUAGAUC (SEQ ID NO: 362)
GGGAGAAAGCUCAAGCUUGGAGCAAUGCCCGCACAUUGAGGAAACCGAGUUGCAU

AUCUCAGAGUAUUGGCCCCCGUGUAGGUUAUUCUUGACAGACAGUGGAGCUUAU

UCACUCCCAGGAUCCGAGUCGCAUACUACGGUACUGGUGACAGACCUAGGUCGUC

AGUUGACCAGUCCGCCACUAGACGUGAGUCCGUCAAAGCAGUUAGAUGUUACACU

CUAUUAGAUCUCGGAUUACAGCUGGAAGGAGCAGGAGUAGUGUUCUUGCUCUAA

GUACCGAGUGUGCCCAAUACCCGAUCAGCUUAUUAACGAACGGCUCCUCCUCUUA
```

-continued

GACUGCAGCGUAAGUGCGGAAUCUGGGGAUCAAAUUACUGACUGCCUGGAUUAC

CCUCGGACAUAUAACCUUGUAGCACGCUGUUGCUGUAUAGGUGACCAACGCCCAC

UCGAGUAGACCAGCUCUCUUAGUCCGGACAAUGAUAGGAGGCGCGGUCAAUCUAC

UUCUGGCUAGUUAAGAAUAGGCUGCACCGACCUCUAUAAGUAGCGUGUCCUCUAG (SEQ ID NO: 363)
GGGAGAAAGCUCAAGCUUGGAGCAAUGCCCGCACAUUGAGGAAACCGAGUUGCAU

AUCUCAGAGUAUUGGCCCCCGUGUAGGUUAUUCUUGACAGACAGUGGAGCUUAU

UCACUCCCAGGAUCCGAGUCGCAUACUACGGUACUGGUGACAGACCUAGGUCGUC

AGUUGACCAGUCCGCCACUAGACGUGAGUCCGUCAAAGCAGUUAGAUGUUACACU

CUAUUAGAUCUCGGAUUACAGCUGGAAGGAGCAGGAGUAGUGUUCUUGCUCUAA

GUACCGAGUGUGCCCAAUACCCGAUCAGCUUAUUAACGAACGGCUCCUCCUCUUA

GACUGCAGCGUAAGUGCGGAAUCUGGGGAUCAAAUUACUGACUGCCUGGAUUAC

CCUCGGACAUAUAACCUUGUAGCACGCUGUUGCUGUAUAGGUGACCAACGCCCAC

UCGAGUAGACCAGCUCUCUUAGUCCGGACAAUGAUAGGAGGCGCGGUCAAUCUAC

UUCUGGCUAGUUAAGAAUAGGCUGCACCGACCUCUAUAAGUAGCGUGUCCUCUA

GAGCUACGCAGGUUCGCAAUAAAAGCGUUGAUUAGUGUGCAUAGAACAGACCUCU

UAUUCGGUGAAACGCCAGAAUGCUAAAUUCCAAUAACUCUUCCCAAAACGCUAC

GGCCGAAGACGCGCGCUUAUCUUGUGUACGUUCUCGCACAUGGAAGAAUCAGCG

GGCAUGGUGGUAGGGCAAUAGGGGAGCUGGGUAGCAGCGAAAAAGGGCCCCUGC

GCACGUAGCUUCGCUGUUCGUCUGAAACAACCCGGCAUCCGUUGUAGCGAUCCCG

UUAUCAGUGUUAUUCUUGUGCGCACUAAGAUUCAUGGUGUAGUCGACAAUAACA

GCGUCUUGGCAGAUUCUGGUCACGUGCCCUAUGCCCGGGCUUGUGCCUCUCAGG

UGCACAGCGAUACUUAAAGCCUUCAAGGUACUCGACGUGGGUACCGAUUCGUGAC

ACUUCCUAAGAUUAUUCCACUGUGUUAGCCCCGCACCGCCGACCUAAACUGGUCC

AAUGUAUACGCAUUCGCUGAGCGGAUCGAUAAUAAAAGCUUGAAUU (SEQ ID NO: 364)
GGGAGAAAGCUCAAGCUUAUCCAAGUAGGCUGGUCACCUGUACAACGUAGCCGGU

AUUUUUUUUUUUUUUUUUUUUUGACCGUCUCAAGGUCCAAGUUAGUCUGCCU

AUAAAGGUGCGGAUCCACAGCUGAUGAAAGACUUGUGCGGUACGGUUAAUCUCC

CCUUUUUUUUUUUUUUUUUUUUAGUAAAUGCGUCUACUGAAUCCAGCGAUGA

UGCUGGCCCAGAUC (R 722 SEQ ID NO: 365)
GGGAGAAAGCUCAAGCUUAUCCAAGUAGGCUGGUCACCUGUACAACGUAGCCGGU

AUUUUUUUUUUUUUUUUUUUUUGACCGUCUCAAGGUCCAAGUUAGUCUGCCU

AUAAAGGUGCGGAUCCACAGCUGAUGAAAGACUUGUGCGGUACGGUUAAUCUCC

CCUUUUUUUUUUUUUUUUUUUUAGUAAAUGCGUCUACUGAAUCCAGCGAUGA

UGCUGGCCCAGAUCUUCGACCACAAGUGCAUAUAGUAGUCAUCGAGGGUCGCCU

UUUUUUUUUUUUUUUUUUUUUGGCCCAGUUCUGAGACUUCGCUAGAGACUAC

AGUUACAGCUGCAGUAGUAACCACUGCGGCUAUUGCAGGAAAUCCCGUUCAGGU

UUUUUUUUUUUUUUUUUUUUCCGCUCACUAUGAUUAAGAACCAGGUGGAGUGU

-continued

```
CACUGCUCUCGAGGUCUCACGAGAGCGCUCGAUACAGUCCUUGGAAGAAUCUUU

UUUUUUUUUUUUUUUUUUUGUGCGACGAUCACAGAGAACUUCUAUUCAUGCAG

GUCUGCUCUA
```

(SEQ ID NO: 366)
```
GGGAGAAAGCUCAAGCUUAUCCAAGUAGGCUGGUCACCUGUACAACGUAGCCGGU

AUUUUUUUUUUUUUUUUUUUUUGACCGUCUCAAGGUCCAAGUUAGUCUGCCU

AUAAAGGUGCGGAUCCACAGCUGAUGAAAGACUUGUGCGGUACGGUUAAUCUCC

CCUUUUUUUUUUUUUUUUUUUUAGUAAAUGCGUCUACUGAAUCCAGCGAUGA

UGCUGGCCCAGAUCUUCGACCACAAGUGCAUAUAGUAGUCAUCGAGGGUCGCCU

UUUUUUUUUUUUUUUUUUUUGGCCCAGUUCUGAGACUUCGCUAGAGACUAC

AGUUACAGCUGCAGUAGUAACCACUGCGGCUAUUGCAGGAAAUCCCGUUCAGGU

UUUUUUUUUUUUUUUUUUCCGCUCACUAUGAUUAAGAACCAGGUGGAGUGU

CACUGCUCUCGAGGUCUCACGAGAGCGCUCGAUACAGUCCUUGGAAGAAUCUUU

UUUUUUUUUUUUUUUUUUGUGCGACGAUCACAGAGAACUUCUAUUCAUGCAG

GUCUGCUCUAGAACGAACUGACCUGACGCCUGAACUUAUGAGCGUGCGUAUUUU

UUUUUUUUUUUUUUUUUUCCUCCCAACAAAUGUCGAUCAAUAGCUGGGCUGU

UGGAGACGCGUCAGCAAAUGCCGUGGCUCCAUAGGACGUGUAGACUUCUAUUUU

UUUUUUUUUUUUUUUUCCCGGGACCACAAAUAAUAUUCUUGCUUGGUUGGGC

GCAAGGGCCCCGUAUCAGGUCAUAAACGGGUACAUGUUGCACAGGCUCCUUUUU

UUUUUUUUUUUUUUUUUCGCUGAGUUAUUCCGGUCUCAAAAGACGGCAGACG

UCAGUCGACAACACGGUCUAAAGCAGUGCUACAAUCUGCCGUGUUCGUGUUUUU

UUUUUUUUUUUUUUGUGAACCUACACGGCGUGCACUGUAGUUCGCAAUUCAU

AGGGUACCGGCUCAGAGUUAUGCCUUGGUUGAAAACUGCCCAGCAUACUUUUUU

UUUUUUUUUUUUUUCAUAUUCCCAUGCUAAGCAAGGGAUGCCGCGAGUCAUGU

UAAGCUUGAAUU
```

According to another very particularly preferred embodiment, the nucleic acid molecule according to formula (VI) may be selected from e.g. any of the following sequences:

(SEQ ID NO: 367)
```
UAGCGAAGCUCUUGGACCUACCUUUUUUUU

UUUUUUCCCUGCGUUCCUAGAAGUACACG
```
or (SEQ ID NO: 368)
```
UAGCGAAGCUCUUGGACCUACCUUUUUUUU

UUUUUUCCCUGCGUUCCUAGAAGUACACG

AUCGCUUCGAGAACCUGGAUGGAAAAAAAA

AAAAAAAGGGACGCAAGGAUCUUCAUGUGC
```

In a further preferred embodiment the nucleic acid molecule of the herein defined inventive polymeric carrier cargo complex may also occur in the form of a modified nucleic acid.

According to a further aspect, the nucleic acid molecule of the herein defined inventive polymeric carrier cargo complex may be provided as a "stabilized nucleic acid", preferably as a stabilized RNA or DNA, more preferably as a RNA that is essentially resistant to in vivo degradation (e.g. by an exo- or endo-nuclease).

In this context, the nucleic acid molecule of the herein defined inventive polymeric carrier cargo complex may contain backbone modifications, sugar modifications or base modifications. A backbone modification in connection with the present invention is a modification in which phosphates of the backbone of the nucleotides contained in the nucleic acid molecule of the inventive polymeric carrier cargo complex are chemically modified. A sugar modification in connection with the present invention is a chemical modification of the sugar of the nucleotides of the nucleic acid molecule of the inventive polymeric carrier cargo complex. Furthermore, a base modification in connection with the present invention is a chemical modification of the base moiety of the nucleotides of the nucleic acid molecule of the inventive polymeric carrier cargo complex.

According to a further aspect, the nucleic acid molecule of the herein defined inventive polymeric carrier cargo complex can contain a lipid modification.

The nucleic acid of the inventive polymeric carrier cargo complex as defined herein may also be in the form of a modified nucleic acid, wherein any modification, as defined herein, may be introduced into the nucleic acid. Modifications as defined herein preferably lead to a further stabilized nucleic acid.

According to one aspect, the nucleic acid of the inventive polymeric carrier cargo complex as defined herein may thus be provided as a "stabilized nucleic acid", preferably as a stabilized mRNA, more preferably as an mRNA that is essentially resistant to in vivo degradation (e.g. by an exo- or endo-nuclease). Such stabilization can be effected, for example, by a modified phosphate in which phosphates of the backbone of the nucleotides contained in the nucleic acid are chemically modified. The nucleic acid of the inventive polymeric carrier cargo complex may additionally or alternatively also contain sugar or base modifications. The nucleic acid of the inventive polymeric carrier cargo complex, particularly if provided as an mRNA, can also be stabilized against degradation by RNases by the addition of a so-called "5' cap" structure. Particular preference is given in this connection to an m7G(5')ppp (5'(A,G(5')ppp(5')A or G(5')ppp(5')G as the 5' cap" structure. According to a further aspect, the nucleic acid of the inventive polymeric carrier cargo complex may contain, especially if the nucleic acid is in the form of an mRNA, a poly-A tail on the 3' terminus of typically about 10 to 200 adenosine nucleotides, preferably about 10 to 100 adenosine nucleotides, more preferably about 20 to 100 adenosine nucleotides or even more preferably about 40 to 80 adenosine nucleotides. According to a further aspect, the nucleic acid of the inventive polymeric carrier cargo complex may contain, especially if the nucleic acid is in the form of an mRNA, a poly-C tail on the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides. According to another aspect, the nucleic acid of the inventive polymeric carrier cargo complex may be modified, and thus stabilized, especially if the nucleic acid is in the form of an mRNA, by modifying the G/C content of the nucleic acid, particularly an mRNA, preferably of the coding region thereof.

In a particularly preferred aspect of the present invention, the G/C content of the coding region of the nucleic acid of the inventive polymeric carrier cargo complex, especially if the nucleic acid is in the form of an mRNA, is modified, particularly increased, compared to the G/C content of the coding region of its particular wild-type mRNA, i.e. the unmodified mRNA. The encoded amino acid sequence of the at least one mRNA is preferably not modified compared to the coded amino acid sequence of the particular wild-type mRNA. Preferably, the G/C content of the coding region of nucleic acid of the inventive polymeric carrier cargo complex, especially if the nucleic acid is in the form of an mRNA, is increased by at least 7%, more preferably by at least 15%, particularly preferably by at least 20%, compared to the G/C content of the coded region of the wild-type mRNA which codes for an antigen, antigenic protein or antigenic peptide as determined herein or its fragment or variant thereof. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence are substituted, thereby increasing the GC/content of said sequence. In this context, it is particularly preferable to increase the G/C content of the nucleic acid of the inventive polymeric carrier cargo complex, especially if the nucleic acid is in the form of an mRNA, to the maximum (i.e. 100% of the substitutable codons), in particular in the region coding for a protein, compared to the wild-type sequence. According to the invention, a further preferred modification of the nucleic acid of the inventive polymeric carrier cargo complex, especially if the nucleic acid is in the form of an mRNA, the region which codes for the adjuvant protein is modified compared to the corresponding region of the wild-type mRNA such that at least one codon of the wild-type sequence which codes for a tRNA which is relatively rare in the cell is exchanged for a codon which codes for a tRNA which is relatively frequent in the cell and carries the same amino acid as the relatively rare tRNA. By this modification, the sequences of the nucleic acid, especially if the nucleic acid is in the form of an mRNA, is modified such that codons for which frequently occurring tRNAs are available are inserted. In other words, according to the invention, by this modification all codons of the wild-type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

Nucleic acid molecules used according to the present invention as defined herein may be prepared using any method known in the art, including synthetic methods such as e.g. solid phase synthesis, as well as in vitro methods, such as in vitro transcription reactions or in vivo reactions, such as in vivo propagation of DNA plasmids in bacteria.

According to another particularly preferred embodiment, the nucleic acid of the inventive polymeric carrier cargo complex, especially if the nucleic acid is in the form of a coding nucleic acid, preferably an mRNA, may additionally or alternatively encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the protein or peptide as encoded by the nucleic acid of the present invention, especially if the nucleic acid is in the form of an mRNA, into a defined cellular compartment, preferably the cell surface, the endoplasmic reticulum (ER) or the endosomal-lysosomal compartment.

Any of the above modifications may be applied to the nucleic acid of the inventive polymeric carrier cargo complex, especially if the nucleic acid is in the form of an mRNA, and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

Proteins or peptides as encoded by the nucleic acid of the inventive polymeric carrier cargo complex as defined herein, may comprise fragments or variants of those sequences. Additionally, the nucleic acid of the inventive polymeric carrier cargo complex may comprise fragments or variants of those coding sequences. Such fragments or variants may typically comprise a sequence having a sequence identity with one of the above mentioned proteins or peptides or sequences of their encoding nucleic acid sequences of at least 5%, 10%, 20%, 30%, 40%, 50%, 60%, preferably at least 70%, more preferably at least 80%, equally more preferably at least 85%, even more preferably at least 90% and most preferably at least 95% or even 97%, to the entire wild-type sequence, either on nucleic acid level or on amino acid level.

"Fragments" of proteins or peptides in the context of the present invention may comprise a sequence of an protein or peptide as defined herein, which is, with regard to its amino acid sequence (or its encoded nucleic acid sequence), N-terminally, C-terminally and/or intrasequentially truncated compared to the amino acid sequence of the original (native) protein (or its encoded nucleic acid sequence). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid sequence of such a protein or peptide. The same applies accordingly to nucleic acids.

Such fragments of proteins or peptides in the context of the present invention may furthermore comprise a sequence of a protein or peptide as defined herein, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form.

The fragments of proteins or peptides as defined herein may also comprise epitopes of those proteins or peptides. Epitopes (also called "antigen determinants") in the context of the present invention are typically fragments located on the outer surface of (native) proteins or peptides as defined herein, preferably having 5 to 15 amino acids, more preferably having 5 to 12 amino acids, even more preferably having 6 to 9 amino acids, which may be recognized by antibodies or B-cell receptors, i.e. in their native form. Such epitopes of proteins or peptides may furthermore be selected from any of the herein mentioned variants of such proteins or peptides. In this context antigenic determinants can be conformational or discontinous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

"Variants" of proteins or peptides as defined herein may be encoded by the nucleic acid of the inventive polymeric carrier cargo complex, wherein nucleotides of the nucleic acid, encoding the protein or peptide as defined herein, are exchanged. Thereby, a protein or peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native potein, e.g. its specific antigenic property.

The present invention also provides a method of preparing the inventive polymeric carrier molecule according to formula (I) L-$P^1$—S—[S—$P^2$—S]$_n$—S—$P^3$-L as defined herein or according to any subformula thereof as defined herein (e.g. (Ia), etc.). It also provides the product obtained or obtainable by such an inventive method (product by process). The method preferably comprises following steps:

a) providing at least one cationic or polycationic protein or peptide as component $P^2$ as defined herein and/or at least one cationic or polycationic polymer as component $P^2$ as defined herein, and optionally at least one further component (e.g. $(AA)_x$, $[(AA_x)]_z$, etc.)., preferably in the ratios indicated above by formula (I), mixing these components, preferably in a basic milieu as defined herein, preferably in the presence of oxygen or a further starter as defined herein which leads to mild oxidation conditions, preferably at a pH, at a temperature and at time as defined herein, and thereby condensing and thus polymerizing these components with each other via disulfide bonds (in a polymerization condensation or polycondensation) to obtain a repetitive component H—[S—$P^2$—S]$_n$—H or H{[S—$P^2$—S]$_a$[S-$(AA)_x$-S]$_b$}H, etc.;

b) providing a hydrophilic polymer $P^1$ and/or $P^3$ as defined herein, optionally modified with a ligand L and/or an amino acid component $(AA)_x$ as defined herein;

c) mixing the hydrophilic polymer $P^1$ and/or $P^3$ provided according to step b) with the repetitive component H—[S—$P^2$—S]$_n$—H or H{[S—$P^2$—S]$_a$[S-$(AA)_x$-S]$_b$}H, etc. obtained according to step a), typically in a ratio of about 2:1, (and thereby typically terminating the polymerization condensation or polycondensation reaction) and obtaining the inventive polymeric carrier, preferably according to formula (I) as defined herein or according to any subformula thereof as defined herein;

d) optionally purifying the inventive polymeric carrier obtained according to step c), preferably using a method as defined herein;

e) optionally adding a nucleic acid as defined herein to the inventive polymeric carrier obtained according to step c) or d), preferably in the above mentioned ratios, and complexing the nucleic acid with the polymeric carrier obtained according to step c) or d) to obtain an inventive polymeric carrier cargo complex as defined herein.

The inventive method of preparing the inventive polymeric carrier according to formula (I) as defined herein represents a multi-step condensation polymerization or polycondensation reaction via —SH moieties of the educts, e.g. component(s) $P^2$ as defined herein, further components $P^1$ and/or $P^3$ and optionally further components $(AA)_x$. The condensation polymerization or polycondensation reaction preferably leads to the inventive polymeric carrier as a condensation polymer, wherein the single components are linked by disulfide bonds. This condensation polymerization leads to the inventive polymeric carrier according to formula (I) preparing in a first step a) of the condensation reaction the inventive repetitive component H—[S—$P^2$—S]$_n$—H or a variant thereof as a sort of a "core" or "central motif" of the inventive polymeric carrier. In a second step b) components $P^1$ and/or $P^3$ are provided, which allow to terminate or to somehow "coat" the inventive repetitive component H—[S—$P^2$—S]$_n$—H or a variant thereof in a third step c) by adding components $P^1$ and/or $P^3$ as defined herein (optionally modified with a ligand L and/or an amino acid component $(AA)_x$ as defined herein) to the condensation product obtained according to step a). In subsequent step d), this product may be purified and further used to complex a nucleic acid cargo as defined herein to obtain an inventive complex.

It is important to understand that the inventive method is based on an equibrility reaction under mild oxidation conditions in steps a), (b)) and c), which, upon balancing the equilibrity state, allows to obtain the inventive polymeric carrier according to formula (I) above or according to any of its subformulas comprising the selected components in the desired molar ratios. For this purpose, long reaction times are envisaged to achieve an equibrility state in steps a), (b)) and c). If for example a condensation polymerization is to be carried out using a molar ratio of 5 components $P^2$ in step a), the equilibrium is surprisingly settled at a polymer length of about 5 after sufficient time, preferably e.g. >12 hours. However, due to the equilibrium the polymer length (as defined by n) is not fixed at a specific value, e.g. 5, but may vary accordingly within the equibrility reaction. Accordingly, about 5 may mean about 4 to 6, or even about 3 to 7. Preferably, the polymer length and thus the integer n (and thus a, b and a+b) varies within a limit of about ±1, or ±2.

As defined herein in a step a) of the inventive method of preparing the inventive polymeric carrier according to formula (I) at least one cationic or polycationic protein or peptide as component $P^2$ as defined herein and/or at least one cationic or polycationic polymer as component $P^2$ as defined herein are provided, preferably in the ratios indicated above by formula (I). These components are mixed, preferably in a basic milieu as defined herein, preferably in the presence of oxygen or a further starter as defined herein which leads to mild oxidation conditions, preferably at a pH, and at a temperature and at a time as defined herein, and thereby condensing and thus polymerizing these components with each other via disulfide bonds (in a polymerization condensation or polycondensation) to obtain a repetitive component H—$[S-P^2-S]_n$—H.

According to an alternative, in step a) of the inventive method of preparing the inventive polymeric carrier at least one cationic or polycationic protein or peptide and/or at least one cationic or polycationic polymer are provided and used as component(s) $P^2$ as defined herein, and additionally at least one amino acid component $(AA)_x$ is provided as defined herein, and components $P^2$ and $(AA)_x$ are used for a polymerization condensation or polycondensation according to step a). Preferably, the components are all provided in the ratios indicated above by formula (Ia), mixed, preferably in a basic milieu as defined herein, preferably in the presence of oxygen or a further starter as defined herein which leads to mild oxidation conditions, preferably at a pH, at a temperature and at time as defined herein. Upon mixing and starting the reaction, the components are condensed and thus polymerized with each other via disulfide bonds (in a polymerization condensation or polycondensation) to obtain a repetitive component H—$\{[S-P^2-S]_a[S-(AA)_x-S]_b\}$—H.

In both of the above alternatives, different component(s) $P^2$, particularly different peptides and/or different polymers as component $P^2$, may be selected in the condensation polymerization as indicated above. In this context, the selection of different component(s) $P^2$ is typically dependent upon the desired properties of the final inventive polymeric carrier and the desired cationic strength of the final inventive polymeric carrier or its central core motif. Accordingly, the repetitive component $[S-P^2-S]_n$, may furthermore be "diluted" or modified in the above alternative of step a) e.g. by introducing an amino acid component $(AA)_x$ as defined herein, preferably in the above defined ratios. Thereby, a modified central core motif $\{[S-P^2-S]_a[S-(AA)_x-S]_b\}$ may be obtained, wherein the cationic character of (unmodified) repetitive component $[S-P^2-S]_n$ typically remains in the limitations as defined herein. The properties of the final inventive polymeric carrier may thus be adjusted as desired with properties of components $(AA)_x$ by inserting amino acid component $(AA)_x$ as defined herein in steps a), b) and/or c).

In all cases, step a) is based on an equibrility reaction under mild oxidation conditions which, upon balancing the equilibrity state, allows to obtain either inventive repetitive component H—$[S-P^2-S]_n$—H or inventive repetitive component H—$\{[S-P^2-S]_a[S-(AA)_x-S]_b\}$—H in the desired molar ratios. In the equilibrity state, n is preferably 1, 2, 3, 4, or 5 to 10, more preferably 4 to 9, and a+b=n is as defined above, preferably a+b=1, 2, 3, 4, or 5 to 10, more preferably 4 to 9. For this purpose, long reaction times are envisaged to achieve an equibrility state in step a), most preferably e.g. >12 hours. Accordingly, step a) of the inventive method of preparing a polymeric carrier typically requires at least about 5 hours, even more preferably at least about 7.5 hours or even 10 hours, most preferably at least about 12 hours, e.g. a reaction time of about 12 to 60 hours, a reaction time of about 12 to 48 hours, a reaction time of about 12 to 36 hours, or a reaction time of about 12 to 24 hours, etc, wherein the lower border of 12 hours of thelatter ranges may also be adjusted to 10, 7.5, or even 5 hours. Advantageously, the equilibrity state can be balanced using the inventive method.

In step a), the at least one cationic or polycationic protein or peptide as component $P^2$ as defined herein and/or at least one cationic or polycationic polymer as component $P^2$ as defined herein, and optionally at least one amino acid component $(AA)_x$ as defined herein, are preferably contained in a basic milieu in the step a) of the inventive method of preparing the inventive polymeric carrier according to formula (I) (or any of its subformulas, e.g. (Ia)). Such a basic milieu typically exhibits a pH range of about 6 to about 12, preferably a pH range of about 7 to about 10, more preferably a pH range of about 8 to about 10, e.g. about 8, 8.5, 9, 9.5, or 10 or any range selected from any two of these or the aforementioned values.

Furthermore, the temperature of the solution in step a) is preferably in a range of about 5° C. to about 60° C., more preferably in a range of about 15° C. to about 40° C., even more preferably in a range of about 20° C. to about 30° C., and most preferably in a range of about 20° C. to about 25° C., e.g. about 25° C.

In step a) of the inventive method of preparing the inventive polymeric carrier according to formula (I) (or any of its subformulas, e.g. (Ia)) as defined herein buffers may be used as suitable. Preferred buffers may comprise, but are not limited to carbonate buffers, borate buffers, Bicine buffer, CHES buffer, CAPS buffer, Ethanolamine containing buffers, HEPES, MOPS buffer, Phosphate buffer, PIPES buffer, Tris buffer, Tricine buffer, TAPS buffer, and/or TES buffer as buffering agents. Particularly preferred is a carbonate buffer.

Upon mixing the components, preferably in the presence of oxygen, preferably in the presence of a basic mileu as defined herein, the condensation polymerization or polycondensation reaction is started. For this purpose, the mixture in step a) is preferably exposed to oxygen or may be started using a further starter, e.g. a catalytical amount of an oxidizing agent, e.g. DMSO, etc. To determine the desired polymer chain length the condensation reaction has to be carried out under mild oxidation conditions, preferably in the presence of less than 30% DMSO, more preferably in the presence of less than 20% DMSO and most preferably in the presence of less than 10% DMSO. Upon start of the condensation polymerization or polycondensation reaction the at least one cationic or polycationic protein or peptide and/or at least one cationic or polycationic polymer as component $P^2$ and optionally at least one amino acid component $(AA)_x$ as defined herein, are condensed and thus polymerized with each other via disulfide bonds (polymerization condensation or polycondensation). In this reaction step a) preferably linear polymers are created using monomers with at least two reactive —SH moieties, i.e. at least one cationic or polycationic protein or peptide and/or at least one cationic or polycationic polymer as component $P^2$ as defined herein, each component $P^2$ exhibiting at least two free —SH-moieties as defined herein, e.g. at their terminal ends. However, components $P^2$ with more than two free —SH-moieties may be used, which may lead to branched polymers.

According to one other specific embodiment, the condensation product obtained according to step a) may be modified (e.g. in a step a1)) by adding an amino acid component $(AA)_x$ or a mixed repetitive amino acid component $[(AA)_x]_z$ as defined herein e.g. to the terminal ends of the condensation product of step a). This may occur via any functionality as defined herein, e.g. a —SH moiety or any further functionality described herein, preferably a —SH moiety. For this purpose, amino acid component $(AA)_x$ or a mixed repetitive amino acid component $[(AA)_x]_z$ may be provided with two (or even more) —SH-moieties, e.g. in a form represented by formulae "H(S-AA-S)$_x$H" or "H[S-(AA)$_x$-S]$_z$H". Then, a polycondensation reaction may be carried out with the products of step a), i.e. inventive repetitive component H—[S—P$^2$—S]$_n$—H or inventive repetitive component H—{[S—P$^2$—S]$_a$[S-(AA)$_x$-S]$_b$}—H, leading to intermediate components

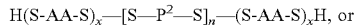

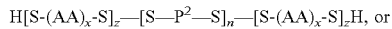

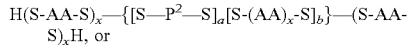

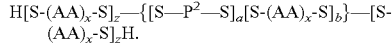

Any single or all of these intermediate components or the inventive repetitive component

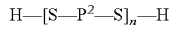

or the inventive repetitive component

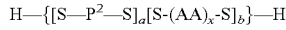

obtained according to step a), may be used to be coupled to the polymers provided in step b) of the inventive method.

According to a second step b) of the inventive method of preparing the inventive polymeric carrier according to formula (I) as defined herein (or according to any of its subformulas), a hydrophilic polymer $P^1$ and/or $P^3$ as defined herein is added to the condensation product obtained according to step a). In this context, the hydrophilic polymers $P^1$ and/or $P^3$ as defined herein, preferably exhibit at least one —SH-moiety, more preferably only one —SH-moiety per hydrophilic polymers $P^1$ and/or $P^3$ as defined herein, thereby terminally stopping the polymerization condensation or polycondensation according to step a) in step c). Hydrophilic polymers $P^1$ and/or $P^3$ as defined herein may be the same or different, wherein these polymers may be selected according to the desired properties. Typically, hydrophilic polymers $P^1$ and/or $P^3$ as a whole may be added to the condensation product obtained according to step a) in a ratio of about 2:1 hydrophilic polymer $P^1$ and/or $P^3$:condensation product obtained according to step a).

According to one alternative, the hydrophilic polymer(s) $P^1$ and/or $P^3$ additionally may be modified with either a component L (ligand) as defined herein or a component $(AA)_x$ or $[(AA)_x]_z$ as defined herein or both a component L (ligand) as defined herein and a component $(AA)_x$ or $[(AA)_x]_z$ as defined herein.

According to a first example, a ligand is attached to component(s) $P^1$ and/or $P^3$ as component L prior to providing component(s) $P^1$ and/or $P^3$ in step b) via any functionality as defined herein, e.g. a —SH moiety. This ligand is preferably attached to the hydrophilic polymer(s) $P^1$ and/or $P^3$ at one terminus of these polymers. If the attachment is carried out via —SH bonds, the hydrophilic polymer(s) $P^1$ and/or $P^3$ are preferably provided with two (or even more) —SH-moieties., e.g. in a form represented by formulae HS—$P^1$—SH or HS—$P^3$—SH. Ligand L preferably carries only one —SH moiety. In this case, one —SH moiety of hydrophilic polymer(s) $P^1$ and/or $P^3$ is preferably protected in a first step using a protecting group as known in the art. Then, the hydrophilic polymer(s) $P^1$ and/or $P^3$ may be bound to a component L to form a first disulfide bond via the non-protected —SH moiety. The protected —SH-moiety of hydrophilic polymer(s) $P^1$ and/or $P^3$ is then typically deprotected for further reactions. This preferably leads to following intermediate components

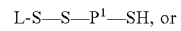

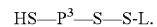

Alternatively, the above intermediate components may be provided similarly without the necessity of blocking the free —SH-moieties. These intermediate components may be used in step c) to be coupled with the condensation products obtained according to step a) above, e.g. to form a second disulfide bond with inventive repetitive component H—[S—P$^2$—S]$_n$—H or inventive mixed repetitive component H—{[S—P$^2$—S]$_a$[S-(AA)$_x$-S]$_b$}—H obtained according to step a) or any of its modifications, e.g. according to step a1). If the attachment is carried out via other moieties, any of the reactions as defined herein may be used accordingly.

According to a further example, an amino acid component $(AA)_x$ or a mixed repetitive amino acid component $[(AA)_x]_z$ as defined herein may be attached to component(s) $P^1$ and/or $P^3$ prior to providing component(s) $P^1$ and/or $P^3$ via any functionality as defined herein, e.g. a —SH moiety. The amino acid component $(AA)_x$ or a mixed repetitive amino acid component $[(AA)_x]_z$, may be attached to the hydrophilic polymer(s) $P^1$ and/or $P^3$ at any position within these polymers or at one or both termini of these polymers. In one specific case, the amino acid component $(AA)_x$ or a mixed repetitive amino acid component $[(AA)_x]_z$ may be provided as a linker between component(s) $P^1$ and/or $P^3$ and the condensation product obtained according to step a) above or as a linker between component(s) $P^1$ and/or $P^3$ and a further component, e.g. a linker L, or according to another alternative, as a terminating component at one terminus of component(s) $P^1$ and/or $P^3$. In any of these cases, the attachment preferably may carried out via —SH bonds, wherein the hydrophilic polymer(s) $P^1$ and/or $P^3$ are preferably provided with two (or even more) —SH-moieties., e.g. in a form represented by formula "HS—$P^1$—SH" or "HS—$P^3$—SH", wherein preferably one of these to —SH moieties is protected, e.g. in a form represented by formula "HS—$P^1$—S- protecting group" or "protecting group-S—P³—SH". Furthermore, amino acid component $(AA)_x$ or a mixed repetitive amino acid component $[(AA)_x]_z$ are also preferably provided with two (or even more) —SH-moieties, e.g. in a form represented by formulae "H(S-AA-S))$_x$—H" or "H[S-$(AA)_x$—S]$_z$H", wherein preferably one of these to —SH moieties is protected, e.g. in a form represented by formulae "protecting group-(S-AA-S)$_x$—SH" or "H[S-$(AA)_x$-S]$_z$-protecting group". Then, a polycondensation reaction may be carried out with polymers "HS—P¹—S-protecting group" or "protecting group-S—P³—SH" leading to intermediate components "protecting group-S—P¹—S—(S-AA-S)—S-protecting group", "protecting group-(S-AA-S)$_x$—S—S—P³—S-protecting group", "protecting group-S—P¹—S—[S-$(AA)_x$-S]$_z$-protecting group", or "protecting group-[S-$(AA)_x$-S]$_z$—S—P³—S-protecting group".

Any single or all of these intermediate components may then be used in step c) of the inventive method to be coupled to the condensation product according to step a).

For this purpose, at least one or both protecting groups (selected upon the desired direction of the component in the final carrier) of each intermediate compound may be deprotected prior to providing them in step b), leading to following intermediate components "HS—P¹—S—(S-AA-S)$_x$—SH", "H(S-AA-S))$_x$—S—S—P³—SH", "HS—P¹—S—[S-$(AA)_x$S]$_z$H", or "H[S-$(AA)_x$-S]$_z$—S—P³—SH", Alternatively, the above intermediate components may be provided similarly without the necessity of blocking the free —SH-moieties. Any single or all of these intermediate components may then be provided in step b) of the inventive method to be coupled to the condensation product according to step a).

If any of the afore mentioned intermediate components is provided in step b), this condensation reaction may be terminated in a step c) by adding a linker component as defined herein with one —SH-moiety (e.g. L-SH) or any further component with a single —SH moiety, e.g. as defined herein. In one further specific case, the amino acid component $(AA)_x$ or a mixed repetitive amino acid component $[(AA)_x]_z$ may be used as a terminal component at one terminus of component(s) P¹ and/or P³ without adding a further component to the amino acid component $(AA)_x$ or a mixed repetitive amino acid component $[(AA)_x]_z$.

According to a further example, an amino acid component $(AA)_x$ or a mixed repetitive amino acid component $[(AA)_x]_z$ as defined herein may be attached to component(s) P¹ and/or P³ prior to step c), wherein component(s) P¹ and/or P³ have been already modified with a linker. For this purpose, component(s) P¹ and/or P³ preferably carry (at least) two —SH moieties as defined herein, wherein a polycondensation is carried out with a linker, carrying e.g. one —SH moiety. This reaction may be carried out by using protecting groups as defined herein, or, preferably, without protecting groups. Alternatively, any further functionality as defined herein except —SH moieties may be used for coupling. Then, the second —SH moiety of component(s) P¹ and/or P³ may be used to couple an amino acid component $(AA)_x$ or a mixed repetitive amino acid component MAW, as defined herein via —SH-moieties, e.g. in a form represented by formulae "H(S-AA-S)$_x$—H" or "H[S-$(AA)_x$-S]$_z$H". The reaction preferably leads to following intermediate compounds "L-S—S—P¹—S—(S-AA-S)$_x$—SH", "L-S—S—P¹—S—[S-$(AA)_x$-S]$_z$H", or "HS—(S-AA-S)$_x$—S—S—P³—S—S-L", or "HS—[S-$(AA)_x$-S]$_z$—S—S—P³—S—S-L";

or, if component L has been linked without a disulfide bond to following intermediate products "L-P¹—S—(S-AA-S)$_x$—SH", "L-P¹—S—[S-$(AA)_x$-S]$_z$H", or "HS—(S-AA-S)$_x$—S—S—P³³-L", or "HS—[S-$(AA)_x$-S]$_z$—S—P³-L";

In step c) the hydrophilic polymers P¹ and/or P³ (or any of the intermediate components provided according to step b)) as defined herein, are provided and mixed with the repetitive component H—[S—P²—S]$_n$—H, with the mixed repetitive component H—{[S—P²—S]$_a$[S-$(AA)_x$-S]$_b$}—H, or any of the intermediate components obtained according to step a), typically in a ratio of about 2:1. The reaction is typically started and carried out under conditions already described above for step a) (pH, temperature, reaction time, buffers, etc.). Step c) allows to terminate the polymerization condensation or polycondensation reaction and to obtain the inventive polymeric carrier according to formula (I) or (Ia) or according to any of subformulas thereof as defined herein, preferably the inventive polymeric carrier according to formula (I)

L-P¹—S—[S—P²—S]$_n$—S—P³-L or according to formula (Ia)

L-P¹—S—{[S—P²—S]$_a$[S-$(AA)_x$-S]$_b$}—S—P³-L.

According to a further step d) of the inventive method of preparing the inventive polymeric carrier according to formula (I) or (Ia) as defined herein, or according to any of subformulas thereof as defined herein, the inventive polymeric carrier obtained according to step c) is optionally purified. Purification may occur by using chromatographic methods, such as HPLC, FPLC, GPS, dialysis, etc.

According to a final step e) of the inventive method of preparing the inventive polymeric carrier according to formula (I) or (Ia) as defined herein, or according to any of subformulas thereof as defined herein, a nucleic acid as defined herein is optionally added to the inventive polymeric carrier obtained according to step c) or d), preferably in the above mentioned ratios. Typically, in the inventive complex, the polymeric carrier molecule according to generic formula (I) or (Ia) or according to any of subformulas thereof as defined herein, as defined herein and the nucleic acid are provided in a molar ratio of about 5 to 10000, preferably in a molar ratio of about 5 to 5000, more preferably in a molar ratio of about 5 to 2500, even more preferably in a molar ratio of about 5 to 1000 polymeric carrier:nucleic acid, e.g. in a molar ratio of about 10 to 10000, in a molar ratio of about 10 to 5000, in a molar ratio of about 25 to 2500, or in a molar ratio of about 50 to 1000 polymeric carrier:nucleic acid. The N/P ratios are preferably as indicated above.

The inventive method of preparing the inventive polymeric carrier according to formula (I) or (Ia) or according to any of subformulas thereof as defined herein is particularly suitable to adapt the chemical properties of the desired inventive polymeric carrier due to specific selection of its components $P^2$, L, $(AA)_x$, or $[(AA)_x]_z$ thereby avoiding agglomeration and toxicity in vivo.

Furthermore, a skilled person would not have expected to obtain an inventive polymeric carrier using the above inventive method as the skilled person would always have expected that the polymer obtained according to the inventive method due to general rules of equilibrity reactions leads to a monomeric content of component $P^2$, flanked by monomeric components $P^1$ and/or $P^3$, wherein the linkages are formed by disulfide bonds. In contrast, the present inventors were surprisingly able to show that when using a specific ratio of polymers and method steps as defined herein, particularly mild oxidation conditions during the polymerization reaction, the polymerization condensation can be directed to specifically obtain a desired distribution of polymers and a desired average length and the desired inventive polymeric carrier according to generic formula (I) or (Ia) or according to any of subformulas thereof as defined herein without the necessity of blocking the free —SH-moieties. This was not expected by a skilled person.

According to a further embodiment, the present invention also provides a pharmaceutical composition, comprising the inventive polymeric carrier cargo complex formed by a nucleic acid cargo as defined herein and a polymeric carrier molecule according to generic formula (I) or (Ia) or according to any of subformulas thereof as defined herein and optionally a pharmaceutically acceptable carrier and/or vehicle.

As a first ingredient, the inventive pharmaceutical composition comprises the polymeric carrier cargo complex formed by the nucleic acid cargo and a polymeric carrier molecule according to generic formula (I) or (Ia) or according to any of subformulas thereof as defined herein.

As a second ingredient the inventive pharmaceutical composition may comprise at least one additional pharmaceutically active component. A pharmaceutically active component in this connection is a compound that has a therapeutic effect to heal, ameliorate or prevent a particular indication, preferably cancer diseases, autoimmune disease, allergies or infectious diseases. Such compounds include, without implying any limitation, peptides or proteins, preferably as defined herein for coding nucleic acids, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g. phosphate, citrate etc. buffered solutions. Particularly for injection of the inventive pharmaceutical composition, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined herein, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

According to another aspect, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition typically elicits an innate immune response due to the adjuvant, optionally contained therein. Such an adjuvant may be selected from any adjuvant known to a skilled person and suitable for the present case, i.e. supporting the induction of an innate immune response in a mammal.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intraarticular, intra-synovial, intrasternal, intrathecal, intrahepatic, intralesional, intracranial, transdermal, intradermal, intrapulrnonal, intraperitoneal, intracardial, intraarterial, and sublingual injection or infusion techniques.

The inventive pharmaceutical composition may be used for human and also for veterinary medical purposes, preferably for human medical purposes, as a pharmaceutical composition in general or as a vaccine.

According to a particular preferred aspect, the inventive pharmaceutical composition (or the inventive polymeric carrier cargo complex) may be provided or used as an immunostimulating agent. In this context, the inventive pharmaceutical composition is preferably as defined above. More preferably, the nucleic acid of the inventive polymeric carrier cargo complex, preferably contained in the pharmaceutical composition, is typically an immunostimulatory nucleic acid as defined herein, e.g. a CpG-DNA or an immunostimulatory RNA (isRNA). Alternatively or additionally, the nucleic acid of the inventive polymeric carrier cargo complex, preferably contained in the pharmaceutical composition, is a coding nucleic acid as defined herein, preferably a cDNA or an mRNA, more preferably encoding an adjuvant protein preferably as defined herein.

In a specific aspect of this embodiment in this context it is preferred that an adjuvant protein is a component of the polymeric carrier, preferably as $(AA)_x$, component.

According to an even more preferred aspect, the inventive pharmaceutical composition (or the inventive polymeric carrier cargo complex) may be provided or used as an adjuvant. In this context, the adjuvant is preferably defined as the inventive pharmaceutical composition above. More preferably, the nucleic acid of the inventive polymeric carrier cargo complex, preferably contained in the adjuvant, is typically an immunostimulatory nucleic acid as defined herein, e.g. a CpG-DNA or an immunostimulatory RNA (isRNA). Alternatively or additionally, the nucleic acid of the inventive polymeric carrier cargo complex, preferably contained in the adjuvant, is a coding nucleic acid as defined herein, preferably a cDNA or an mRNA, more preferably encoding an adjuvant protein, preferably as defined herein. The inventive polymeric carrier cargo complex, preferably contained in the adjuvant, typically initiates an innate immune response in the patient to be treated. Such an adjuvant may be utilized in any accompanying therapy, with any known vaccine or any further (known) therapeutic agent, preferably prior to, concurrent with or subsequent to administration of the main therapy, prior to, concurrent with or subsequent to administration of a further (known) vaccine or a (known) further therapeutic agent.

The inventive polymeric carrier cargo complex or the inventive pharmaceutical composition as defined herein provided or used as an adjuvant is preferably capable of triggering a non-antigen-specific, (innate) immune reaction (as provided by the innate immune system), preferably in an immunostimulating manner. An immune reaction can generally be brought about in various ways. An important factor for a suitable immune response is the stimulation of different T-cell sub-populations. T-lymphocytes typically differentiate into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the immune-stimulating agent, namely the inventive polymeric carrier cargo complex in the direction towards the cellular response, that is to say the Th1 response, and a predominantly cellular immune response is thereby induced. As defined above, the inventive polymeric carrier cargo complex exerts by itself an unspecific innate immune response, which allows the inventive polymeric carrier cargo complex be used as such (without adding another pharmaceutically active component) as an immunostimulating agent. If administered together with another pharmaceutically active component, preferably a specifically immunogenic component, preferably an antigen, the nucleic acid of the invention serves as an adjuvant supporting the specific adaptive immune response elicited by the other pharmaceutically active component e.g. an antigen.

According to another particularly preferred embodiment, the inventive pharmaceutical composition (or the inventive polymeric carrier cargo complex) may be provided or used as a vaccine.

Such an inventive vaccine is typically composed like the inventive pharmaceutical composition and preferably supports or elicits an immune response of the immune system of a patient to be treated, e.g. an innate immune response, if an RNA or mRNA is used as the nucleic acid molecule of the inventive polymeric carrier cargo complex formed by the nucleic acid cargo and a polymeric carrier molecule according to generic formula (I) or (Ia) or according to any of subformulas thereof as defined herein. Furthermore or alternatively, the inventive vaccine may elicit an adaptive immune response, preferably, if the nucleic acid of the inventive polymeric carrier cargo complex formed by the nucleic acid cargo and a polymeric carrier molecule according to generic formula (I) or (Ia) or according to any of subformulas thereof as defined herein encodes any of the above mentioned antigens or proteins, which elicit an adaptive immune response.

In this context, the vaccine is preferably defined as an adjuvant or as an inventive pharmaceutical composition as disclosed above. More preferably, the nucleic acid of the inventive polymeric carrier cargo complex, contained in such a vaccine, may be any nucleic acid as defined above, preferably an immunostimulatory nucleic acid as defined herein, e.g. a CpG-DNA or an immunostimulatory RNA (isRNA). Alternatively or additionally, the nucleic acid of the inventive polymeric carrier cargo complex, preferably contained in the vaccine, is a coding nucleic acid as defined herein, preferably a cDNA or an mRNA, more preferably encoding an adjuvant protein, preferably as defined herein. Alternatively or additionally, the nucleic acid of the inventive polymeric carrier cargo complex, preferably contained in the vaccine, is a coding nucleic acid as defined herein, preferably a cDNA or an mRNA, more preferably encoding an antigen, preferably as defined herein. Furthermore, particularly, if the nucleic acid of the inventive polymeric carrier cargo complex does not encode an antigen, the inventive vaccine may contain an antigen, preferably as defined above, either as a protein or peptide or encoded by a nucleic acid, or antigenic cells, antigenic cellular fragments, cellular fractions; cell wall components (e.g. polysaccharides), modified, attenuated or de-activated (e.g. chemically or by irradiation) pathogens (virus, bacteria etc.).

According to a further aspect the inventive vaccine may contain a peptide or protein antigen as $(AA)_x$ component of the inventive polymeric carrier as defined herein, preferably as part of the repetitive component $[S—P^2—S]_n$.

The inventive vaccine may also comprise a pharmaceutically acceptable carrier, adjuvant, and/or vehicle as defined herein for the inventive pharmaceutical composition.

The inventive vaccine can additionally contain one or more auxiliary substances in order to increase its immunogenicity, if desired. A synergistic action of the inventive polymeric carrier cargo complex formed by the nucleic acid cargo and a polymeric carrier molecule according to generic formula (I) or (Ia) or according to any of subformulas thereof as defined herein and of an auxiliary substance, which may be optionally contained in the inventive vaccine as defined herein, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally or alternatively contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

The inventive vaccine can also additionally or alternatively contain an immunostimulatory RNA, i.e. an RNA derived from an immunostimulatory RNA, which triggers or increases an (innate) immune response. Preferably, such an RNA may be in general as defined herein for RNAs. In this context, those classes of RNA molecules, which can induce an innate immune response, may be selected e.g. from ligands of Toll-like receptors (TLRs), particularly from RNA sequences representing and/or encoding ligands of TLRs, preferably selected from human family members TLR1-TLR10 or murine family members TLR1-TLR13, more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

The present invention furthermore provides several applications and uses of the inventive polymeric carrier molecule according to generic formula (I) or (Ia) or according to any of subformulas thereof as defined herein, the inventive polymeric carrier cargo complex formed by the nucleic acid cargo and the inventive polymeric carrier molecule, a pharmaceutical composition comprising same or of kits comprising same.

According to one embodiment, the present invention is directed to the first medical use of the inventive polymeric carrier molecule according to generic formula (I) or (Ia) or according to any of subformulas thereof as defined herein, of the inventive polymeric carrier cargo complex formed by the nucleic acid cargo and the inventive polymeric carrier molecule, or of kits comprising same, as a medicament, preferably for gene therapy or treatment of a disease as defined herein. The medicament may be in the form of a pharmaceutical composition or in the form of an adjuvant or a vaccine as a specific form of pharmaceutical compositions. A pharmaceutical composition in the context of the present invention typically comprises the inventive polymeric carrier molecule according to generic formula (I) or (Ia) or according to any of subformulas thereof as defined herein or the inventive polymeric carrier cargo complex formed by the nucleic acid cargo and the inventive polymeric carrier molecule, optionally further ingredients, e.g. as defined herein for the inventive nucleic acid, and optionally a pharmaceutically acceptable carrier and/or vehicle, preferably as defined herein.

According to one further embodiment, the present invention is directed to the use of the inventive polymeric carrier molecule according to generic formula (I) or (Ia) or according to any of subformulas thereof as defined herein, preferably with a nuleic acid cargo as defined herein, or of the inventive polymeric carrier cargo complex formed by the nucleic acid cargo and the inventive polymeric carrier molecule for the prophylaxis, treatment and/or amelioration of diseases as defined herein. Preferably, diseases as mentioned herein are selected from cancer or tumour diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a defined gene defect and are inherited according to Mendel's laws, cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and any disease which can be influenced by the present invention.

According to another embodiment, the present invention is directed to the second medical use of the inventive polymeric carrier molecule according to generic formula (I) or (Ia) or according to any of subformulas thereof as defined herein, or of the inventive polymeric carrier cargo complex formed by the nucleic acid cargo and the inventive polymeric carrier molecule for the treatment of diseases as defined herein, preferably to the use of the inventive polymeric carrier molecule according to generic formula (I) or (Ia) or according to any of subformulas thereof as defined herein, or of the inventive polymeric carrier cargo complex formed by the nucleic acid cargo and the inventive polymeric carrier molecule, of a pharmaceutical composition comprising same or of kits comprising same for the preparation of a medicament for the prophylaxis, treatment and/or amelioration of various diseases as defined herein.

According to one further embodiment, the present invention is directed to the use of the inventive polymeric carrier molecule according to generic formula (I) or (Ia) or according to any of subformulas thereof as defined herein, preferably with a nucleic acid cargo as defined herein, or of the inventive polymeric carrier cargo complex formed by the nucleic acid cargo and the inventive polymeric carrier molecule for immunotherapy, for gene therapy, for vaccination, or to the use thereof as an adjuvant.

According to a further embodiment, the present invention is directed to the treatment of diseases as defined herein, particularly prophylaxis, treatment and/or amelioration of various diseases as defined herein, preferably using or administering to a patient in need thereof the inventive polymeric carrier cargo complex formed by the nucleic acid cargo and the inventive polymeric carrier molecule according to generic formula (I) or (Ia) or according to any of subformulas thereof as defined herein, or the inventive pharmaceutical composition or vaccine as defined herein.

The present invention also allows treatment of diseases, which have not been inherited, or which may not be summarized under the above categories. Such diseases may include e.g. the treatment of patients, which are in need of a specific protein factor, e.g. a specific therapeutically active protein as mentioned above. This may e.g. include dialysis patients, e.g. patients which undergo a (regular) a kidney or renal dialysis, and which may be in need of specific therapeutically active proteins as defined herein, e.g. erythropoietin (EPO), etc.

According to a final embodiment, the present invention also provides kits, particularly kits of parts, comprising as components alone or in combination with further ingredients at least one inventive polymeric carrier molecule according to generic formula (I) or (Ia) or according to any of subformulas thereof as defined herein, at least one inventive polymeric carrier cargo complex formed by the nucleic acid cargo and the inventive polymeric carrier molecule, at least one nucleic acid as defined herein, at least one pharmaceutical composition comprising same and/or kits comprising same, and optionally technical instructions with information on the administration and dosage of the inventive polymeric carrier molecule, the nucleic acid, the inventive polymeric carrier complex, and/or the inventive pharmaceutical composition. Such kits, preferably kits of parts, may be applied, e.g., for any of the above mentioned applications or uses. Such kits, when occurring as a kit of parts, may further contain each component in a different part of the kit.

FIGURES

The following Figures are intended to illustrate the invention further. They are not intended to limit the subject matter of the invention thereto.

FIG. 1: illustrates the products formed during the reaction by SDS PAGE gel electrophoresis under non-reducing conditions. The left part of the gel was stained according to coomassie protocol which colors the peptide content, the right part was stained with Bariumchloride/Iodine solutions which colour the PEG content. As may be easily seen only one product containing PEG and peptide is formed in the range of the intended mass.

Figure 2:
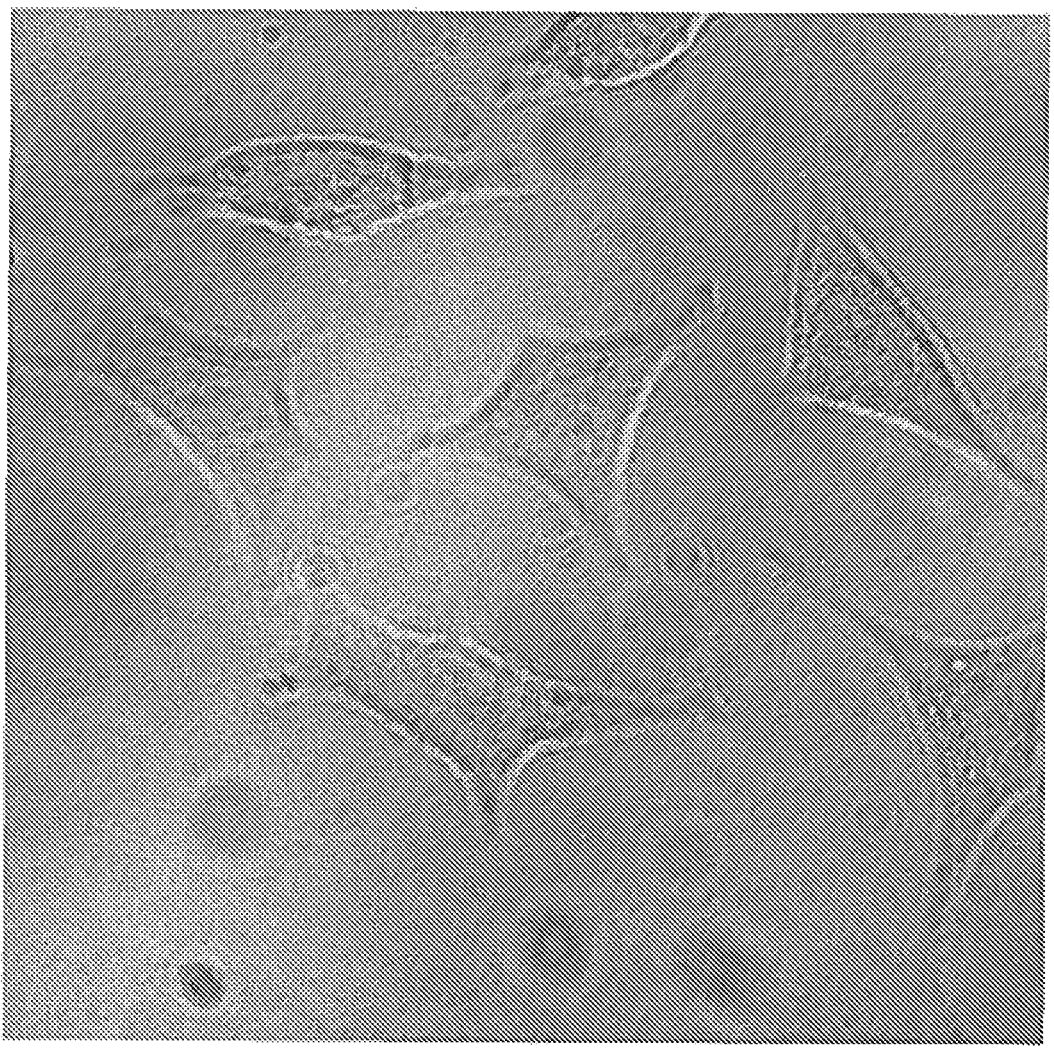

FIG. 2: shows the results of the confocal microscopy of L929 cells 5 minutes after transfection with fluorescence labelled RNA complexed with the inventive polymeric carrier PB19 in a molar ratio of 1:500. As a result, several complexes are detectable in the cells already 5 minutes after transfection indicating a good transfection rate.

Figure 3:
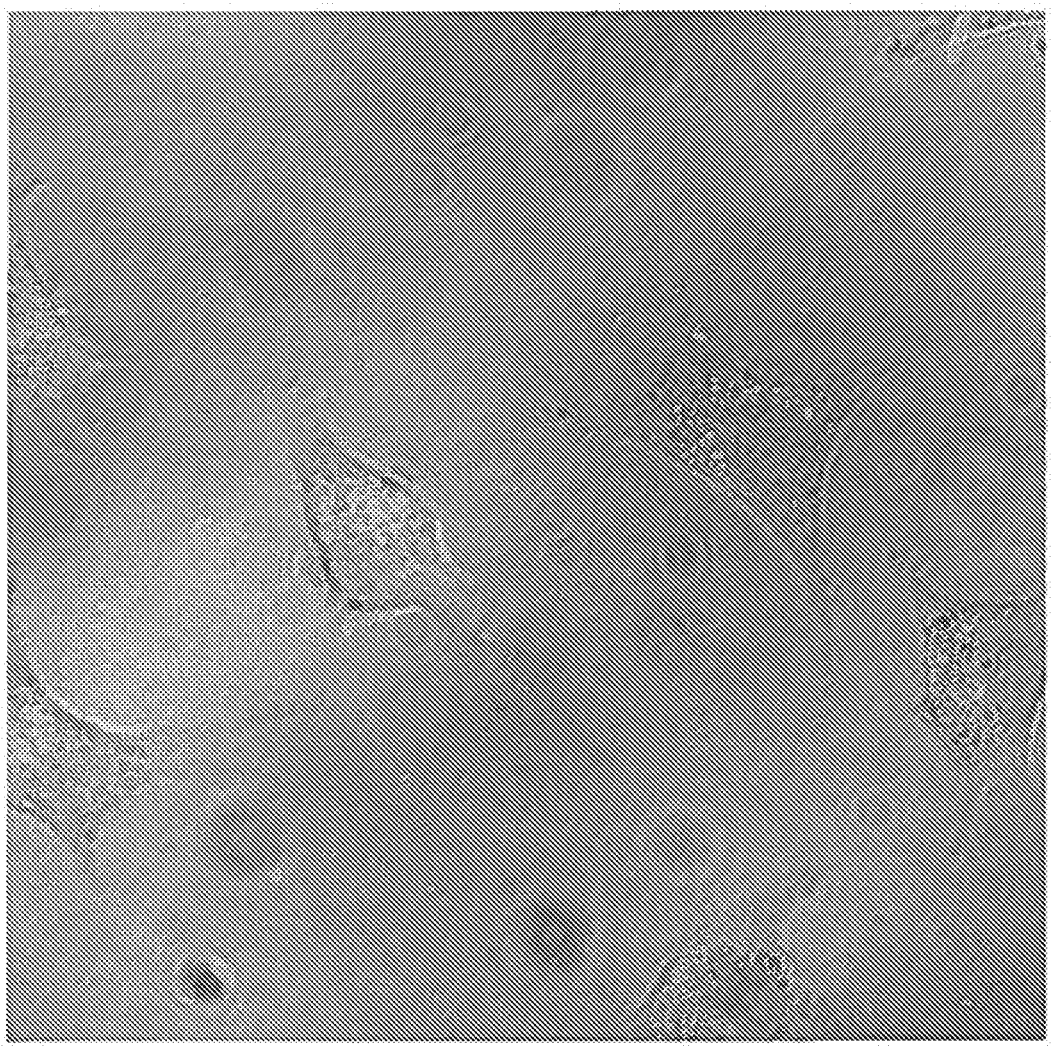

FIG. 3: shows the results of the confocal microscopy of L929 cells 1 hour after transfection with fluorescence labelled RNA complexed with the inventive polymeric carrier PB19 in a molar ratio of 1:500. As a result, most of the particles were taken up in the cells 1 hour after transfection showing a good transfection rate.

FIG. 4: illustrates stability experiments with regard to electrostatic displacement of the bound nucleic acid from the complex. As can be seen the addition of the anionic polymer heparin can not displace the RNA from the complex because it still migrates in the gel. This indicates that the complex binding is so strong that a competitive complex partner cannot displace the RNA from the complex. The content of lanes 1-4 are indicated in the Figure from left to right (lanes 1-4).

Figure 5:
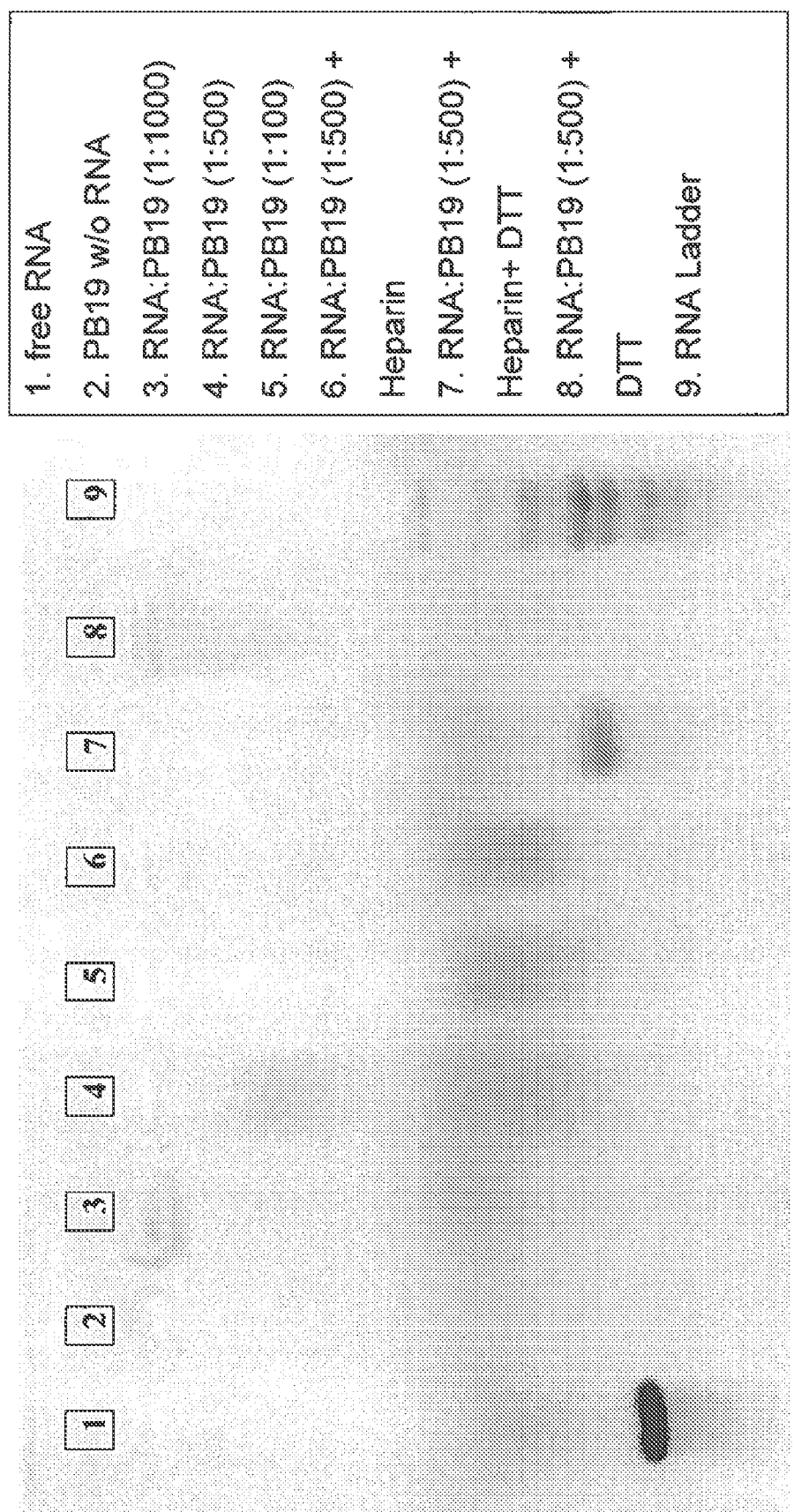

FIG. 5: depicts a gel shift assay to examine the strength of complex binding. It could be shown that the addition of the anionic polymer heparin or the reducing agent DTT alone cannot display the RNA from the complex with the polymer according to the invention (PB19). Only together they are able to displace the RNA from the complex (lane 7). This indicates that the complex binding is so strong that neither a competitive complex partner nor a reducing agent can displace the RNA from the complex.

Figure 6:
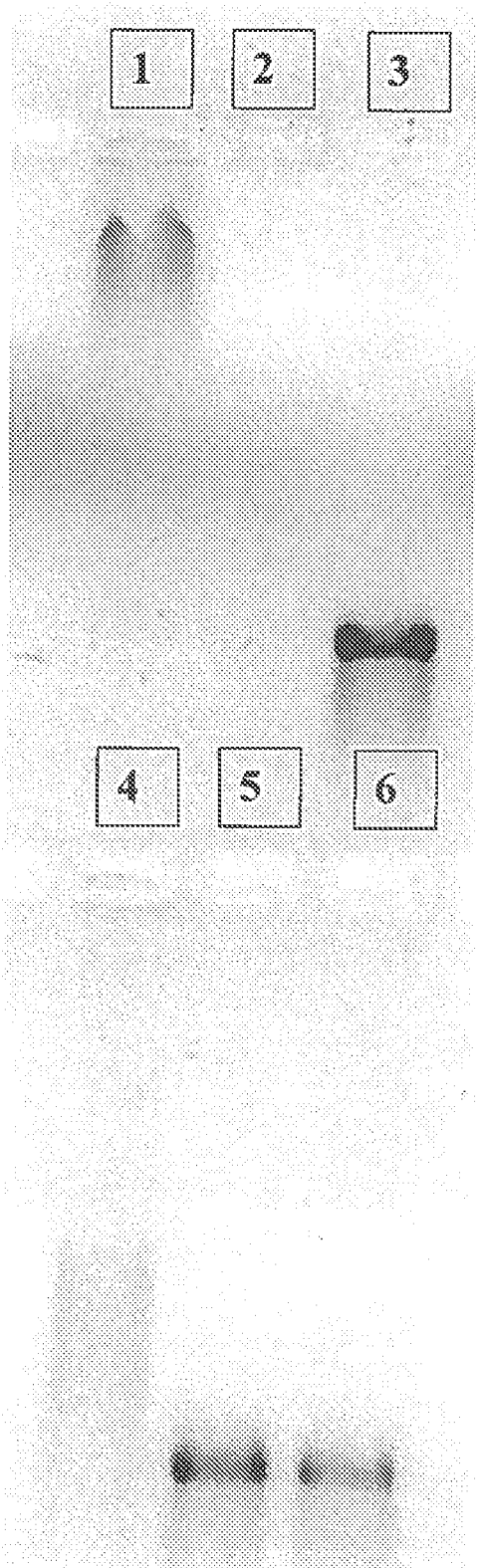

FIG. 6: shows a gel shift assay to examine the strength of complex binding. As can be seen, the addition of the anionic polymer heparin alone cannot displace the RNA from the complex with polymers according to the invention (PB22). In contrast mRNA could be readily displaced by heparin from PEI complexes.

Figure 7:
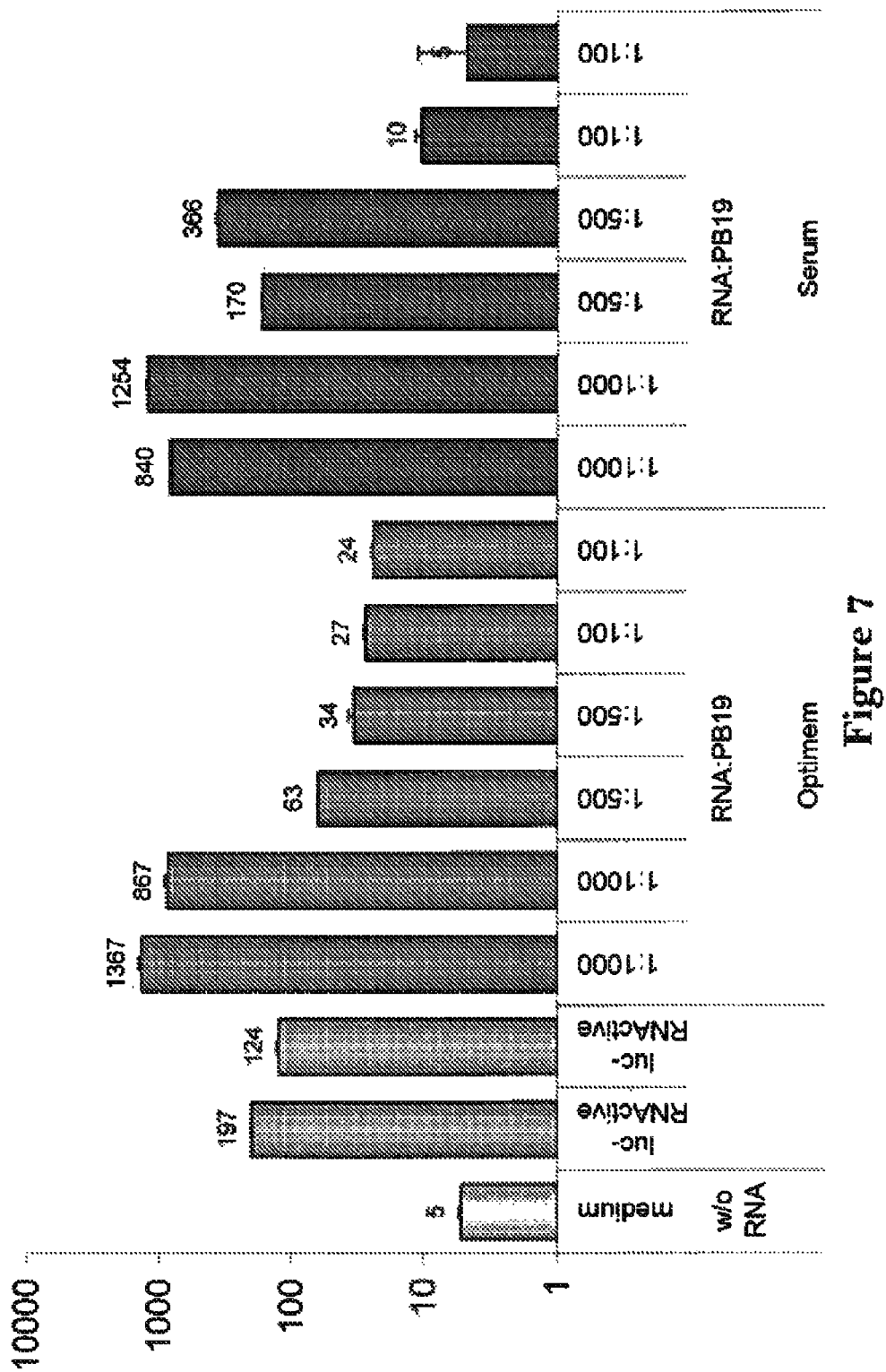

FIG. 7: depicts the results from expression experiments with of luciferase encoding mRNA according to SEQ ID NO: 369 in HeLa cells. As can be seen, formulations of mRNA coding for luciferase (luc-RNActive) according to SEQ ID NO: 369 with the PB19 polymer (molar ratio of RNA:PB19 1:1000, 1:500, 1:100) lead to expression of luciferase independently of the presence of serum containing medium. These results are unexpected because serum containing medium leads in general to a loss of transfection efficiency.

Figure 8:
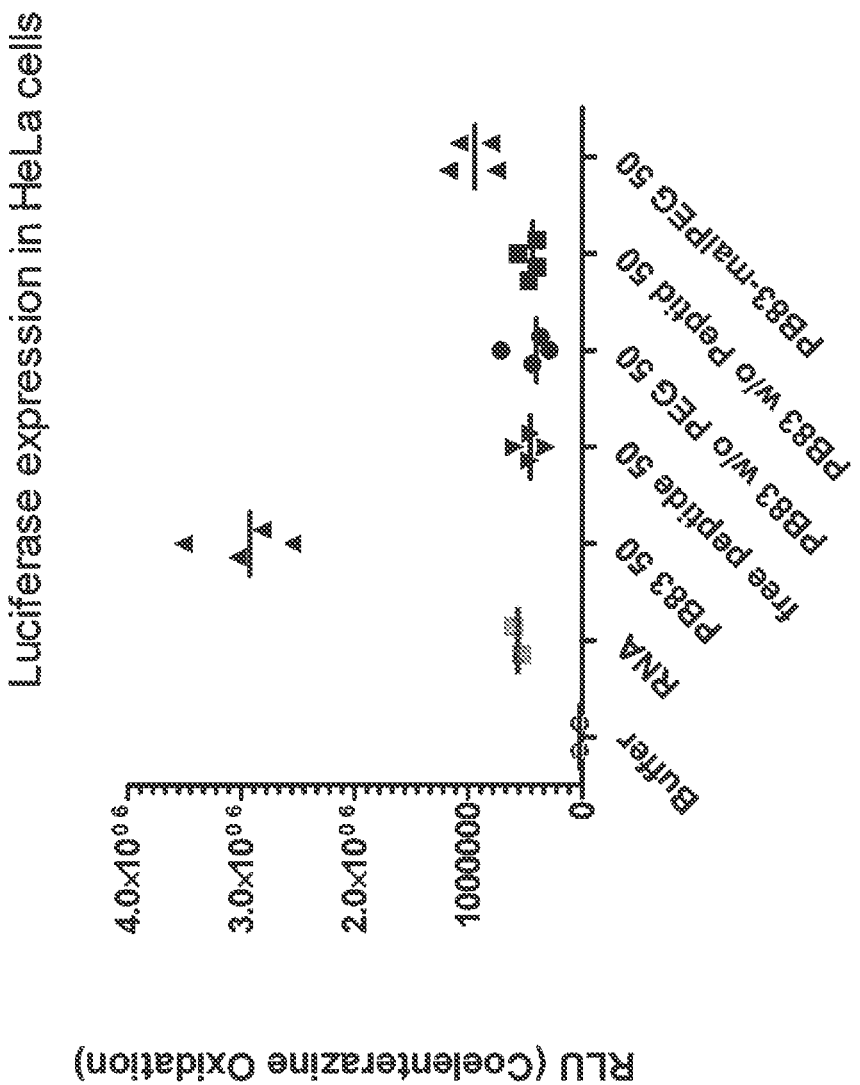

FIG. 8: depicts the results from expression experiments with of luciferase encoding mRNA according to SEQ ID NO: 369 in HeLa cells. As can be seen, formulations of mRNA coding for luciferase (luc-RNActive) according to SEQ ID NO: 369 with the PB83 polymer (molar ratio of RNA:PB83 1:50) lead to significant higher expression of luciferase compared to th free peptide combined with RNA in molar ratio 1:50 (e.g. template assisted polymerization in situ Rice et. Al.), to the non-pegylated polymerization product PB83 w/o PEG in molar ratio 1:50 (e.g. RPC conform), PB83 polymerization without peptide component (e.g. dimerized PEG-SS-PEG) and a non-reversible PEGylated of PB83 derivative which was synthesized by malimide containing PEG termination of the polymerization reaction.

FIG. 9A: illustrates the results from expression experiments with luciferase encoding mRNA according to SEQ ID NO: 369 in BALB/c mice after intradermal injection. As a result, formulation of mRNA coding for luciferase (luc- RNActive) according to SEQ ID NO: 369 with the PB19 polymer leads to expression of luciferase in the dermis of female BALB/c mice. Other transfection reagents known in the art (PEI and Lipofectamine 2000) did not show any expression of the Luciferase protein.

FIG. 9B: illustrates the results from expression experiments with luciferase encoding mRNA according to SEQ ID NO: 369 in BALB/c mice after intramuscular injection. As a result, formulation of mRNA coding for luciferase (luc-RNActive) according to SEQ ID NO: 369 with the PB19 polymer leads to expression of luciferase in the m. tibialis of female BALB/c mice. Other transfection reagents known in the art (PEI and Lipofectamine 2000) did not show any expression of the Luciferase protein.

Figure 10:
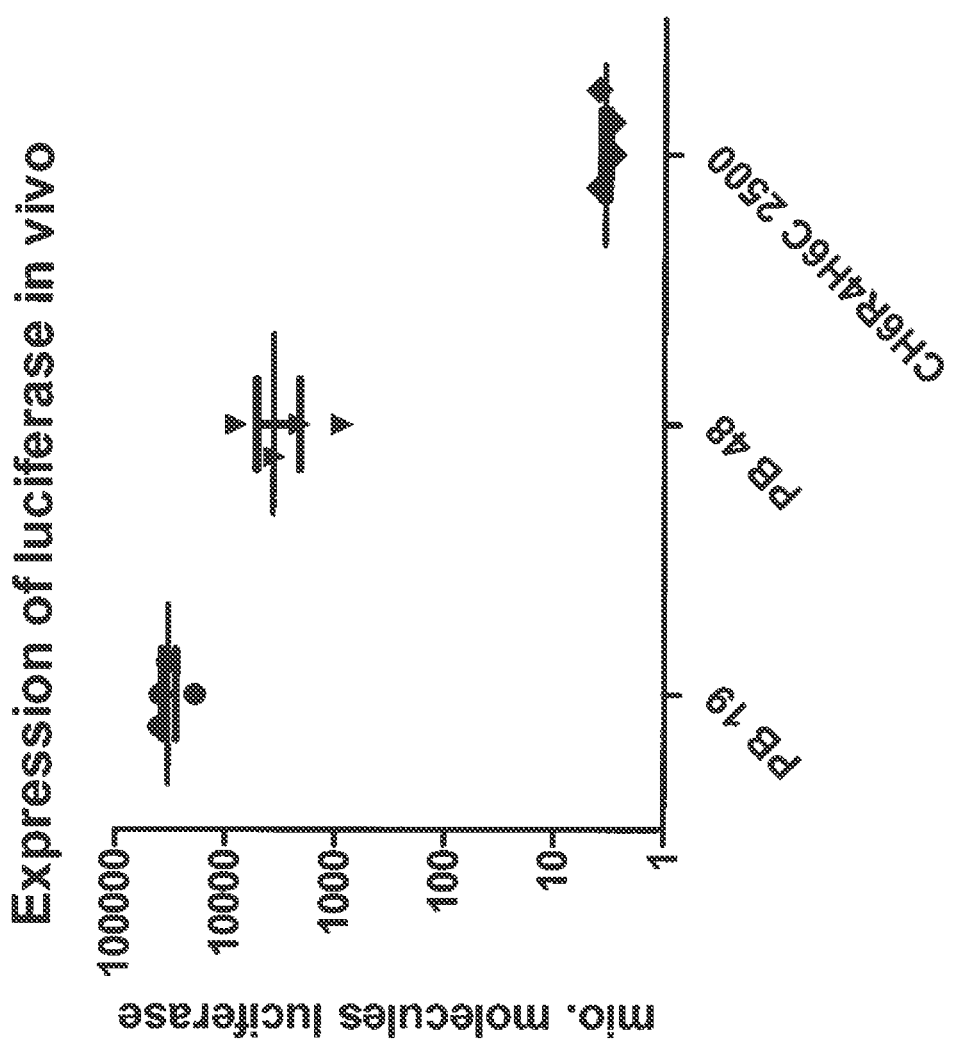

FIG. 10: shows the expression of luciferase in BALB/c mice after intradermal injection of different formulations of mRNA coding for luciferase (luc-RNActive) according to SEQ ID NO: 369 with two different polymers according to the invention [PB19 and PB48]. These formulations of mRNA coding for luciferase (luc-RNActive) according to SEQ ID NO: 369 with two different polymers according to the invention [PB19 and PB48] lead to expression of luciferase in the dermis of female BALB/c mice. The polymeric carrier cargo complex formed by a peptide according to RPC CH6R4H6C (without PEGylation) and mRNA coding for luciferase (luc-RNActive) according to SEQ ID NO: 369 in a molar ratio of 2500:1 showed no expression of luciferase after intradermal injection of the complexed mRNA.

Figure 11:
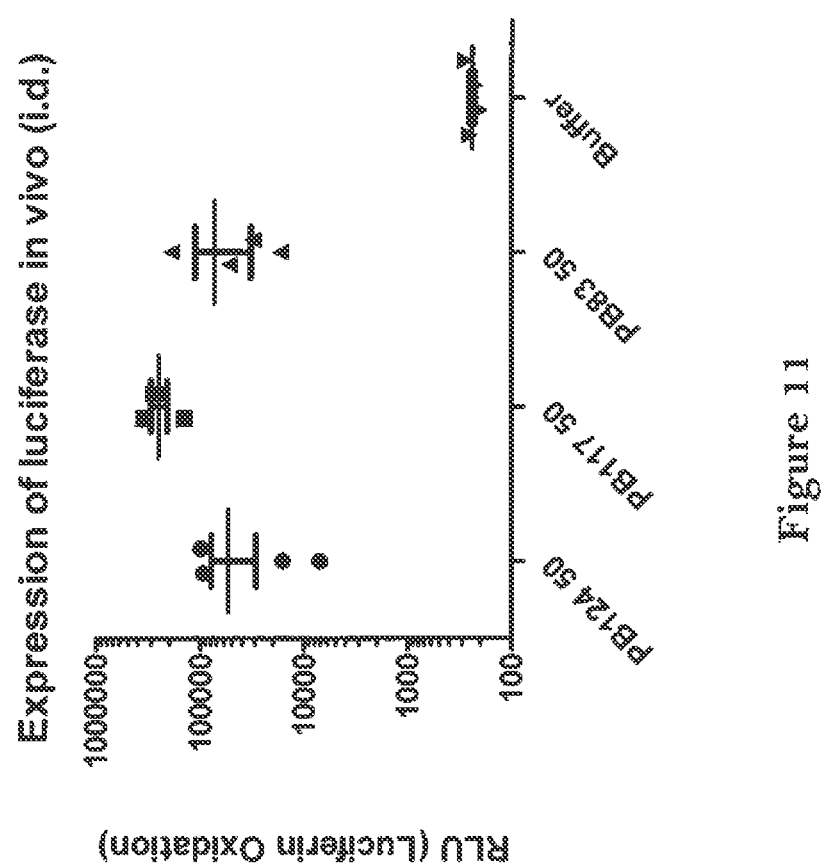

FIG. 11: shows the expression of luciferase in BALB/c mice after intradermal injection of different formulations of mRNA coding for luciferase (luc-RNActive) according to SEQ ID NO: 369 with three different polymers according to the invention [PB124, PB117 and PB83]. These formulations lead all to an expression of luciferase in the dermis of female BALB/c mice.

Figure 12:
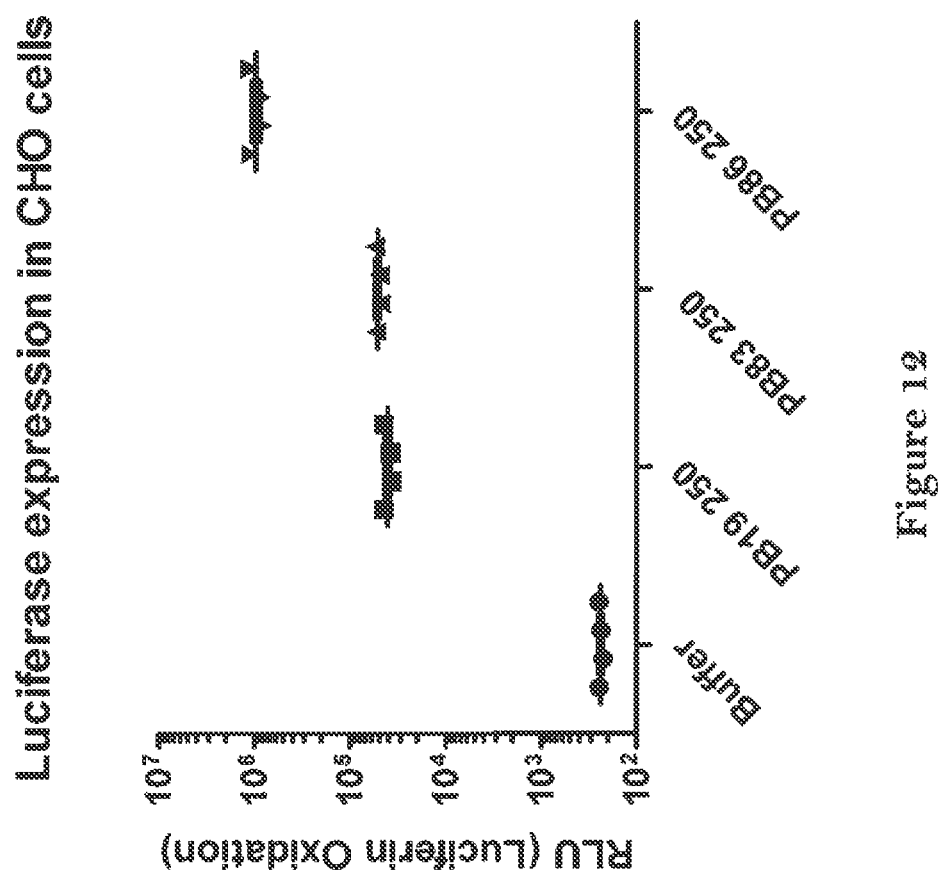

FIG. 12: depicts the results from expression experiments with of luciferase encoding mRNA according to SEQ ID NO: 369 in CHO cells. As can be seen, formulations of mRNA coding for luciferase (luc-RNActive) according to SEQ ID NO: 369 with different polymers according to the invention (molar ratio of RNA:PB 1:250) all lead to high levels of luciferase expression in serum containing medium. Also the advantageous effect of the hydrophilic component AA (in this case the peptide $CAS_3PS_3AC$ in the polymer can easily be seen.

Figure 13:
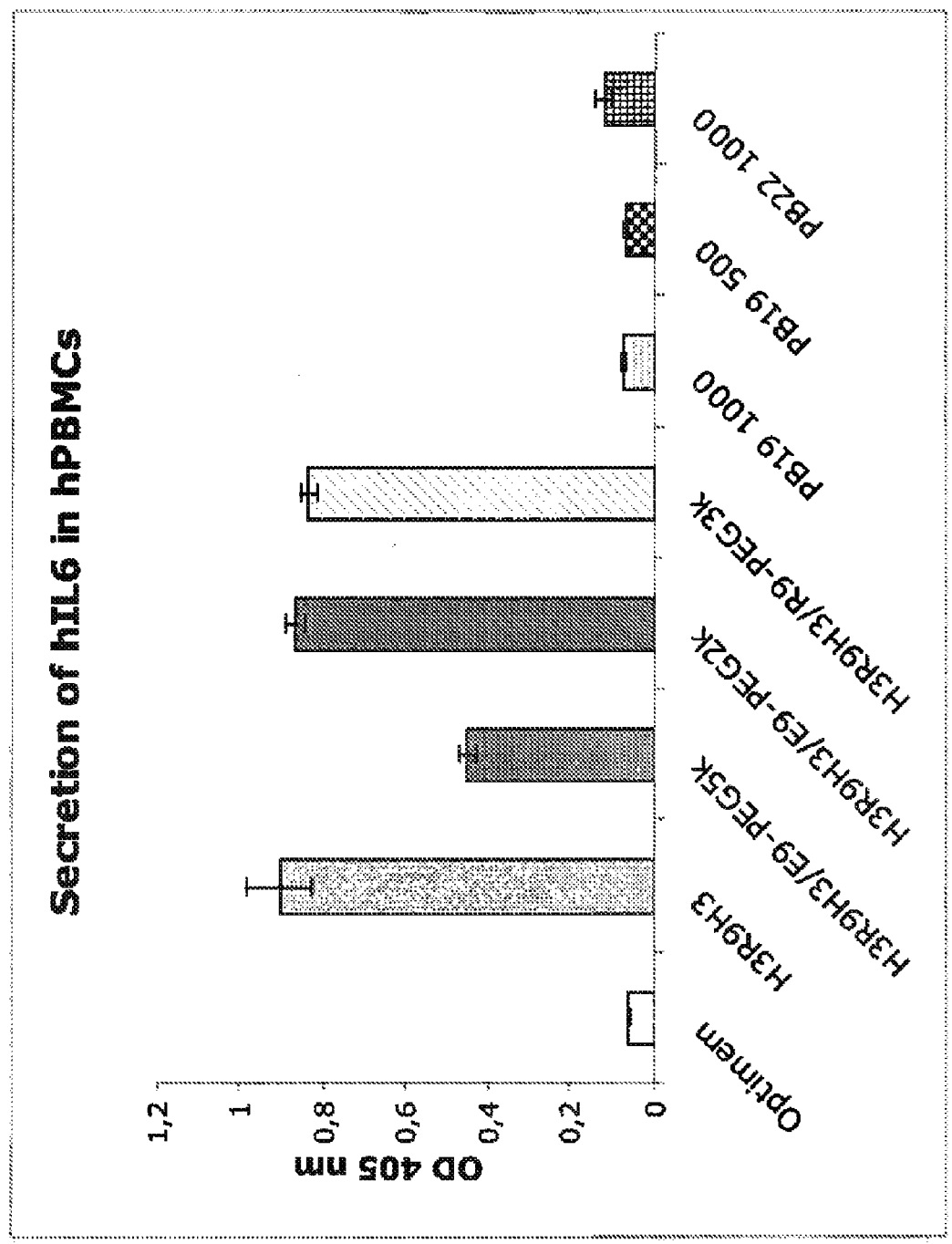

FIG. 13: depicts the secretion of hIL-6 cytokine in hPB-MCs. It could be shown that complexes consisting of the polymers according to the invention (PB19 and PB22) and mRNA coding for luciferase (luc-RNActive) according to SEQ ID NO: 369 do not induce the secretion of cytokines in hPBMCs in contrast to complexes consisting of mRNA coding for luciferase (luc-RNActive) according to SEQ ID NO: 369 and cationic peptides (H3R9H3) or a combination of cationic peptides (H3R9H3) and PEGylated cationic peptides (which confers in general to subsequent hydrophilic coating of pre-formed nucleic acid condensates). The polymers used were:

E9-PEG5k: HO-PEG$_{5000}$-EEEEEEEE
E9-PEG3k: HO-PEG$_{3000}$-EEEEEEEE
R9-PEG3k: HO-PEG$_{3000}$-RRRRRRRRR
PB19: HO-PEG$_{5000}$-S—(S—CHHHRRRRHHHC—S)$_5$—S-PEG$_{5000}$-OH
PB22: HO-PEG$_{5000}$-S—(S—CHHHHHHRRRRHHHH-HHC—S)$_5$-S—PEG$_{5000}$-OH

Figure 14:
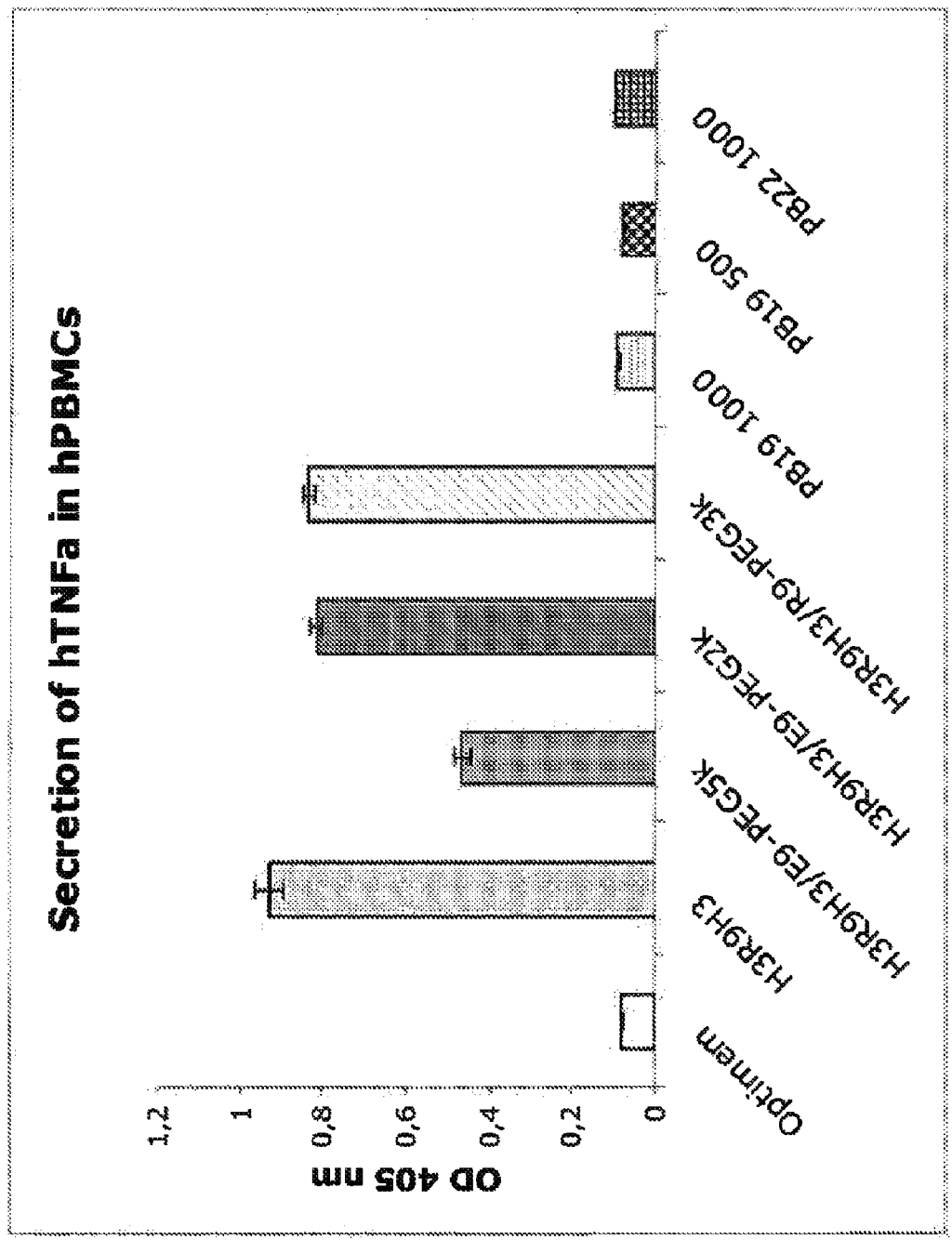

FIG. 14: illustrates the secretion of hTNFa cytokine in hPBMCs. It could be shown that complexes consisting of the polymers according to the invention (PB19 and PB22) and mRNA coding for luciferase (luc-RNActive) according to SEQ ID NO: 369 do not induce the secretion of cytokines in hPBMCs in contrast to complexes consisting of mRNA coding for luciferase (luc-RNActive) according to SEQ ID NO: 369 and cationic peptides (H3R9H3) or such complexes coated with PEGylated peptides (which confers in general to subsequent hydrophilic coating of pre-formed nucleic acid condensates). The polymers used were:

E9-PEG5k: HO-PEG$_{5000}$-EEEEEEEE
E9-PEG3k: HO-PEG$_{3000}$-EEEEEEEE
R9-PEG3k: HO-PEG$_{3000}$-RRRRRRRRR
PB19: HO-PEG$_{5000}$-S—(S—CHHHRRRRHHHC—S)$_5$—S-PEG$_{5000}$-OH
PB22: HO-PEG$_{5000}$-S—(S—CHHHHHHRRRRHHHH-HHC-5)$_5$-S—PEG$_{5000}$-OH

Figure 15:
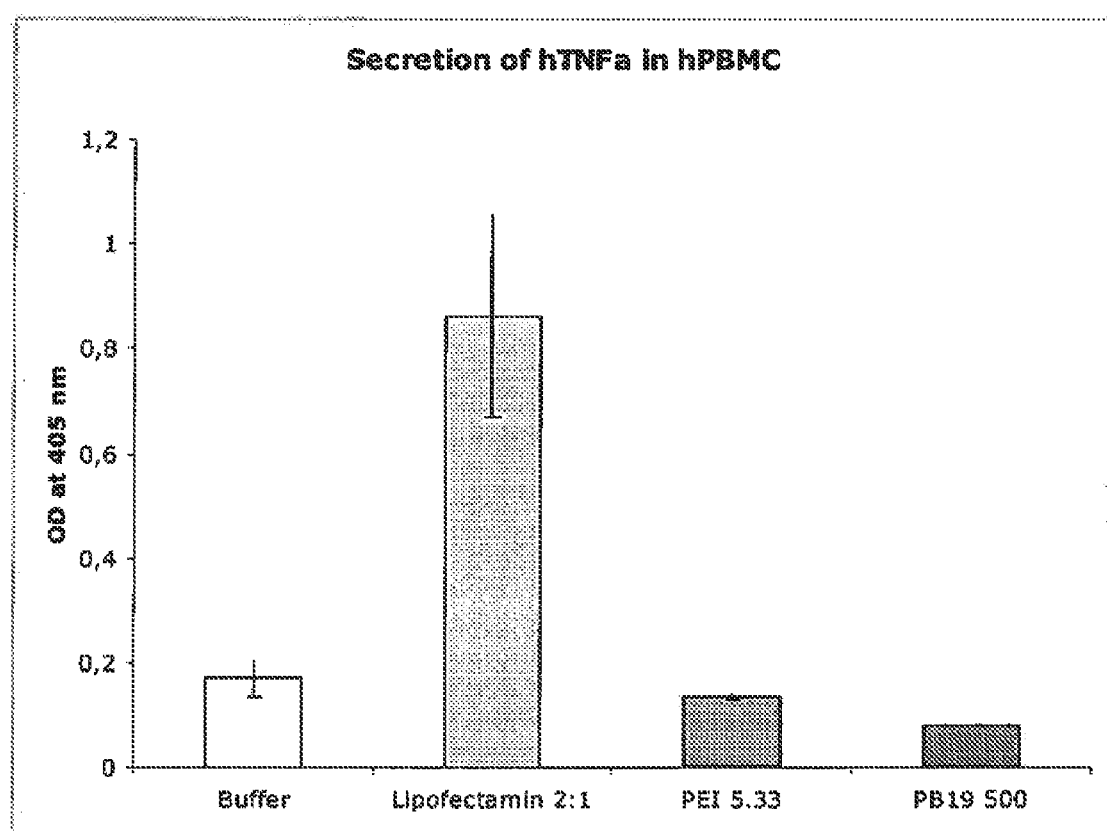

FIG. 15: shows the secretion of hTFNa cytokine secretion in hPBMCs. It could be shown that complexes consisting of mRNA coding for luciferase (luc-RNActive) according to SEQ ID NO: 369 and polymers according to the invention (PB19) do not induce the secretion of hTFNa in hPBMCs in contrast to complexes consisting of mRNA coding for luciferase (luc-RNActive) according to SEQ ID NO: 369 and state of the art transfection reagents like Lipofectamin 2000.

FIG. 16: shows the mRNA sequence encoding *Photinus pyralis* luciferase (SEQ ID NO: 369) in the mRNA construct pCV19-Pp luc(GC)-muag-A70-C30; which exhibits a length of 1857 nucleotides. The mRNA sequence contains following sequence elements:

the coding sequence encoding *Photinus pyralls* luciferase;
stabilizing sequences derived from alpha-globin-3'-UTR (muag (mutated alpha-globin-3'-UTR));
70× adenosine at the 3'-terminal end (poly-A-tail);
30× cytosine at the 3'-terminal end (poly-C-tail).
The ORF is indicated in italic letters, muag (mutated alpha-globin-3'-UTR is indicated with a dotted line, the poly-A-tail is underlined with a single line

EXAMPLES

The following examples are intended to illustrate the invention further. They are not intended to limit the subject matter of the invention thereto.

1. Preparation of DNA and mRNA Constructs Encoding Pp Luciferase (*Photinus pyralis*)

For the present examples DNA sequences, encoding *Photinus pyralis* luciferase, were prepared and used for subsequent in vitro transcription reactions.

According to a first preparation, the DNA sequence termed pCV19-Ppluc(GC)-muag-A70-C30 sequence was prepared, which corresponds to the *Photinus pyralis* luciferase coding sequence. The construct was prepared by modifying the wildtype *Photinus pyralis* luciferase encoding DNA sequence by introducing a GC-optimized sequence for a better codon usage and stabilization, stabilizing sequences derived from alpha-globin-3'-UTR (muag (mutated alpha-globin-3'-UTR)), a stretch of 70× adenosine at the 3'-terminal end (poly-A-tail) and a stretch of 30× cytosine at the 3'-terminal end (poly-C-tail), leading to SEQ ID NO: 369 (see FIG. 16). The sequence of the final DNA construct had a length of 1857 nucleotides and was termed "pCV19-Ppluc (GC)-muag-A70-C30". In SEQ ID NO: 369 (see FIG. 16) the sequence of the corresponding mRNA is shown.

The sequence contains following sequence elements:
the coding sequence encoding *Photinus pyralis* luciferase;
stabilizing sequences derived from alpha-globin-3'-UTR (muag (mutated alpha-globi n-3'-UTR));
70× adenosine at the 3'-terminal end (poly-A-tail);
30× cytosine at the 3'-terminal end (poly-C-tail).

2. In Vitro Transcription:

The respective DNA plasmid prepared according to Example 1 was transcribed in vitro using T7-Polymerase. Subsequently the mRNA was purified using PureMessenger® (CureVac, Tubingen, Germany).

3. Reagents:

Peptides: The peptides used in the present experiments were as follows:
PB19: HO-PEG$_{5000}$-S—(S—CHHHRRRRHHHC—S)$_5$—S-PEG$_{5000}$-OH (pegylated CH$_3$R$_4$H$_3$C peptide polymer)
PB22: HO-PEG$_{5000}$-S—(S—CHHHHHHRRRRHHHH-HHC—S)$_5$—S-PEG$_{5000}$-OH (pegylated CH$_6$R$_4$H$_6$C peptide polymer)
PB48: HO-PEG$_{5000}$-S—(S—CHHHRRRRHHHC—S)$_3$—S-PEG$_{5000}$-OH
PB83: HO-PEG$_{5000}$-S—(S—CHHHHHHRRRRHHHH-HHC—S-)$_7$-S-PEG$_{5000}$-OH
PB86: HO-PEG$_{5000}$-S—(S—CHHHHHHRRRRHHHH-HHC—S-)$_5$(S-CAS3PS3AC—S)$_5$—S-PEG$_{5000}$-OH
PB117 HO-PEG$_{5000}$-S—(S—CHKKKKKKHC—S-)$_7$-S-PEG$_{5000}$-OH
PB124 HO-PEG$_{2000}$-S—(S—CHHHHHHRRRRHHHH-HHC—S-)$_7$-S-PEG$_{2000}$-OH
PB83 free peptide HS—(CHHHHHHRRRRHHHH-HHC)—SH freshly solved in water prior formulation
PB83 w/o peptide PEG-SS-PEG
PB83 w/o PEG HS—(CHHHHHHRRRRHHHHHC)—SH
PB83malPEG PEG-mal-(S—CHHHHHHRRRRHHHH-HHC—S-)$_x$-mal-PEG
H3R9H3: HHHRRRRRRRRRHHH
CH6R4H6C: H—(S—CHHHHHHRRRRHHHHHC—S)$_5$—H Further Tranfection Reagents Used are:
Lipofectamine 2000 (Invitrogen)
PEI 25 kDa (branched) (Aldrich)

4. Synthesis of the Inventive Polymeric Carrier:

The condensation reaction was performed with the calculated amount of peptide (component P$^2$) which is dissolved in a mixture of a buffered aqueous solution at pH 8.5 with an optional additive of 5% (v/v) Dimethylsulfoxide (DMSO) (which are mild oxidation conditions and therefore allow the establishment of an equilibrium) and stirred for 18 h at ambient temperature. Afterwards the calculated amount of a thiol group containing PEG derivative (alpha-Methoxy-omega-mercapto poly(ethylene glycol)) (component P$^1$) (dissolved in water) is added and the resulting solution is stirred for another 18 h. Subsequent lyophilisation and purification yield the desired polymer. The ratio between PEG component P$^1$ to peptide component P$^2$ defines the chain length of the P$^2$ polymer.

The condensation reaction in this reaction environment is reversible, therefore the chain length of the polymer is determined by the amount of the monothiol compound which terminates the polymerisation reaction. In summary the length of the polymer chain is determined by the ratio of oligo-peptide and monothiol component. This reaction is supported by the chosen mild oxidation conditions. With more stringent oxidation conditions (30% DMSO) the generation of high molecular (long chain) polymers is induced.

4.1. 1. Step: Exemplary Polymerization Reaction:

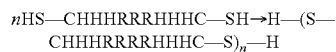

4.2. 2. Step: Exemplary Stop Reaction:

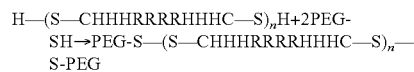

4.3. Exemplary Synthesis Reaction:

step 1)

step 2)

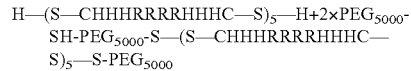

To achieve a polymer length of 5 (n=5), a molar ratio of peptide:PEG of 5:2 was used.

Some variations of the synthesis reaction were done to show the the effect of the PEGchains and the effects of the reversible attachment of the PEG chains.

4.4. Synthesis Reaction for Polymeric Carriers without PEG Chains:

The reaction conditions are the same as mentioned above, but the step of the addition of a sulfhydryl containing PEG derivative is not performed/skipped.

4.5. Synthesis Reaction for Irreversible Attached PEG Chains:

The reaction conditions are the same as mentioned above, but instead of a sulfhydryl containing PEG derivative a maleimide containing PEG derivative is utilized. The maleimide mojety reacts rapidly with free sulfhydryl groups forming a covalent bond. Therefore the termination of the polymerization is not under the dynamic equilibria conditions as for sulfhyrdyl containing PEG derivatives but under irreversible conditions which results in a "frozen" polymerization pattern of high polydiversity and not the defined reaction products of the dynamic equilibria reaction.

5. Complexation of RNA:

The mRNA construct defined above in Example 1 and prepared according to Example 2, were complexed for the purposes of the present invention with the polymers, preferably as defined in Example 4. Therefore, 4 μg RNA coding for luciferase pCV19-Ppluc(GC)-muag-A70-C30 (Luc-RNActive) according to SEQ ID NO: 85 were mixed in molar ratios as indicated with the inventive polymeric carrier (according to formula I) or a control, thereby forming a complex. Afterwards the resulting solution was adjusted with water to a final volume of 50 μl and incubated for 30 minutes at room temperature.

The different inventive polymeric carriers and the different ratios of polymeric carriers/RNA used in this experiment are shown in table 1.

| Präfix | Polymer | Ratio | Cationic AS | N/P |
|---|---|---|---|---|
| PB19 | HO-PEG$_{5000}$-S-(S-CHHHRRRRHHHC-S)$_5$-S-PEG$_{5000}$-OH | 500 | 20 | 5.6 |
| PB19 | HO-PEG$_{5000}$-S-(S-CHHHRRRRHHHC-S)$_5$-S-PEG$_{5000}$-OH | 250 | 20 | 2.8 |
| PB19 | HO-PEG$_{5000}$-S-(S-CHHHRRRRHHHC-S)$_5$-S-PEG$_{5000}$-OH | 50 | 20 | 0.6 |
| PB48 | HO-PEG$_{5000}$-S-(S-CHHHRRRRHHHC-S)$_3$-S-PEG$_{5000}$-OH | 250 | 12 | 1.67 |
| PB76 | HO-PEG$_{5000}$-S-(S-CHHHHHHRRRRHHHHHHC-S)$_{10}$-S-PEG$_{5000}$-OH | 500 | 40 | 11.2 |
| PB76 | HO-PEG$_{5000}$-S-(S-CHHHHHHRRRRHHHHHHC-S)$_{10}$-S-PEG$_{5000}$-OH | 250 | 40 | 5.6 |
| PB76 | HO-PEG$_{5000}$-S-(S-CHHHHHHRRRRHHHHHHC-S)$_{10}$-S-PEG$_{5000}$-OH | 50 | 40 | 1.1 |
| PB83 | HO-PEG$_{5000}$-S-(S-CHHHHHHRRRRHHHHHHC-S-)$_7$-S-PEG$_{5000}$-OH | 250 | 28 | 2.8 |
| PB86 | HO-PEG$_{5000}$-S-(S-CHHHHHHRRRRHHHHHHC-S-)$_5$(S-CAS3PS3AC-S)$_5$-S-PEG$_{5000}$-OH | 250 | 20 | 2.8 |

Ratio = molar ratio of RNA:peptide cationic AS = cationic amino acids, which are positively charged at a physiological pH (i.e. not histidine (H) but e.g. arginine (R)) Whereas PB83 and PB86 have a cationic insert that is double in size compared to PB19, therefore has double as much cationic amino acid residues. PB48 has a shorter cationic insert compared to PB19, therefore has less cationic amino acid residues per molecule polymer.

N/P = is the ratio of basic nitrogen atoms in the polymeric carrier to phosphate residues in the nucleic acid, considering that nitrogen atoms confer to positive charges and phosphate of the phosphate backbone of the nucleic acid confers to the negative charge. Histidine residues are counted neutral, because complex formation is done at physiological pH, therefore the imidazole residue is uncharged.

N/P is calculated by the following formula:
$$N/P = \frac{\text{pmol [RNA]} * \text{ratio} * \text{cationic AS}}{\mu g \; RNA * 3 * 1000}$$

For the calculations RNA coding for luciferase pCV19-Ppluc(GC)-muag-A70-C30 (Luc-RNActive) according to SEQ ID NO: 369 was applied, which has a molecular weight of 660 kDa. Therefore 1 μg pCV19-Ppluc(GC)-muag-A70-C30 RNA according to SEQ ID NO: 369 confers to 1.67 pmol pCV19-Ppluc(GC)-muag-A70-C30 RNA according to SEQ ID NO: 369

6. Size and Zetapotential Measurements:

The hydrodynamic diameters of polyplexes as prepared above were measured by dynamic light scattering using a Zetasizer Nano (Malvern Instruments, Malvern, UK) according to the SOPs distributed by Malvern. The measurements were performed at 25° C. in the specified buffer analysed by a cumulant method to obtain the hydrodynamic diameters and polydispersity indices of the polyplexes.

The Zeta potential of the polyplexes was evaluated by the laser Doppler electrophoresis method using a Zetasizer Nano (Malvern Instruments, Malvern, UK). The measurement was performed at 25° C. and a scattering angle of 173° was used.

7. Gel Shift Assay

Furthermore, mRNA coding for luciferase (Luc-RNActive) according to SEQ ID NO: 369 was formulated with the polymers as indicated and aliquots were incubated with either heparin (100 μg) or Dithiothreitol (DTT) for 15 Minutes at 37° C. Afterwards electrophoresis was done on agarose gel and the nucleic acids were visualized by ethidium bromide staining.

8. Confocal Laser Scanning Microscopy

Confocal laser scanning microscopy was performed on an inverted LSM510 laser scanning microscope (Carl Zeiss, Germany) using a Plan-Apochromat 63x/1.4 N.A. lens. All analyses were performed with living, nonfixed cells grown in eight-well chambered cover slides (Nunc, Germany). For the detection of Alexa Fluor 647 labelled mRNA only the light of a 633-nm helium neon laser, directed over a UV/488/543/633 beam splitter in combination with a LP 650 long pass filter was used. Life cell microscopy was performed at room temperature.

For this purpose, L929 cells ($25 \times 10^3$/well) were seeded 1 day prior to transfection on 24-well microtiter plates leading to a 70% confluence when transfection was carried out. Cells were transfected with formulations containing 2 μg Alexa Fluor 647 labelled mRNA in 8 chamber well slides directly before conduction of the microscopy experiment.

8. Cytokinstimulation in hPBMC

HPBMC cells from peripheral blood of healthy donors were isolated using a Ficoll gradient and washed subsequently with 1×PBS (phosphate-buffered saline). The cells were then seeded on 96-well microtiter plates ($200 \times 10^3$/well). The hPBMC cells were incubated for 24 h with 10 μl of the RNA/carrier complex in X-VIVO 15 Medium (BioWhittaker). As RNA SEQ ID NO: 369 was used. The carriers were as shown above for generic formula (I). The immunostimulatory effect upon the hPBMC cells was measured by detecting the cytokine production (Interleukin-6; Tumor necrose factor alpha, Interferon alpha). Therefore, ELISA microtiter plates (Nunc Maxisorb) were incubated over night (o/n) with binding buffer (0.02% NaN$_3$, 15 mM Na$_2$CO$_3$, 15 mM NaHCO$_3$, pH 9.7), additionally containing a specific cytokine antibody. Cells were then blocked with 1×PBS, containing 1% BSA (bovine serum albumin). The cell supernatant was added and incubated for 4 h at 37° C. Subsequently, the microtiter plate was washed with 1×PBS, containing 0.05% Tween-20 and then incubated with a Biotin-labelled secondary antibody (BD Pharmingen, Heidelberg, Germany). Streptavidin-coupled horseraddish peroxidase was added to the plate. Then, the plate was again washed with 1×PBS, containing 0.05% Tween-20 and ABTS (2,2'-azino-bis(3-ethyl-benzthiazoline-6-sulfonic acid) was added as a substrate. The amount of cytokine was determined by measuring the absorption at 405 nm (OD 405) using a standard curve with recombinant cytokines (BD Pharmingen, Heidelberg, Germany) with the Sunrise ELISA-Reader from Tecan (Crailsheim, Germany).

9. Transfection of HeLa Cells:

4 μg RNA stabilized luciferase mRNA (Luc-RNActive) according to SEQ ID NO: 85 were mixed in molar ratios as indicated with the respective polymer (according to formula I), thereby forming a complex. Afterwards the resulting solution was adjusted with water to a final volume of 50 μl and incubated for 30 minutes at room temperature. The used ratios are indicated in table 1 above.

Hela-cells ($150 \times 10^3$/well) were seeded 1 day prior to transfection on 24-well microtiter plates leading to a 70% confluence when transfection was carried out. For transfection 50 μl of the RNA/carrier complex solution were mixed with 250 μl serum free or FCS containing medium (as indicated in the provided table) and added to the cells (final RNA concentration: 13 μg/ml). Prior to addition of the serum free transfection solution the HeLa-cells were washed gently and carefully 2 times with 1 ml Optimen (Invitrogen) per well. Then, the transfection solution (300 μl per well) was added to the cells and the cells were incubated for 4 h at 37° C. Subsequently 300 μl RPMI-medium (Camprex)

containing 10% FCS was added per well and the cells were incubated for additional 20 h at 37° C. The transfection solution was sucked off 24 h after transfection and the cells were lysed in 300 μl lysis buffer (25 mM Tris-PO$_4$, 2 mM EDTA, 10% glycerol, 1% Triton-X 100, 2 mM DTT). The supernatants were then mixed with luciferin buffer (25 mM Glycylglycin, 15 mM MgSO$_4$, 5 mM ATP, 62.5 μM luciferin) and luminiscence was detected using a luminometer (Lumat LB 9507 (Berthold Technologies, Bad Wildbad, Germany)).

10. Expression of Luciferase In Vivo:

10 μg mRNA coding for luciferase (Luc-RNActive) according to SEQ ID NO: 369 were mixed in a molar ratio of 1:250 (RNA:polymeric carrier) with the respective carrier (according to formula I), thereby forming a complex. Afterwards the resulting solution was adjusted with Ringer Lactate solution to a final volume of 100 μl and incubated for 30 minutes at room temperature, yielding a solution with a 0.1 g/l concentration of complexed RNA.

100 μl (20 μl) of this solution was administrated intradermally (ear pinna or back) or intramuscularly (m. tibialis) to 7 week old BALB/c mice. After 24 h the mice were sacrificed and the samples (ear, skin from the back or muscle) were collected, frozen at −78° C. and lysed for 3 Minutes at full speed in a tissue lyser (Qiagen, Hilden, Germany). Afterwards 600 μl of lysis buffer were added and the resulting solutions were subjected another 6 minutes at full speed in the tissue lyser. After 10 minutes centrifugation at 13500 rpm at 4° C. the supernatants were mixed with luciferin buffer (25 mM Glycylglycin, 15 mM MgSO4, 5 mM ATP, 62.5 μM luciferin) and luminiscence was detected using a luminometer (Lumat LB 9507 (Berthold Technologies, Bad Wildbad, Germany)).

11. Results:

11.1. DLS/Zetasizer Determinations:

The size and ζ-potential of the polymeric carrier cargo complexes according to the invention were evaluated in triplicates by dynamic light scattering (DLS) and laser-doppler electrophoresis and compared to different polymeric carrier cargo complexes known in the state of the art. Table 1 summarizes the cumulant diameters and the ζ-potential of the polymeric carrier cargo complexes.

| Polymeric carrier cargo complex | N/P | Cumulant diameter in water (nm) | Cumulant diameter in ringer lactate (nm) | ζ-potential (mV) |
|---|---|---|---|---|
| PB19 | 6 | 58 ± 2 | 81 ± 3 | −9 mV |
| PEI | 10 | 88 ± 4 | 110 ± 2 | +20 mV |
| RPC like polymer CH6R4H6C | 5 | 170 ± 8 | >1000 | +39 mV |

The cumulant diameters of the polymeric carrier cargo complexes formed by polymers according to the invention and mRNA coding for luciferase (Luc-RNActive) according to SEQ ID NO: 369 showed that small, uniform complexes were formed. These complexes are stable against agglomeration in salt containing buffer and are less than 100 nm in size. In contrast polymeric carrier cargo complexes according to the RPC procedure are unstable in salt containing buffers, forming large aggregates. The polymeric carrier cargo complexes according to the invention also form complexes of low ζ-potential, which is linked to a low tendency in binding components of the serum, and therefore have a low tendency for opsonisation.

11.2. Confocal Microscopy:

The transfection of L929 cells with AlexaFlour647 aminoallyl-labelled RNA complexed with the inventive polymer PB19 after 5 minutes already led to detectable complexes in the cell. The results are shown in FIGS. 2 and 3. As can be seen in FIG. 2, confocal microscopy of L929 cells 5 minutes after transfection with fluorescence labelled RNA (SEQ ID NO: 369) complexed with the inventive polymer PB19 in a molar ratio of 1:500 showed that already 5 minutes after transfection several complexes are detectable in the cells. After 1 h confocal microscopy of L929 cells 1 h after transfection with fluorescence labelled RNA complexed with the inventive polymer PB19 in a ratio of 1:500 revealed that after transfection most of the particles were taken up in the cells (see FIG. 3)

11.3. Stability Towards Electrostatic Displacement:

Since the complexes of the present invention, particularly the polymers according to formula (I) are unique with respect to their composition and their surface charge, unexpected results could be observed in gel shift assays. Normally, it is determined, as to whether a polymer condenses the nucleic acid and thus prevents the nucleic acid to migrate in an electrical field. If a complex partner is added, which exhibits a stronger affinity for the cationic polymer than the nucleic acid, the nucleic acid is displaced from the complex and again can migrate in an electrical field. For this purpose, PEI may be used, which is known to exhibit extremely strong complexes with nucleic acid.

In a gel shift assay to examine the strength of complex binding (see FIG. 4) it could be shown that the addition of the anionic polymer heparin can not displace the RNA from the inventive polymeric carrier cargo complex because it still migrates in the gel. This indicates that the complex binding is so strong that a competitive complex partner cannot displace the RNA from the inventive polymeric carrier cargo complex.

In a further a gel shift assay to examine the strength of complex binding (see FIG. 5) it could be shown that the addition of the anionic polymer heparin or the reducing agent DTT alone cannot display the RNA from the inventive polymeric carrier cargo complex with the polymer according to the invention (PB19). Only together they are able to display the RNA from the complex (lane 7). This indicates that the complex binding is so strong that neither a competitive complex partner nor a reducing agent can displace the RNA from the inventive polymeric carrier cargo complex.

Contrary to PEI complexes, the RNA is not released from the inventive polymeric carrier cargo complex upon addition of heparin. Only a combination of heparin and DTT releases the RNA. It is to be noted that DTT reduces disulfide bonds and thus destroys the conjugate. This imitates in vivo conditions, where the reducing conditions in the cell releases the RNA from the complex.

In comparison thereto, gel shift assays with PEI complexes to examine the strength of complex binding show that the addition of the anionic polymer heparin alone cannot displace the RNA from the complex with polymers used according to the present invention (PB22). In contrast mRNA could be readily displayed by heparin from PEI complexes (see FIG. 6).

11.4. Expression of Luciferase in HeLa Cells:

The expression of luciferase in HeLa cells was determined using a complex of a polymer according to formula (I) herein and an mRNA according to SEQ ID NO: 369 (mRNA coding for luciferase (luc-RNActive) with the PB19 carrier (molar ratio of RNA:PB19 1:1000, 1:500, 1:100).

These formulations of mRNA coding for luciferase (luc-RNActive) with the PB19 carrier (molar ratio of RNA:PB19 1:1000, 1:500, 1:100) lead to expression of luciferase independently of the presence of serum containing medium. These results are unexpected because serum containing medium leads in general to a loss of transfection efficiency.

11.5. Expression of Luciferase In Vivo:

Expression of luciferase in BALB/c mice was determined after intradermal injection. As can be seen in FIG. 9a, formulations of mRNA coding for luciferase (luc-RNActive) (SEQ ID NO: 369) with the PB19 polymer lead to expression of luciferase in the dermis of female BALB/c mice. Other transfection reagents known in the art (PEI and Lipofectamine 2000) did not show any expression of the Luciferase protein.

Furthermore, expression of luciferase in BALB/c mice after intramuscular injection was determined. As a result (see FIG. 9b), formulations of mRNA coding for luciferase (luc-RNActive) (SEQ ID NO: 369) with the PB19 polymer lead to expression of luciferase in the m. tibialis of female BALB/c mice. Other transfection reagents known in the art (PEI and Lipofectamine 2000) did not show any expression of the Luciferase protein.

Additionally, expression of luciferase in BALB/c mice after intradermal injection of different formulations was determined. As a result (see FIG. 10), formulations of mRNA coding for luciferase (luc-RNActive) (SEQ ID NO: 369) with two different polymers according to the present invention (polymers PB19 and PB48) lead to expression of luciferase in the dermis of female BALB/c mice. The polymeric carrier cargo complex formed by a peptide according to RPC CH6R4H6C (without PEGylation) and RNA in a molar ratio of 2500:1 procedure showed no expression of luciferase after intradermal injection of the complexed RNA.

11.6 Cytokine Stimulation in hPBMC

Cytokine stimulation, particularly hIL-6 cytokine secretion in hPBMCs was measured. As a result (see FIG. 13) it could be shown that the complexes according to the invention consisting of RNA (SEQ ID NO: 369) and polymers according to the invention (PB19 and PB22) do not induce the secretion of hIL-6 in hPBMCs in contrast to complexes consisting of RNA (SEQ ID NO: 369) and cationic peptides ($H_3R_9H_3$) or a combination of cationic peptides ($H_3R_9H_3$) and PEGylated peptides (E9 or R9) (which confers in general to subsequent hydrophilic coating of pre-formed nucleic acid condensates).

E9-PEG5k: HO-$PEG_{5000}$-EEEEEEEE
E9-PEG3k: HO-$PEG_{3000}$-EEEEEEEE
R9-PEG3k: HO-$PEG_{3000}$-RRRRRRRRR
PB19: HO-$PEG_{5000}$-S—(S—CHHHRRRRHHHC—S)$_5$—S-$PEG_{5000}$-OH
PB22: HO-$PEG_{5000}$-S—(S—CHHHHHHRRRRHHHH-HHC—S)$_5$—S-$PEG_{5000}$-OH

Furthermore, hTNFa cytokine secretion in hPBMCs was measured. The results show (see FIG. 14), that the complexes according to the invention consisting of RNA (SEQ ID NO: 369) and polymers according to the invention (PB19 and PB22) do not induce the secretion of hTNFα in hPBMCs in contrast to complexes consisting of RNA (SEQ ID NO: 369) and cationic peptides ($H_3R_9H_3$) or such complexes coated with PEGylated peptides (E9 or R9) (which confers in general to subsequent hydrophilic coating of pre-formed nucleic acid condensates).

E9-PEG5k: HO-$PEG_{5000}$-EEEEEEEE
E9-PEG3k: HO-$PEG_{3000}$-EEEEEEEE
R9-PEG3k: HO-$PEG_{3003}$-RRRRRRRRR
PB19: HO-$PEG_{5000}$-S—(S—CHHHRRRRHHHC—S)$_5$—S-$PEG_{5000}$-OH
PB22: HO-$PEG_{5000}$-S—(S—CHHHHHHRRRRHHHH-HHC—S)$_5$—S-$PEG_{5000}$-OH

Moreover, hIFNa cytokine secretion in hPBMCs was determined in a comparison of cytokine stimulating properties of complexes according to the invention consisting of RNA (SEQ ID NO: 369) and polymers according to the invention (PB19) to state of the art transfection reagents like Lipofectamin 2000 or PEI. As a result both Complexation with Lipofectamin 2000 and PEI lead to a high amount of secretion of hIFNa, whereas the complex according to the invention consisting of RNA (SEQ ID NO: 369) and polymers according to the invention (PB19 500) did not.

Furthermore, hTNFa cytokine secretion in hPBMCs was measured in a comparison of cytokine stimulating properties of complexes according to the invention consisting of RNA (SEQ ID NO: 369) and polymers according to the invention (PB19) to state of the art transfection reagents like Lipofectamin 2000 or PEI. As a result (see FIG. 15) Complexation with Lipofectamine 2000 leads to a high amount of secretion of hTNFα, whereas complexation with PEI or polymers according to the invention (PB19 500) did not.

The invention claimed is:

1. A pharmaceutical composition comprising:
   (A) a polymeric carrier molecule according to formula (I):

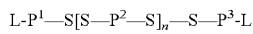

wherein,
   $P^1$ and $P^3$ are different or identical to each other and represent a linear or branched hydrophilic polyethylene glycol (PEG) polymer chain, wherein the hydrophilic PEG polymer chain exhibits a molecular weight of 1 kDa to 100 kDa;
   $P^2$ is a cationic or polycationic polypeptide, having a length of 3 to 100 amino acids, and comprising at least 2 cysteine residues;
   —S—S— is a (reversible) disulfide bond, wherein one of the sulfur positions of each of the disulfide bonds is provided by the at least 2 cysteine residues of the polypeptide of $P^2$;
   L is an optional ligand, which may be present or not, and may be selected independent from the other from a localization signal or sequence, an antibody, a cell penetrating peptide, a ligand of a receptor, small molecules, carbohydrates, or inhibitors or antagonists of receptors; and
   n is an integer, selected from a range of 1 to 50; and
   (B) an adjuvant component.

2. The pharmaceutical composition of claim 1, wherein the adjuvant component comprises cytokine, lipopolysaccharide (LPS) or toll-like receptor (TLR) ligand.

3. The pharmaceutical composition of claim 2, wherein the adjuvant component comprises a ligand of human TLR 1-10.

4. The pharmaceutical composition of claim 2, wherein the adjuvant component comprises LPS.

5. The pharmaceutical composition of claim 2, wherein the adjuvant component comprises granulocyte macrophage colony-stimulating factor (GM-CSF).

6. The pharmaceutical composition of claim 1, wherein the adjuvant component comprises CpG-DNA or an immunostimulatory RNA (isRNA).

7. The pharmaceutical composition of claim 1, wherein the adjuvant component comprises an immunostimulatory polypeptide.

8. The pharmaceutical composition of claim 1, wherein component P² of the polymeric carrier is selected from a peptide comprising a cationic peptide of formula (IIb):

Cys{(Arg)$_l$(Lys)$_m$(His)$_n$(Orn)$_o$(Xaa)$_x$}Cys, wherein
l+m+n+o+x=8-16, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 10% of all amino acids of the oligopeptide; and Xaa may be any amino acid selected from native or non-native amino acids except of Arg, Lys, His or Orn; and x may be any number selected from 0, 1, 2, 3, 4, 5, 6, 7, 8, 9, 10, 11, 12, 13 or 14, provided, that the overall content of Xaa does not exceed 90% of all amino acids of the oligopeptide.

9. The pharmaceutical composition of claim 1, wherein the polymeric carrier further comprises a nucleic acid molecule.

10. The pharmaceutical composition of claim 9, wherein the nucleic acid is provided in a molar ratio of 5 to 10000 of polymeric carrier molecule: nucleic acid.

11. The pharmaceutical composition of claim 9, wherein the nucleic acid is a DNA or a RNA.

12. The pharmaceutical composition of claim 9, wherein the nucleic acid is a mRNA, an siRNA, or an immunostimulatory RNA (isRNA).

13. The pharmaceutical composition of claim 9, wherein the nucleic acid is the adjuvant component of said composition and comprises an isRNA or CpG-DNA molecule.

14. The pharmaceutical composition of claim 9, wherein the nucleic acid encodes an antigen.

15. The pharmaceutical composition of claim 14, wherein the nucleic acid encodes a tumor antigen, or a pathogenic antigen.

16. The pharmaceutical composition of claim 9, wherein the nucleic acid encodes an immunostimulatory polypeptide.

17. The pharmaceutical composition of claim 1, wherein component P² comprises a cationic peptide of formula (IIb): CysHis6Arg4His6Cys (SEQ ID NO: 83).

18. The pharmaceutical composition of claim 1, wherein one of the sulfur positions of each of the disulfide bonds of formula (I) is provided by a cysteine residue at the N- or C-terminus of the polypeptide of P².

19. The pharmaceutical composition of claim 1, further comprising a lipid component.

20. The pharmaceutical composition of claim 19, wherein the lipid component comprises a cationic lipid.

21. The pharmaceutical composition of claim 1, wherein component P² is a cationic or polycationic polypeptide selected from a cell penetrating peptide (CPP), an HIV-binding peptide, a member of the penetratin family, or a protein transduction domain (PTD).

22. The pharmaceutical composition of claim 1, wherein L is (i) a localization signal or sequence selected from RGD, Transferrin, a signal peptide or signal sequence, or a nuclear localization signal or sequence (NLS), (ii) a small molecule selected from folate, a synthetic ligand or a small molecule agonist, (iii) TAT, (iv) a ligand of a receptor selected from a cytokine, a hormone, or a growth factor; a carbohydrate selected from mannose or galactose; or (v) an RGD peptidomimetic analog.

23. The pharmaceutical composition of claim 15, wherein the pathogenic antigen is an animal antigen, a viral antigen, a protozoal antigen, a bacterial antigen, an allergic antigen, an autoimmune antigen, or an allergen.

24. The pharmaceutical composition of claim 21, wherein (i) the CPP is protamine, nuceloline, spermine, spermidine, an L-oligomer, an arginine-rich peptide, a chimeric CPP, or a member of the penetratin family; (ii) the HIV-binding peptide is Tat.

25. The pharmaceutical composition of claim 24, wherein (i) the member of the penetratin family is Penetratin, pAntp, pIsl, Buforin-2, Bac715-24, SynB, SynB(1), pVEC, SAP, MAP, KALA, PpTG20, a proline-rich peptide, a Loligomere, an arginine-rich peptide, Calcitonin peptide, FGF, Lactoferrin, histone, VP22 peptide, or Herpes simplex virus VP22; (ii) the chimeric CPP is Transportan or an MGP peptide; (iii) the L-oligomer is poly-L-lysine; or (iv) the arginine-rich peptide is poly-arginine or oligoarginine.

* * * * *

UNITED STATES PATENT AND TRADEMARK OFFICE
CERTIFICATE OF CORRECTION

PATENT NO. : 9,907,862 B2
APPLICATION NO. : 15/065769
DATED : March 6, 2018
INVENTOR(S) : Patrick Baumhof and Thomas Schlake It is certified that error appears in the above-identified patent and that said Letters Patent is hereby corrected as shown below:

In the Claims

In Claim 17, Column 199, Line 40, delete "CysHis6Arg4His6Cys" and insert --$CysHis_6Arg_4His_6Cys$-- therefor.

Signed and Sealed this
Twenty-fourth Day of July, 2018

Andrei Iancu
*Director of the United States Patent and Trademark Office*

SEQUENCE LISTING

```
<160> NUMBER OF SEQ ID NOS: 369

<210> SEQ ID NO 1
<211> LENGTH: 7
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 1

Arg Arg Arg Arg Arg Arg Arg
1               5

<210> SEQ ID NO 2
<211> LENGTH: 8
<212> TYPE: PRT
<213> ORGANISM: Artificial Sequence
<220> FEATURE:
```

```
<223> OTHER INFORMATION: Description of artificial sequence: exemplary
      cationic peptide according to formula (II)

<400> SEQUENCE: 2

Arg Arg Arg Arg Arg Arg Arg Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 3

Arg Arg Arg Arg Arg Arg Arg Arg Arg
1               5

<210> SEQ ID NO 4
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 4

His His His Arg Arg Arg Arg Arg Arg Arg Arg Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 5

Arg Arg Arg Arg Arg Arg Arg Arg Arg His His His
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 6

His His His Arg Arg Arg Arg Arg Arg Arg Arg Arg His His His
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 7

Tyr Ser Ser Arg Arg Arg Arg Arg Arg Arg Arg Arg Ser Ser Tyr
1               5                   10                  15
```

-continued

```
<210> SEQ ID NO 8
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 8

Arg Lys His Arg Lys His Arg Lys His Arg Lys His
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 9

Tyr Arg Lys His Arg Lys His Arg
1               5

<210> SEQ ID NO 10
<211> LENGTH: 10
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 10

Arg Arg Arg Arg Arg Arg Arg Arg Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 11

Arg Arg Arg Arg Arg Arg Arg Arg Arg Arg Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 12

Arg Arg Arg Arg Arg Arg Arg Arg Arg Arg Arg Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 13
```

Arg Arg Arg Arg Arg Arg Arg Arg Arg Arg Arg Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 14

Arg Arg Arg Arg Arg Arg Arg Arg Arg Arg Arg Arg Arg Arg
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 15

Arg Arg Arg Arg Arg Arg Arg Arg Arg Arg Arg Arg Arg Arg Arg
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 16

Lys Lys Lys Lys Lys Lys Lys Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 17

Lys Lys Lys Lys Lys Lys Lys Lys Lys
1               5

<210> SEQ ID NO 18
<211> LENGTH: 10
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 18

Lys Lys Lys Lys Lys Lys Lys Lys Lys Lys
1               5                   10

<210> SEQ ID NO 19
<211> LENGTH: 11
<212> TYPE: PRT
<213> ORGANISM: Artificial Sequence

```
<220> FEATURE:
<223> OTHER INFORMATION: Description of artificial sequence: exemplary
      cationic peptide according to formula (II)

<400> SEQUENCE: 19

Lys Lys Lys Lys Lys Lys Lys Lys Lys Lys Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 20

Lys Lys Lys Lys Lys Lys Lys Lys Lys Lys Lys Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 21

Lys Lys Lys Lys Lys Lys Lys Lys Lys Lys Lys Lys Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 22

Lys Lys Lys Lys Lys Lys Lys Lys Lys Lys Lys Lys Lys Lys
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 23

Lys Lys Lys Lys Lys Lys Lys Lys Lys Lys Lys Lys Lys Lys Lys
1               5                   10                  15

<210> SEQ ID NO 24
<211> LENGTH: 8
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 24

His His His His His His His His
1               5
```

<210> SEQ ID NO 25
<211> LENGTH: 9
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 25

His His His His His His His His His
1               5

<210> SEQ ID NO 26
<211> LENGTH: 10
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 26

His His His His His His His His His His
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 27

His His His His His His His His His His His
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 28

His His His His His His His His His His His His
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 29

His His His His His His His His His His His His His
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of artificial sequence: exemplary
      cationic peptide according to formula (II)

```
<400> SEQUENCE: 30

His His His His His His His His His His His His His
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 31

His His His His His His His His His His His His His His His
1               5                   10                  15

<210> SEQ ID NO 32
<211> LENGTH: 8
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(8)
<223> OTHER INFORMATION: /replace="ornithine"

<400> SEQUENCE: 32

Xaa Xaa Xaa Xaa Xaa Xaa Xaa Xaa
1               5

<210> SEQ ID NO 33
<211> LENGTH: 9
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(9)
<223> OTHER INFORMATION: /replace="ornithine"

<400> SEQUENCE: 33

Xaa Xaa Xaa Xaa Xaa Xaa Xaa Xaa Xaa
1               5

<210> SEQ ID NO 34
<211> LENGTH: 10
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(10)
<223> OTHER INFORMATION: /replace="ornithine"

<400> SEQUENCE: 34

Xaa Xaa Xaa Xaa Xaa Xaa Xaa Xaa Xaa Xaa
1               5                   10

<210> SEQ ID NO 35
<211> LENGTH: 11
<212> TYPE: PRT
<213> ORGANISM: Artificial Sequence
<220> FEATURE:
```

```
<223> OTHER INFORMATION: Description of artificial sequence: exemplary
      cationic peptide according to formula (II)
<220> FEATURE:
<221> NAME/KEY: VARIANT
<222> LOCATION: (1)..(11)
<223> OTHER INFORMATION: /replace="ornithine"

<400> SEQUENCE: 35

Xaa Xaa Xaa Xaa Xaa Xaa Xaa Xaa Xaa Xaa Xaa
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(12)
<223> OTHER INFORMATION: /replace="ornithine"

<400> SEQUENCE: 36

Xaa Xaa Xaa Xaa Xaa Xaa Xaa Xaa Xaa Xaa Xaa Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(13)
<223> OTHER INFORMATION: /replace="ornithine"

<400> SEQUENCE: 37

Xaa Xaa Xaa Xaa Xaa Xaa Xaa Xaa Xaa Xaa Xaa Xaa Xaa
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(14)
<223> OTHER INFORMATION: /replace="ornithine"

<400> SEQUENCE: 38

Xaa Xaa Xaa Xaa Xaa Xaa Xaa Xaa Xaa Xaa Xaa Xaa Xaa Xaa
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)
<220> FEATURE:
<221> NAME/KEY: VARIANT
<222> LOCATION: (1)..(15)
<223> OTHER INFORMATION: /replace="ornithine"
```

```
<400> SEQUENCE: 39

Xaa Xaa Xaa Xaa Xaa Xaa Xaa Xaa Xaa Xaa Xaa Xaa Xaa Xaa Xaa
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of artificial sequence: exemplary
      cationic peptide according to formula (II)

<400> SEQUENCE: 40

His His His Arg Arg Arg Arg Arg Arg Arg Arg Arg Ser Ser Tyr
1               5                   10                  15

<210> SEQ ID NO 41
<211> LENGTH: 10
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 41

Cys Arg Arg Arg Arg Arg Arg Arg Arg Cys
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 42

Cys Arg Arg Arg Arg Arg Arg Arg Arg Arg Cys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 43

Cys Arg Arg Arg Arg Arg Arg Arg Arg Arg Arg Cys
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 44

Cys Arg Arg Arg Arg Arg Arg Arg Arg Arg Arg Arg Cys
1               5                   10
```

<210> SEQ ID NO 45
<211> LENGTH: 14
<212> TYPE: PRT
<213> ORGANISM: Artificial Sequence
<220> FEATURE:
<223> OTHER INFORMATION: Description of Sequence: cationic or
    polycationic peptide as component P2 having formula (IIb): Cys
    {(Arg)l;(Lys)m;(His)n;(Orn)o;(Xaa)x} Cys

<400> SEQUENCE: 45

Cys Arg Arg Arg Arg Arg Arg Arg Arg Arg Arg Arg Arg Cys
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Description of Sequence: cationic or
    polycationic peptide as component P2 having formula (IIb): Cys
    {(Arg)l;(Lys)m;(His)n;(Orn)o;(Xaa)x} Cys

<400> SEQUENCE: 46

Cys Arg Arg Arg Arg Arg Arg Arg Arg Arg Arg Arg Arg Arg Cys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Sequence: cationic or
    polycationic peptide as component P2 having formula (IIb): Cys
    {(Arg)l;(Lys)m;(His)n;(Orn)o;(Xaa)x} Cys

<400> SEQUENCE: 47

Cys Arg Arg Arg Arg Arg Arg Arg Arg Arg Arg Arg Arg Arg Arg Cys
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Description of Sequence: cationic or
    polycationic peptide as component P2 having formula (IIb): Cys
    {(Arg)l;(Lys)m;(His)n;(Orn)o;(Xaa)x} Cys

<400> SEQUENCE: 48

Cys Arg Arg Arg Arg Arg Arg Arg Arg Arg Arg Arg Arg Arg Arg Arg
1               5                   10                  15

Cys

<210> SEQ ID NO 49
<211> LENGTH: 10
<212> TYPE: PRT
<213> ORGANISM: Artificial Sequence
<220> FEATURE:
<223> OTHER INFORMATION: Description of Sequence: cationic or
    polycationic peptide as component P2 having formula (IIb): Cys
    {(Arg)l;(Lys)m;(His)n;(Orn)o;(Xaa)x} Cys

<400> SEQUENCE: 49

Cys Lys Lys Lys Lys Lys Lys Lys Lys Cys
1               5                   10

<210> SEQ ID NO 50

```
-continued

<211> LENGTH: 11
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 50

Cys Lys Lys Lys Lys Lys Lys Lys Lys Lys Cys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 51

Cys Lys Lys Lys Lys Lys Lys Lys Lys Lys Lys Cys
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 52

Cys Lys Lys Lys Lys Lys Lys Lys Lys Lys Lys Lys Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 53

Cys Lys Lys Lys Lys Lys Lys Lys Lys Lys Lys Lys Lys Cys
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 54

Cys Lys Lys Lys Lys Lys Lys Lys Lys Lys Lys Lys Lys Lys Cys
1               5                   10                  15

<210> SEQ ID NO 55
<211> LENGTH: 16
<212> TYPE: PRT
<213> ORGANISM: Artificial Sequence
<220> FEATURE:
```

<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 55

Cys Lys Lys Lys Lys Lys Lys Lys Lys Lys Lys Lys Lys Lys Cys
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 56

Cys Lys Lys Lys Lys Lys Lys Lys Lys Lys Lys Lys Lys Lys Lys
1               5                   10                  15

Cys

<210> SEQ ID NO 57
<211> LENGTH: 10
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 57

Cys His His His His His His His His Cys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 58

Cys His His His His His His His His His Cys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 59

Cys His His His His His His His His His Cys
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys -continued {(Arg)l;(Lys)m;(His)n;(Orn)o;(Xaa)x} Cys

<400> SEQUENCE: 60

Cys His His His His His His His His His His Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 61

Cys His His His His His His His His His His His Cys
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 62

Cys His His His His His His His His His His His His Cys
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 63

Cys His His His His His His His His His His His His His Cys
1               5                   10                  15

<210> SEQ ID NO 64
<211> LENGTH: 17
<212> TYPE: DNA
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 64
chhhhhhhhh hhhhhhc                                              17

<210> SEQ ID NO 65
<211> LENGTH: 10
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(9)
<223> OTHER INFORMATION: Orn

<400> SEQUENCE: 65

Cys Xaa Xaa Xaa Xaa Xaa Xaa Xaa Xaa Cys
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(10)
<223> OTHER INFORMATION: Orn

<400> SEQUENCE: 66

Cys Xaa Xaa Xaa Xaa Xaa Xaa Xaa Xaa Xaa Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(11)
<223> OTHER INFORMATION: Orn

<400> SEQUENCE: 67

Cys Xaa Xaa Xaa Xaa Xaa Xaa Xaa Xaa Xaa Xaa Cys
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(12)
<223> OTHER INFORMATION: Orn

<400> SEQUENCE: 68

Cys Xaa Xaa Xaa Xaa Xaa Xaa Xaa Xaa Xaa Xaa Xaa Cys
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(13)
<223> OTHER INFORMATION: Orn

<400> SEQUENCE: 69

Cys Xaa Xaa Xaa Xaa Xaa Xaa Xaa Xaa Xaa Xaa Xaa Cys
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(14)
<223> OTHER INFORMATION: Orn

<400> SEQUENCE: 70

Cys Xaa Xaa Xaa Xaa Xaa Xaa Xaa Xaa Xaa Xaa Xaa Xaa Xaa Cys
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(15)
<223> OTHER INFORMATION: Orn

<400> SEQUENCE: 71

Cys Xaa Xaa Xaa Xaa Xaa Xaa Xaa Xaa Xaa Xaa Xaa Xaa Xaa Xaa Cys
1               5                   10                  15

<210> SEQ ID NO 72
<211> LENGTH: 17
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys
<220> FEATURE:
<221> NAME/KEY: MOD_RES
<222> LOCATION: (2)..(16)
<223> OTHER INFORMATION: Orn

<400> SEQUENCE: 72

Cys Xaa Xaa Xaa Xaa Xaa Xaa Xaa Xaa Xaa Xaa Xaa Xaa Xaa Xaa Xaa
1               5                   10                  15

Cys

<210> SEQ ID NO 73
<211> LENGTH: 11
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 73

Cys Arg Arg Arg Arg Arg Arg Arg Arg Arg Cys
1               5                   10

<210> SEQ ID NO 74

```
<211> LENGTH: 14
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 74

Cys Arg Arg Arg Arg Arg Arg Arg Arg Arg His His His Cys
1               5                   10

<210> SEQ ID NO 75
<211> LENGTH: 17
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 75

Cys His His His Arg Arg Arg Arg Arg Arg Arg Arg Arg His His His
1               5                   10                  15

Cys

<210> SEQ ID NO 76
<211> LENGTH: 17
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 76

Cys Tyr Ser Ser Arg Arg Arg Arg Arg Arg Arg Arg Arg Ser Ser Tyr
1               5                   10                  15

Cys

<210> SEQ ID NO 77
<211> LENGTH: 17
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 77

Cys His His His Arg Arg Arg Arg Arg Arg Arg Arg Arg Ser Ser Tyr
1               5                   10                  15

Cys

<210> SEQ ID NO 78
<211> LENGTH: 14
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 78

Cys Arg Lys His Arg Lys His Arg Lys His Arg Lys His Cys
1               5                   10
```

<210> SEQ ID NO 79
<211> LENGTH: 10
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 79

Cys Tyr Arg Lys His Arg Lys His Arg Cys
1               5                   10

<210> SEQ ID NO 80
<211> LENGTH: 17
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 80

Cys His His His Arg Arg Arg Arg Arg Arg Arg Arg Arg His His His
1               5                   10                  15

Cys

<210> SEQ ID NO 81
<211> LENGTH: 23
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 81

Cys His His His His His His Arg Arg Arg Arg Arg Arg Arg Arg
1               5                   10                  15

His His His His His His Cys
            20

<210> SEQ ID NO 82
<211> LENGTH: 12
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 82

Cys His His His Arg Arg Arg Arg His His His Cys
1               5                   10

<210> SEQ ID NO 83
<211> LENGTH: 18
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 83

Cys His His His His His His Arg Arg Arg Arg His His His His His
1               5                   10                  15

His Cys

<210> SEQ ID NO 84
<211> LENGTH: 14
<212> TYPE: PRT
<213> ORGANISM: Artificial Sequence
<220> FEATURE:
<223> OTHER INFORMATION: Description of Sequence: cationic or
      polycationic peptide as component P2 having formula (IIb): Cys
      {(Arg)l;(Lys)m;(His)n;(Orn)o;(Xaa)x} Cys

<400> SEQUENCE: 84

Cys Arg Arg Arg Arg Arg Arg Arg Arg Arg Arg Arg Arg Cys
1               5                   10

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93
<211> LENGTH: 4
<212> TYPE: PRT
<213> ORGANISM: Artificial Sequence

```
<220> FEATURE:
<223> OTHER INFORMATION: Exemplary aromatic amino acid component (AA)

<400> SEQUENCE: 93

Trp Tyr Trp Tyr
1

<210> SEQ ID NO 94
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 94

Tyr Trp Tyr Trp
1

<210> SEQ ID NO 95
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 95

Trp Trp Trp Trp
1

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102
<211> LENGTH: 4
```

```
<212> TYPE: PRT
<213> ORGANISM: Artificial Sequence
<220> FEATURE:
<223> OTHER INFORMATION: Exemplary aromatic amino acid component (AA)

<400> SEQUENCE: 102

Phe Tyr Phe Tyr
1

<210> SEQ ID NO 103
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 103

Tyr Phe Tyr Phe
1

<210> SEQ ID NO 104
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 104

Phe Phe Phe Phe
1

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<211> LENGTH: 4
<212> TYPE: PRT
<213> ORGANISM: Artificial Sequence
<220> FEATURE:
<223> OTHER INFORMATION: Exemplary aromatic amino acid component (AA)
```

```
<400> SEQUENCE: 110

Phe Trp Phe Trp
1

<210> SEQ ID NO 111
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 111

Trp Phe Trp Phe
1

<210> SEQ ID NO 112
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 112

Tyr Tyr Tyr Tyr
1

<210> SEQ ID NO 113

<400> SEQUENCE: 113

000

<210> SEQ ID NO 114

<400> SEQUENCE: 114

000

<210> SEQ ID NO 115
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 115

Cys Trp Tyr Cys
1

<210> SEQ ID NO 116
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 116

Cys Tyr Trp Cys
1

<210> SEQ ID NO 117
<211> LENGTH: 4
<212> TYPE: PRT
<213> ORGANISM: Artificial Sequence
<220> FEATURE:
<223> OTHER INFORMATION: Exemplary aromatic amino acid component (AA)
```

```
<400> SEQUENCE: 117

Cys Trp Trp Cys
1

<210> SEQ ID NO 118
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 118

Cys Tyr Tyr Cys
1

<210> SEQ ID NO 119
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 119

Cys Trp Tyr Trp Cys
1               5

<210> SEQ ID NO 120
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 120

Cys Tyr Trp Tyr Cys
1               5

<210> SEQ ID NO 121
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 121

Cys Trp Trp Trp Cys
1               5

<210> SEQ ID NO 122
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 122

Cys Tyr Tyr Tyr Cys
1               5

<210> SEQ ID NO 123
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 123
```

```
Cys Trp Tyr Trp Tyr Cys
1               5

<210> SEQ ID NO 124
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 124

Cys Tyr Trp Tyr Trp Cys
1               5

<210> SEQ ID NO 125
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 125

Cys Trp Trp Trp Trp Cys
1               5

<210> SEQ ID NO 126
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 126

Cys Tyr Tyr Tyr Tyr Cys
1               5

<210> SEQ ID NO 127

<400> SEQUENCE: 127

000

<210> SEQ ID NO 128
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 128

Cys Phe Tyr Cys
1

<210> SEQ ID NO 129
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 129

Cys Tyr Phe Cys
1

<210> SEQ ID NO 130
<211> LENGTH: 4
```

```
<212> TYPE: PRT
<213> ORGANISM: Artificial Sequence
<220> FEATURE:
<223> OTHER INFORMATION: Exemplary aromatic amino acid component (AA)

<400> SEQUENCE: 130

Cys Phe Phe Cys
1

<210> SEQ ID NO 131
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 131

Cys Tyr Tyr Cys
1

<210> SEQ ID NO 132
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 132

Cys Phe Tyr Phe Cys
1               5

<210> SEQ ID NO 133
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 133

Cys Tyr Phe Tyr Cys
1               5

<210> SEQ ID NO 134
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 134

Cys Phe Phe Phe Cys
1               5

<210> SEQ ID NO 135
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 135

Cys Tyr Tyr Tyr Cys
1               5

<210> SEQ ID NO 136
<211> LENGTH: 6
<212> TYPE: PRT
```

```
<213> ORGANISM: Artificial Sequence
<220> FEATURE:
<223> OTHER INFORMATION: Exemplary aromatic amino acid component (AA)

<400> SEQUENCE: 136

Cys Phe Tyr Phe Tyr Cys
 1               5

<210> SEQ ID NO 137
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 137

Cys Tyr Phe Tyr Phe
 1               5

<210> SEQ ID NO 138
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 138

Cys Phe Phe Phe Phe Cys
 1               5

<210> SEQ ID NO 139
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 139

Cys Phe Trp Cys
 1

<210> SEQ ID NO 140
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 140

Cys Trp Phe Cys
 1

<210> SEQ ID NO 141
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 141

Cys Phe Phe Cys
 1

<210> SEQ ID NO 142
<211> LENGTH: 5
<212> TYPE: PRT
<213> ORGANISM: Artificial Sequence
```

```
<220> FEATURE:
<223> OTHER INFORMATION: Exemplary aromatic amino acid component (AA)

<400> SEQUENCE: 142

Cys Phe Trp Phe Cys
1               5

<210> SEQ ID NO 143
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 143

Cys Trp Phe Trp Cys
1               5

<210> SEQ ID NO 144
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 144

Cys Phe Trp Phe Trp Cys
1               5

<210> SEQ ID NO 145
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 145

Cys Trp Phe Trp Phe Cys
1               5

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150
```

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 154

Ser Thr Ser Thr
1

<210> SEQ ID NO 155
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 155

Thr Ser Thr Ser
1

<210> SEQ ID NO 156
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 156

Ser Ser Ser Ser
1

<210> SEQ ID NO 157
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 157

Thr Thr Thr Thr
1

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 166

Gln Asn Gln Asn
1

<210> SEQ ID NO 167
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

```
<400> SEQUENCE: 167

Asn Gln Asn Gln
1

<210> SEQ ID NO 168
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 168

Gln Gln Gln Gln
1

<210> SEQ ID NO 169
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 169

Asn Asn Asn Asn
1

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176
```

```
<400> SEQUENCE: 176

000

<210> SEQ ID NO 177

<400> SEQUENCE: 177

000

<210> SEQ ID NO 178
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 178

Ser Asn Ser Asn
1

<210> SEQ ID NO 179
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 179

Asn Ser Asn Ser
1

<210> SEQ ID NO 180
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 180

Ser Ser Ser Ser
1

<210> SEQ ID NO 181
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 181

Asn Asn Asn Asn
1

<210> SEQ ID NO 182

<400> SEQUENCE: 182

000

<210> SEQ ID NO 183

<400> SEQUENCE: 183
```

```
000
```

<210> SEQ ID NO 184
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 184

Cys Ser Thr Cys
1

<210> SEQ ID NO 185
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 185

Cys Thr Ser Cys
1

<210> SEQ ID NO 186
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 186

Cys Ser Ser Cys
1

<210> SEQ ID NO 187
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 187

Cys Thr Thr Cys
1

<210> SEQ ID NO 188
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 188

Cys Ser Thr Ser Cys
1               5

<210> SEQ ID NO 189
<211> LENGTH: 5
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 189

Cys Thr Ser Thr Cys
1               5

<210> SEQ ID NO 190
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 190

Cys Ser Ser Ser Cys
1               5

<210> SEQ ID NO 191
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 191

Cys Thr Thr Thr Cys
1               5

<210> SEQ ID NO 192
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 192

Cys Ser Thr Ser Thr Cys
1               5

<210> SEQ ID NO 193
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 193

Cys Thr Ser Thr Ser Cys
1               5

<210> SEQ ID NO 194
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 194

Cys Ser Ser Ser Ser Cys
1               5

<210> SEQ ID NO 195

```
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 195

Cys Thr Thr Thr Thr Cys
1               5

<210> SEQ ID NO 196

<400> SEQUENCE: 196

000

<210> SEQ ID NO 197

<400> SEQUENCE: 197

000

<210> SEQ ID NO 198
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 198

Cys Gln Asn Cys
1

<210> SEQ ID NO 199
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 199

Cys Asn Gln Cys
1

<210> SEQ ID NO 200
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 200

Cys Gln Gln Cys
1

<210> SEQ ID NO 201
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 201
```

Cys Asn Asn Cys
1

<210> SEQ ID NO 202
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 202

Cys Gln Asn Gln Cys
1               5

<210> SEQ ID NO 203
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 203

Cys Asn Gln Asn Cys
1               5

<210> SEQ ID NO 204
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 204

Cys Gln Gln Gln Cys
1               5

<210> SEQ ID NO 205
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 205

Cys Asn Asn Asn Cys
1               5

<210> SEQ ID NO 206
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 206

Cys Gln Asn Gln Asn Cys
1               5

<210> SEQ ID NO 207
<211> LENGTH: 6
<212> TYPE: PRT
<213> ORGANISM: Artificial Sequence
<220> FEATURE:

```
<223> OTHER INFORMATION: Exemplary hydrophilic (and preferably non
      charged polar) amino acid component (AA)

<400> SEQUENCE: 207

Cys Asn Gln Asn Gln Cys
1               5

<210> SEQ ID NO 208
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 208

Cys Gln Gln Gln Gln Cys
1               5

<210> SEQ ID NO 209
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 209

Cys Asn Asn Asn Asn Cys
1               5

<210> SEQ ID NO 210

<400> SEQUENCE: 210

000

<210> SEQ ID NO 211

<400> SEQUENCE: 211

000

<210> SEQ ID NO 212
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 212

Cys Ser Asn Cys
1

<210> SEQ ID NO 213
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 213

Cys Asn Ser Cys
1
```

```
<210> SEQ ID NO 214
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 214

Cys Ser Ser Cys
1

<210> SEQ ID NO 215
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 215

Cys Asn Asn Cys
1

<210> SEQ ID NO 216
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 216

Cys Ser Asn Ser Cys
1               5

<210> SEQ ID NO 217
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 217

Cys Asn Ser Asn Cys
1               5

<210> SEQ ID NO 218
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 218

Cys Ser Ser Ser Cys
1               5

<210> SEQ ID NO 219
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 219
```

```
Cys Asn Asn Cys
1               5

<210> SEQ ID NO 220
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 220

Cys Ser Asn Ser Asn Cys
1               5

<210> SEQ ID NO 221
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 221

Cys Asn Ser Asn Ser Cys
1               5

<210> SEQ ID NO 222
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 222

Cys Ser Ser Ser Ser Cys
1               5

<210> SEQ ID NO 223
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 223

Cys Asn Asn Asn Asn Cys
1               5

<210> SEQ ID NO 224

<400> SEQUENCE: 224

000

<210> SEQ ID NO 225

<400> SEQUENCE: 225

000

<210> SEQ ID NO 226

<400> SEQUENCE: 226
```

-continued

```
000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 232

Leu Val Leu Val
1

<210> SEQ ID NO 233
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 233

Val Leu Val Leu
1

<210> SEQ ID NO 234
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 234

Leu Leu Leu Leu
1

<210> SEQ ID NO 235
<211> LENGTH: 4
```

```
<212> TYPE: PRT
<213> ORGANISM: Artificial Sequence
<220> FEATURE:
<223> OTHER INFORMATION: Exemplary lipophilic amino acid component (AA)

<400> SEQUENCE: 235

Val Val Val Val
1

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 244

Ile Ala Ile Ala
1
```

```
<210> SEQ ID NO 245
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 245

Ala Ile Ala Ile
1

<210> SEQ ID NO 246
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 246

Ile Ile Ile Ile
1

<210> SEQ ID NO 247
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 247

Ala Ala Ala Ala
1

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253
```

```
000

<210> SEQ ID NO 254

<400> SEQUENCE: 254

000

<210> SEQ ID NO 255

<400> SEQUENCE: 255

000

<210> SEQ ID NO 256
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 256

Met Ala Met Ala
1

<210> SEQ ID NO 257
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 257

Ala Met Ala Met
1

<210> SEQ ID NO 258
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 258

Met Met Met Met
1

<210> SEQ ID NO 259

<400> SEQUENCE: 259

000

<210> SEQ ID NO 260

<400> SEQUENCE: 260

000

<210> SEQ ID NO 261
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 261
```

```
Cys Leu Val Cys
1

<210> SEQ ID NO 262
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 262

Cys Val Leu Cys
1

<210> SEQ ID NO 263
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 263

Cys Leu Leu Cys
1

<210> SEQ ID NO 264
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 264

Cys Val Val Cys
1

<210> SEQ ID NO 265
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 265

Cys Leu Val Leu Cys
1               5

<210> SEQ ID NO 266
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 266

Cys Val Leu Val Cys
1               5

<210> SEQ ID NO 267
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 267

Cys Leu Leu Leu Cys
```

```
1               5

<210> SEQ ID NO 268
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 268

Cys Val Val Val Cys
1               5

<210> SEQ ID NO 269
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 269

Cys Leu Val Leu Val Cys
1               5

<210> SEQ ID NO 270
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 270

Cys Val Leu Val Leu Cys
1               5

<210> SEQ ID NO 271
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 271

Cys Leu Leu Leu Leu Cys
1               5

<210> SEQ ID NO 272
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 272

Cys Val Val Val Val Cys
1               5

<210> SEQ ID NO 273

<400> SEQUENCE: 273

000

<210> SEQ ID NO 274

<400> SEQUENCE: 274
```

```
000

<210> SEQ ID NO 275
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 275

Cys Ile Ala Cys
1

<210> SEQ ID NO 276
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 276

Cys Ala Ile Cys
1

<210> SEQ ID NO 277
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 277

Cys Ile Ile Cys
1

<210> SEQ ID NO 278
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 278

Cys Ala Ala Cys
1

<210> SEQ ID NO 279
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 279

Cys Ile Ala Ile Cys
1               5

<210> SEQ ID NO 280
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 280

Cys Ala Ile Ala Cys
1               5
```

```
<210> SEQ ID NO 281
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 281

Cys Ile Ile Ile Cys
1               5

<210> SEQ ID NO 282
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 282

Cys Ala Ala Ala Cys
1               5

<210> SEQ ID NO 283
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 283

Cys Ile Ala Ile Ala Cys
1               5

<210> SEQ ID NO 284
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 284

Cys Ala Ile Ala Ile Cys
1               5

<210> SEQ ID NO 285
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 285

Cys Ile Ile Ile Ile Cys
1               5

<210> SEQ ID NO 286
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 286

Cys Ala Ala Ala Ala Cys
1               5
```

<210> SEQ ID NO 287

<400> SEQUENCE: 287

000

<210> SEQ ID NO 288
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 288

Cys Met Ala Cys
1

<210> SEQ ID NO 289
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 289

Cys Ala Met Cys
1

<210> SEQ ID NO 290
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 290

Cys Met Met Cys
1

<210> SEQ ID NO 291
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 291

Cys Ala Ala Cys
1

<210> SEQ ID NO 292
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 292

Cys Met Ala Met Cys
1               5

<210> SEQ ID NO 293
<211> LENGTH: 5
<212> TYPE: PRT
<213> ORGANISM: Artificial Sequence
<220> FEATURE:
<223> OTHER INFORMATION: Exemplary lipophilic amino acid component (AA)

```
<400> SEQUENCE: 293

Cys Ala Met Ala Cys
1               5

<210> SEQ ID NO 294
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 294

Cys Met Met Met Cys
1               5

<210> SEQ ID NO 295
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 295

Cys Ala Ala Ala Cys
1               5

<210> SEQ ID NO 296
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 296

Cys Met Ala Met Ala Cys
1               5

<210> SEQ ID NO 297
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 297

Cys Ala Met Ala Met Cys
1               5

<210> SEQ ID NO 298
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 298

Cys Met Met Met Met Cys
1               5

<210> SEQ ID NO 299
<211> LENGTH: 6
<212> TYPE: PRT
<213> ORGANISM: Artificial Sequence
<220> FEATURE:
<223> OTHER INFORMATION: Exemplary lipophilic amino acid component (AA)
```

```
<400> SEQUENCE: 299

Cys Ala Ala Ala Ala Cys
1               5

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 308

Asp His Asp His
1

<210> SEQ ID NO 309
<211> LENGTH: 4
<212> TYPE: PRT
<213> ORGANISM: Artificial Sequence
```

```
<220> FEATURE:
<223> OTHER INFORMATION: Exemplary weak basic amino acid component (AA)

<400> SEQUENCE: 309

His Asp His Asp
1

<210> SEQ ID NO 310
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 310

Asp Asp Asp Asp
1

<210> SEQ ID NO 311
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 311

His His His His
1

<210> SEQ ID NO 312

<400> SEQUENCE: 312

000

<210> SEQ ID NO 313

<400> SEQUENCE: 313

000

<210> SEQ ID NO 314
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 314

Cys Asp His Cys
1

<210> SEQ ID NO 315
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 315

Cys His Asp Cys
1

<210> SEQ ID NO 316
<211> LENGTH: 4
<212> TYPE: PRT
<213> ORGANISM: Artificial Sequence
```

```
<220> FEATURE:
<223> OTHER INFORMATION: Exemplary weak basic amino acid component (AA)

<400> SEQUENCE: 316

Cys Asp Asp Cys
1

<210> SEQ ID NO 317
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 317

Cys His His Cys
1

<210> SEQ ID NO 318
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 318

Cys Asp His Asp Cys
1               5

<210> SEQ ID NO 319
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 319

Cys His Asp His Cys
1               5

<210> SEQ ID NO 320
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 320

Cys Asp Asp Asp Cys
1               5

<210> SEQ ID NO 321
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 321

Cys His His His Cys
1               5

<210> SEQ ID NO 322
<211> LENGTH: 6
<212> TYPE: PRT
<213> ORGANISM: Artificial Sequence
<220> FEATURE:
```

```
<223> OTHER INFORMATION: Exemplary weak basic amino acid component (AA)

<400> SEQUENCE: 322

Cys Asp His Asp His Cys
1               5

<210> SEQ ID NO 323
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 323

Cys His Asp His Asp Cys
1               5

<210> SEQ ID NO 324
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 324

Cys Asp Asp Asp Asp Cys
1               5

<210> SEQ ID NO 325
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 325

Cys His His His His Cys
1               5

<210> SEQ ID NO 326
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 326

Lys Asp Glu Leu
1

<210> SEQ ID NO 327
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 327

Asp Asp Glu Leu
1

<210> SEQ ID NO 328
<211> LENGTH: 4
<212> TYPE: PRT
<213> ORGANISM: Artificial Sequence
```

-continued

```
<220> FEATURE:
<223> OTHER INFORMATION: Description of sequence: signal peptide,
      localization signal or sequence or nuclear localization signal

<400> SEQUENCE: 328

Asp Glu Glu Leu
1

<210> SEQ ID NO 329
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 329

Gln Glu Asp Leu
1

<210> SEQ ID NO 330
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 330

Arg Asp Glu Leu
1

<210> SEQ ID NO 331
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 331

Gly Gln Asn Leu Ser Thr Ser Asn
1               5

<210> SEQ ID NO 332
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 332

Pro Lys Lys Lys Arg Lys Val
1               5

<210> SEQ ID NO 333
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 333

Pro Gln Lys Lys Ile Lys Ser
1               5
```

<210> SEQ ID NO 334
<211> LENGTH: 5
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 334

Gln Pro Lys Lys Pro
1               5

<210> SEQ ID NO 335
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 335

Arg Lys Lys Arg
1

<210> SEQ ID NO 336
<211> LENGTH: 12
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 336

Arg Lys Lys Arg Arg Gln Arg Arg Arg Ala His Gln
1               5                   10

<210> SEQ ID NO 337
<211> LENGTH: 16
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 337

Arg Gln Ala Arg Arg Asn Arg Arg Arg Trp Arg Glu Arg Gln Arg
1               5                   10                  15

<210> SEQ ID NO 338
<211> LENGTH: 19
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 338

Met Pro Leu Thr Arg Arg Arg Pro Ala Ala Ser Gln Ala Leu Ala Pro
1               5                   10                  15

Pro Thr Pro

<210> SEQ ID NO 339
<211> LENGTH: 8
<212> TYPE: PRT
<213> ORGANISM: Artificial Sequence
<220> FEATURE:
<223> OTHER INFORMATION: Description of sequence: signal peptide, localization signal or sequence or nuclear localization signal

<400> SEQUENCE: 339

Gly Ala Ala Leu Thr Ile Leu Val
1               5

<210> SEQ ID NO 340
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 340

Gly Ala Ala Leu Thr Leu Leu Gly
1               5

<210> SEQ ID NO 341
<211> LENGTH: 15
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 341

Met Asp Asp Gln Arg Asp Leu Ile Ser Asn Asn Glu Gln Leu Pro
1               5                   10                  15

<210> SEQ ID NO 342
<211> LENGTH: 32
<212> TYPE: PRT
<213> ORGANISM: Artificial Sequence
<220> FEATURE:
<223> OTHER INFORMATION: Description of sequence: signal peptide,
      localization signal or sequence or nuclear localization signal
<220> FEATURE:
<221> NAME/KEY: misc_feature
<222> LOCATION: (7)..(8)
<223> OTHER INFORMATION: Xaa = unknown or other
<220> FEATURE:
<221> NAME/KEY: misc_feature
<222> LOCATION: (32)..(32)
<223> OTHER INFORMATION: Xaa = unknown or other

<400> SEQUENCE: 342

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
                20                  25                  30

<210> SEQ ID NO 343
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 343

Gly Cys Val Cys Ser Ser Asn Pro
1               5

<210> SEQ ID NO 344
<211> LENGTH: 8
<212> TYPE: PRT
<213> ORGANISM: Artificial Sequence

```
<220> FEATURE:
<223> OTHER INFORMATION: Description of sequence: signal peptide,
      localization signal or sequence or nuclear localization signal

<400> SEQUENCE: 344

Gly Gln Thr Val Thr Thr Pro Leu
1               5

<210> SEQ ID NO 345
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 345

Gly Gln Glu Leu Ser Gln His Glu
1               5

<210> SEQ ID NO 346
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 346

Gly Asn Ser Pro Ser Tyr Asn Pro
1               5

<210> SEQ ID NO 347
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 347

Gly Val Ser Gly Ser Lys Gly Gln
1               5

<210> SEQ ID NO 348
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 348

Gly Gln Thr Ile Thr Thr Pro Leu
1               5

<210> SEQ ID NO 349
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 349

Gly Gln Thr Leu Thr Thr Pro Leu
1               5
```

<210> SEQ ID NO 350
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 350

Gly Gln Ile Phe Ser Arg Ser Ala
1               5

<210> SEQ ID NO 351
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 351

Gly Gln Ile His Gly Leu Ser Pro
1               5

<210> SEQ ID NO 352
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 352

Gly Ala Arg Ala Ser Val Leu Ser
1               5

<210> SEQ ID NO 353
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 353

Gly Cys Thr Leu Ser Ala Glu Glu
1               5

<210> SEQ ID NO 354
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 354

Gly Ala Gln Val Ser Ser Gln Lys
1               5

<210> SEQ ID NO 355
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 355

Gly Ala Gln Leu Ser Arg Asn Thr
1               5

<210> SEQ ID NO 356
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 356

Gly Asn Ala Ala Ala Ala Lys Lys
1               5

<210> SEQ ID NO 357
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 357

Gly Asn Glu Ala Ser Tyr Pro Leu
1               5

<210> SEQ ID NO 358
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 358

Gly Ser Ser Lys Ser Lys Pro Lys
1               5

<210> SEQ ID NO 359
<211> LENGTH: 60
<212> TYPE: RNA
<213> ORGANISM: Artificial Sequence
<220> FEATURE:
<223> OTHER INFORMATION: Nucleic acid molecule according to formula (V)

<400> SEQUENCE: 359
uagcgaagcu cuuggaccua gguuuuuuuu uuuuuuuggg ugcguuccua gaaguacacg    60

<210> SEQ ID NO 360
<211> LENGTH: 120
<212> TYPE: RNA
<213> ORGANISM: Artificial Sequence
<220> FEATURE:
<223> OTHER INFORMATION: Nucleic acid molecule according to formula (V)

<400> SEQUENCE: 360
uagcgaagcu cuuggaccua gguuuuuuuu uuuuuuuggg ugcguuccua gaaguacacg    60
aucgcuucga gaaccuggau ccaaaaaaaa aaaaaaccc acgcaaggau cuucaugugc    120

<210> SEQ ID NO 361
<211> LENGTH: 229
<212> TYPE: RNA
<213> ORGANISM: Artificial Sequence
<220> FEATURE:

<223> OTHER INFORMATION: Nucleic acid molecule according to formula (V)

<400> SEQUENCE: 361

```
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagauc                229
```

<210> SEQ ID NO 362
<211> LENGTH: 547
<212> TYPE: RNA
<213> ORGANISM: Artificial Sequence
<220> FEATURE:
<223> OTHER INFORMATION: Nucleic acid molecule according to formula (V)

<400> SEQUENCE: 362

```
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agucggaau cuggggauca    360
aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuag                                                              547
```

<210> SEQ ID NO 363
<211> LENGTH: 1083
<212> TYPE: RNA
<213> ORGANISM: Artificial Sequence
<220> FEATURE:
<223> OTHER INFORMATION: Nucleic acid molecule according to formula (V)

<400> SEQUENCE: 363

```
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agucggaau cuggggauca    360
aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuagagc uacgcagguu cgcaauaaaa gcguugauua gugugcauag aacagaccuc   600
uuauucggug aaacgccaga augcuaaauu ccaauaacuc uucccaaaac gcguacggcc   660
gaagacgcgc gcuuaucuug uacguucu cgcacaugga agaaucagcg ggcauggugg     720
uagggcaaua ggggagcugg guagcagcga aaagggccc cugcgcacgu agcuucgcug    780
uucgucugaa acaacccggc auccguugua gcgauccccgu uaucagugu auucuugc     840
```

```
gcacuaagau ucauggugua gucgacaaua acagcgucuu ggcagauucu ggucacgugc    900
ccuaugcccg ggcuugugcc ucucaggugc acagcgauac uuaaagccuu caagguacuc    960
gacgugggua ccgauucgug acacuuccua agauuauucc acuguuuag ccccgcaccg    1020 ccgaccuaaa cugguccaau guauacgcau ucgcugagcg gaucgauaau aaaagcuuga   1080
auu                                                                1083

<210> SEQ ID NO 364
<211> LENGTH: 229
<212> TYPE: RNA
<213> ORGANISM: Artificial Sequence
<220> FEATURE:
<223> OTHER INFORMATION: Nucleic acid molecule according to formula (V)

<400> SEQUENCE: 364
gggagaaagc ucaagcuuau ccaaguaggc uggucaccug uacaacguag ccgguauuuu     60
uuuuuuuuuu uuuuuuuuga ccgucucaag guccaaguua gucugccuau aaaggugcgg    120
auccacagcu gaugaaagac uugugcggua cgguuaaucu ccccuuuuuu uuuuuuuuuu    180
uuuuuaguaa augcgucuac ugaauccagc gaugaugcug gcccagauc                229

<210> SEQ ID NO 365
<211> LENGTH: 546
<212> TYPE: RNA
<213> ORGANISM: Artificial Sequence
<220> FEATURE:
<223> OTHER INFORMATION: Nucleic acid molecule according to formula (V)

<400> SEQUENCE: 365
gggagaaagc ucaagcuuau ccaaguaggc uggucaccug uacaacguag ccgguauuuu     60
uuuuuuuuuu uuuuuuuuga ccgucucaag guccaaguua gucugccuau aaaggugcgg    120
auccacagcu gaugaaagac uugugcggua cgguuaaucu ccccuuuuuu uuuuuuuuuu    180
uuuuuaguaa augcgucuac ugaauccagc gaugaugcug gcccagaucu ucgaccacaa    240
gugcauauag uagucaucga ggucgccuu uuuuuuuuu uuuuuuuuuu uggcccaguu     300
cugagacuuc gcuagagacu acaguuuacg cugcaguagu aaccacgcg gcuauugcag    360 gaaaucccgu ucagguuuuu uuuuuuuuuu uuuuuccgc ucacuaugau uaagaaccag    420
gugggagugu cacugcucucg aggucucacg agagcgcucg auacaguccu uggaagaauc    480
uuuuuuuuuu uuuuuuuuuu uugugcgacg aucacagaga acuucuauuc augcaggucu    540
gcucua                                                              546

<210> SEQ ID NO 366
<211> LENGTH: 1083
<212> TYPE: RNA
<213> ORGANISM: Artificial Sequence
<220> FEATURE:
<223> OTHER INFORMATION: Nucleic acid molecule according to formula (V)

<400> SEQUENCE: 366
gggagaaagc ucaagcuuau ccaaguaggc uggucaccug uacaacguag ccgguauuuu     60
uuuuuuuuuu uuuuuuuuga ccgucucaag guccaaguua gucugccuau aaaggugcgg    120
auccacagcu gaugaaagac uugugcggua cgguuaaucu ccccuuuuuu uuuuuuuuuu    180
```

-continued

```
uuuuuaguaa augcgucuac ugaauccagc gaugaugcug gcccagaucu ucgaccacaa      240
gugcauauag uagucaucga ggggucgccuu uuuuuuuuuu uuuuuuuuuu uggcccaguu      300
cugagacuuc gcuagagacu acaguuacag cugcaguagu aaccacugcg gcuauugcag      360
gaaaucccgu ucagguuuuu uuuuuuuuuu uuuuuuccgc ucacuaugau uaagaaccag      420 guggagugcuc acugcucucg aggucucacg agagcgcucg auacaguccu uggaagaauc      480
uuuuuuuuuu uuuuuuuuuu ugugcgacg aucacagaga acuucuauuc augcaggcu       540 gcucuagaac gaacugaccu gacgccugaa cuuaugagcg ugcguauuuu uuuuuuuuu       600 uuuuuuuuuc ucccaacaa augcgauca auagcugggc uguuggagac gcgcagcaa         660 augccgugc uccauaggac guguagacuu cuauuuuuu uuuuuuuuuu uuucccggg          720 accacaaaua auauucuugc uugguuggc gcaagggccc cguaucaggu cauaaacggg       780
uacauguugc acaggcuccu uuuuuuuuuu uuuuuuuuuu uucgcugagu uauuccgguc      840
ucaaaagacg gcagacguca gucgacaaca cggucuaaag caguccuaca aucgccgug       900 uucgucuguu uuuuuuuuu uuuuuguga accuacacgg cgugcacugu agucgcaau         960 ucauagggua ccggcucaga guuaugccuu gguugaaaac ugcccagcau acuuuuuuuuu   1020 uuuuuuuuuu uucauauucc caugcuaagc aagggaugcc gcgagucaug uuaagcuuga   1080
auu                                                                  1083
```

<210> SEQ ID NO 367
<211> LENGTH: 59
<212> TYPE: RNA
<213> ORGANISM: Artificial Sequence
<220> FEATURE:
<223> OTHER INFORMATION: Nucleic acid molecule according to formula (V)

<400> SEQUENCE: 367

```
uagcgaagcu cuuggaccua ccuuuuuuuu uuuuuucccu gcguuccuag aaguacacg        59
```

<210> SEQ ID NO 368
<211> LENGTH: 120
<212> TYPE: RNA
<213> ORGANISM: Artificial Sequence
<220> FEATURE:
<223> OTHER INFORMATION: Nucleic acid molecule according to formula (V)

<400> SEQUENCE: 368

```
uagcgaagcu cuuggaccua ccuuuuuuuu uuuuuuuccc ugcguuccua gaaguacacg        60
aucgcuucga gaaccuggau ggaaaaaaaa aaaaaaaggg acgcaaggau cuucaugugc      120
```

<210> SEQ ID NO 369
<211> LENGTH: 1857
<212> TYPE: RNA
<213> ORGANISM: Artificial Sequence
<220> FEATURE:
<223> OTHER INFORMATION: Description of Artificial Sequence: mRNA coding
      for Photinus pyralis luciferase: pCV19-Pp luc(GC)-muag-A70-C30

<400> SEQUENCE: 369

```
gggagaaagc uugaggaugg aggacgccaa gaacaucaag aagggcccgg cgcccuucua         60
cccgcuggag acgggaccg ccggcgagca gcuccacaag gccaugaagc gguacgcccu        120
ggugccgggc acgaucgccu ucaccgacgc ccacaucgag gucgacauca ccuacgcgga      180
guacuucgag augagcgugc gccuggccga ggccaugaag cgguacggcc ugaacaccaa      240
ccaccggauc guggugugcu cggagaacag ccugcaguuc uucaugccgg ugcugggcgc      300
```

```
ccucuucauc ggcguggccg ucgccccggc gaacgacauc uacaacgagc gggagcugcu    360
gaacagcaug gggaucagcc agccgaccgu gguguucgug agcaagaagg gccugcagaa    420
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
caugaacagc agcggcagca ccggccugcc gaagggggug gcccugccgc accggaccgc    660
cugcgugcgc uucucgcacg cccgggaccc caucuucggc aaccagauca ucccggacac    720
cgccauccug agcgugguge cguuccacca cggcuucggc auguucacga cccugggcua    780
ccucaucugc ggcuuccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg agugggggcga ggccguggcc aagcgguucc accucccggg   1020
cauccgccag ggcuacggcc ugaccgagac cacgagcgcg auccugauca cccccgaggg   1080
ggacgacaag ccgggcgccg ugggcaaggu gguccguuc uucgaggcca aggugguga    1140 ccuggacacc ggcaagaccc ugggcgugaa ccagcggggc gagcugugcg ugcgggggcc   1200
gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag gugcgccgg ccgagcugga    1380 gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cgugguguuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggcccuccuc cccuccuugc accgagauua   1740
auaaaaaaaa aaaaaaaaaa aaaaaaaaaa aaaaaaaaaa aaaaaaaaaa aaaaaaaaaa   1800
aaaaaauauu cccccccccc cccccccccc cccccccccc ucuagacaau uggaauu      1857
```